(12) United States Patent
Yano et al.

(10) Patent No.: US 9,718,905 B2
(45) Date of Patent: Aug. 1, 2017

(54) POLYTHIOPHENE, WATER-SOLUBLE ELECTRICALLY CONDUCTIVE POLYMER USING IT, AND METHOD FOR PRODUCING IT

(71) Applicant: TOSOH CORPORATION, Yamaguchi (JP)

(72) Inventors: Hirokazu Yano, Yamaguchi (JP); Masakazu Nishiyama, Yamaguchi (JP); Hiroshi Awano, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 14/412,006

(22) PCT Filed: Jul. 3, 2013

(86) PCT No.: PCT/JP2013/068281
§ 371 (c)(1),
(2) Date: Dec. 30, 2014

(87) PCT Pub. No.: WO2014/007299
PCT Pub. Date: Jan. 9, 2014

(65) Prior Publication Data
US 2015/0337061 A1    Nov. 26, 2015

(30) Foreign Application Priority Data

Jul. 3, 2012 (JP) .................................. 2012-149785
Jul. 3, 2012 (JP) .................................. 2012-149786
(Continued)

(51) Int. Cl.
*C08F 134/04*    (2006.01)
*C09D 5/24*    (2006.01)
(Continued)

(52) U.S. Cl.
CPC .......... *C08F 134/04* (2013.01); *C07D 495/04* (2013.01); *C08G 61/126* (2013.01);
(Continued)

(58) Field of Classification Search
CPC ..................................................... C08F 134/04
(Continued)

(56) References Cited

U.S. PATENT DOCUMENTS 5,569,708 A    10/1996    Wudl et al.
2005/0175861 A1    8/2005    Elschner et al.
(Continued)

FOREIGN PATENT DOCUMENTS

CN    101128421    2/2008
CN    101314634    12/2008
(Continued)

OTHER PUBLICATIONS

Yin Binbin, "Design, Synthesis and Properties of New Water Soluble Polythiophense Derivatives", China Master's Theses Full-text Database, Engineering Technology, I, No. 12, Dec. 15, 2011, pp. 1-52.
(Continued)

*Primary Examiner* — Duc Truong
(74) *Attorney, Agent, or Firm* — Greenblum & Bernstein, P.L.C.

(57) ABSTRACT

To provide a water-soluble polythiophene used as an electrically conductive material, and its production method.
A polythiophene comprising at least one type of structural units selected from the group consisting of structural units represented by the formula (1), structural units represented by the formula (2), structural units represented by the formula (3), structural units represented by the formula (4), structural units represented by the formula (5) and structural units represented by the formula (6). The polythiophene is (Continued)

obtained by polymerizing at least one thiophene compound selected from the group consisting of a thiophene compound represented by the formula (15), a thiophene compound represented by the formula (16) and a thiophene compound represented by the formula (17) in water or an alcohol solvent in the presence of an oxidizing agent.

10 Claims, 14 Drawing Sheets

(30) Foreign Application Priority Data

| | | |
|---|---|---|
| Jul. 27, 2012 | (JP) | 2012-167770 |
| Jul. 27, 2012 | (JP) | 2012-167771 |
| Sep. 6, 2012 | (JP) | 2012-196153 |
| Sep. 11, 2012 | (JP) | 2012-199841 |
| Apr. 4, 2013 | (JP) | 2013-078336 |

(51) Int. Cl.
```
C09D 145/00      (2006.01)
C07D 495/04      (2006.01)
C08G 61/12       (2006.01)
C07D 495/00      (2006.01)
```

(52) U.S. Cl.
CPC ............ *C09D 5/24* (2013.01); *C09D 145/00* (2013.01); *C08G 2261/143* (2013.01); *C08G 2261/1424* (2013.01); *C08G 2261/1452* (2013.01); *C08G 2261/43* (2013.01); *C08G 2261/512* (2013.01); *C08G 2261/54* (2013.01); *C08G 2261/64* (2013.01); *C08G 2261/90* (2013.01); *C08G 2261/94* (2013.01)

(58) Field of Classification Search
USPC ...................................................... 528/377
See application file for complete search history.

(56) References Cited

U.S. PATENT DOCUMENTS

| | | |
|---|---|---|
| 2005/0202274 A1 | 9/2005 | Elschner et al. |
| 2011/0257277 A1 | 10/2011 | Elschner et al. |
| 2012/0147529 A1 | 6/2012 | Biler et al. |

FOREIGN PATENT DOCUMENTS

| | | |
|---|---|---|
| CN | 101490122 | 7/2009 |
| JP | 1-500835 | 3/1989 |
| JP | 1-313521 | 12/1989 |
| JP | 6-49183 | 2/1994 |
| JP | 7-90060 | 4/1995 |
| JP | 8-13873 | 2/1996 |
| JP | 2001-261795 | 9/2001 |
| JP | 2005-226072 | 8/2005 |
| JP | 2006-310023 | 11/2006 |

OTHER PUBLICATIONS

Office Action issued in Chinese Counterpart Patent Appl. No. 201380035065.3, dated Nov. 26, 2015 , along with an english translation thereof.
Roger H. Karlsson et al., "Iron-Catalyzed Polymerization of Alkoxysulfonate-Functionalized 3,4-Ethylenedioxythiophene Gives Water-Soluble Poly(3,4-ethylenedioxythiophene) of High Conductivity", Chemistry of Materials, 2009, pp. 1815-1821.
Denshi Zairyo, "Electric materials and parts", , Feb. 1990, pp. 48-55.
A.O. Patil et al., "Journal of the American Chemical Society", , 1987, pp. 1858-1859.
Kristen M Persson et al., "Electronic control of cell detachment using a self-doped conducting polymer", Advanced Materials, 23 (38), 2011, pp. 4403-4408.
Gianni Zotti et al., "Electrochemical and Chemical Synthesis and Characterization of Sulfonated Poly(3,4-ethylenedioxythiophene): A Novel Water-Solube and Highly Conductive Conjugated Oligomer", Macromol. Chem. Phys., 2002, pp. 1958-1964, vol. 203, No. 13.
Oliver Stephan et al., "Electrochemical behaviour of 3,4-ethylenedioxythiophene functionalized by a sulphonate group, Application to the preparation of poly(3,4-ethylenedioxythiophene) having permanent cation-exchange properties", Journal of Electroanalytical Chemistry, 1998, pp. 217-226, vol. 443, No. 2.
International Search Report in PCT/JP2013/068281 issued Sep. 3, 2013.
International Preliminary Examination Report in PCT/JP2013/068281 issued Jan. 6, 2015.

| Ex. | 34 | 35 | 36 | 37 |
|---|---|---|---|---|
| Photograph of alumina cross section |  |  |  |  |

POLYTHIOPHENE, WATER-SOLUBLE ELECTRICALLY CONDUCTIVE POLYMER USING IT, AND METHOD FOR PRODUCING IT

TECHNICAL FIELD

The present invention relates to a polythiophene, a water-soluble electrically conductive polymer aqueous solution using it, and a method for producing the polythiophene.

BACKGROUND ART

A polymer having π conjugated double bonds represented by polyacetylene, polythiophene, polyaniline, polypyrrole and the like is known to be an electric conductor (electrically conductive polymer) by doping with a donor or an acceptor, and its application to an antistatic agent, a solid electrolyte of a capacitor, an electrically conductive coating material, an electrochromic device, a transparent electrode, a transparent electrically conductive film, a chemical sensor, an actuator, etc. has been studied. Heretofore, an electrically conductive polymer is insoluble and infusible and is thereby problematic in formability, and to dissolve it, a polar organic solvent (for example, an amido solvent) with a heavy environmental burden is necessary. Thus, a water-soluble and easily formable electrically conductive polymer, which is soluble in water with a light environmental burden, has been desired.

In recent years, as an electrically conductive polymer, a polythiophene called poly(3,4-ethylenedioxythiophene) (PEDOT) has been actively studied (for example, Patent Document 1), however, it is known that since 3,4-ethylenedioxythiophene (EDOT) as its material monomer is hardly soluble in water (2.1 g/L water, 0.2 wt %), the obtainable electrically conductive polymer is insoluble in water.

Accordingly, in order to obtain a water-soluble electrically conductive polymer, a method has been proposed in which EDOT is polymerized in the presence of a water-soluble high molecular weight dopant such as polystyrene sulfonic acid (PSS) (for example, Patent Document 2, called PEDOT-PSS).

Patent Document 2 discloses that the polymer becomes water-soluble and has improved formability by polyanions being incorporated both as a dopant and as a water dispersing agent. However, the electrically conductive polymer disclosed in Patent Document 2 has problems such that its electrical conductivity is low since it contains a large quantity of polymer moieties with low electrical conductivity, which do not contribute to doping, it has low heat resistance and water resistance since it has sulfo groups in large excess, and an apparatus may be eroded by strong acidity.

By the way, since the electrically conductive polymer disclosed in Patent Document 2 has both favorable electrical conductivity and formability, its application to a solid polymer electrolyte of a capacitor and printable electronics has been desired.

Examples of the former include a solid electrolyte of an aluminum solid electrolytic capacitor, and a high capacity and a low ESR (equivalent series resistance) as the capacitor performance are to be achieved.

Further, in the case of the latter, for example, when technique of e.g. an inkjet is applied, if the particle size of the electrically conductive polymer in the aqueous solution is large, problems such as clogging of a nozzle may arise.

On the other hand, another method to obtain a water-soluble electrically conductive polymer proposed may be such that a compound having substituents having both a function to impart water solubility and a doping function (for example, sulfo groups or sulfonate groups) introduced in a polymer molecular chain by covalent bonds directly or via a spacer, is polymerized to obtain a water-soluble self-doping electrically conductive polymer which is excellent in the formability (for example, Patent Documents 3 and 4, Non-Patent Documents 1 and 2). Among them, poly(4-(2,3-dihydrothieno[3,4-b][1,4]dioxin-2-lymethoxy)-1-butanesulfonic acid) (PEDT-S) substituted by a straight-chain alkylene sulfonic acid group is reported to have a high electric conductivity of 10-30 S/cm (Patent Document 5, Non-Patent Documents 2 and 3).

As an example of application of a water-soluble self-doping electrically conductive polymer disclosed in such documents, application to an antistatic film-forming material of a resist used at the time of forming a circuit pattern of a semiconductor by electron lithography may be mentioned. This application is thanks to advantageous such that the electrically conductive polymer is water-soluble and is thereby less likely to damage a lipid-soluble resist, and washing with water can be carried out after exposure (for example, Non Patent Document 4). However, along with high integration of a semiconductor in recent years, finer pattern formation is required, and therefore a polymer having a higher electrical conductivity (antistatic performance) has been desired.

Accordingly, a self-doping water-soluble electrically conductive polymer which can impart processability without adding other components which do not contribute to improvement of the electrical conductivity to make the polymer be water-soluble, which has favorable water solubility and electrical conductivity and in addition, which has a sufficiently small particle size of the polymer when formed into an aqueous solution, has been desired.

PRIOR ART DOCUMENTS

Patent Documents

Patent Document 1: Japanese Patent No. 2721700
Patent Document 2: Japanese Patent No. 2636968
Patent Document 3: JP-B-8-13873
Patent Document 4: Japanese Patent No. 3182239
Patent Document 5: Japanese Patent No. 4974095

Non-Patent Documents

Non-Patent Document 1: Journal of the American Chemical Society, 1987, 1858-1859
Non-Patent Document 2: Chemistry of Materials, 2009, 1815-1821
Non-Patent Document 3: Advanced Materials, 23(38), 4403-4408 (2011)
Non-Patent Document 4: Denshi Zairyo (Electric materials and parts), February 1990, 48-55

DISCLOSURE OF INVENTION

Technical Problem

Under these circumstances, the object of the present invention is:
(1) to provide a water-soluble polythiophene used as an electrically conductive material and its production method, and (2) to provide a thiophene compound used as a material of a polythiophene.

Solution to Problem

The present inventors have conducted extensive studies to achieve the above objects and as a result, accomplished the present invention. That is, the present invention provides the following.

[1] A polythiophene comprising at least one type of structural units selected from the group consisting of structural units represented by the following formula (1), structural units represented by the following formula (2), structural units represented by the following formula (3), structural units represented by the following formula (4), structural units represented by the following formula (5) and structural units represented by the following formula (6):

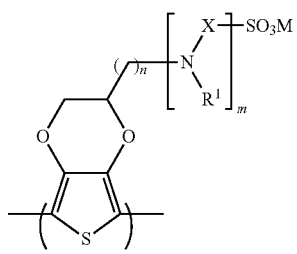
(1)

wherein $R^1$ is a hydrogen atom, a $C_{1-6}$ alkyl group or $C_{6-20}$ aryl group which may have a substituent, or —X—SO$_3$M, X is a $C_{1-6}$ alkylene group or $C_{6-20}$ arylene group which may have a substituent, M is a hydrogen atom, an alkali metal selected from the group consisting of Li, Na and K, NH($R^2$)$_3$ or HNC$_5$H$_5$, $R^2$ is each independently a hydrogen atom or a $C_{1-6}$ alkyl group which may have a substituent, m is an integer of from 0 to 3, and n is an integer of from 0 to 12, provided that n+m≥1;

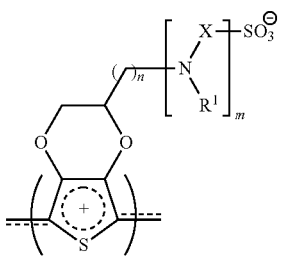
(2)

wherein $R^1$, X, n and m are as defined in the above formula (1);

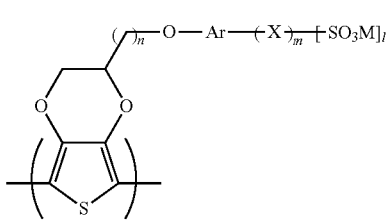
(3)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, NH($R^1$)$_3$ or HNC$_5$H$_5$, $R^1$ is each independently a hydrogen atom or a $C_{1-6}$ alkyl group which may have a substituent, n is an integer of from 0 to 6, m in an integer of 0 or 1, and l is an integer of from 1 to 4;

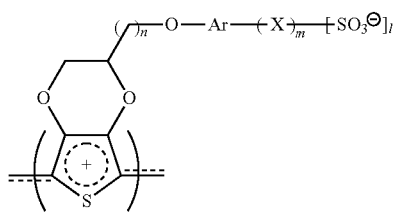
(4)

wherein Ar, X, n, m and l are as defined in the above formula (3);

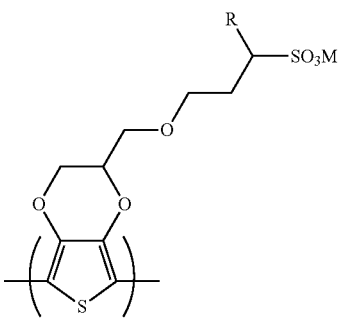
(5)

wherein R is a $C_{1-6}$ linear or branched alkyl group, or a fluorine atom, M is a hydrogen atom, an alkali metal selected from the group consisting of Li, Na and K, NH($R^1$)$_3$ or HNC$_5$H$_5$, and $R^1$ is each independently a hydrogen atom, or a $C_{1-6}$ alkyl group which may have a substituent; and

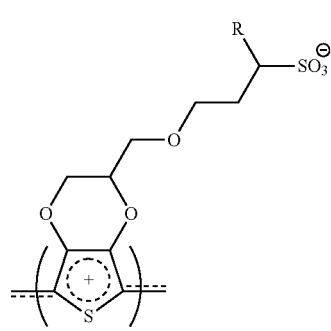
(6)

wherein R is as defined in the above formula (5).

[2] The polythiophene according to the above [1], which contains at least one type of structural units selected from the group consisting of structural units represented by the following formula (7):

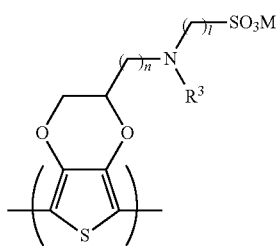

(7)

wherein $R^3$ is a hydrogen atom, a $C_{1-6}$ alkyl group or $C_{6-20}$ aryl group which may have a substituent, or —$(CH_2)_l$—$SO_3M$, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, l is an integer of from 1 to 6, and n is an integer of from 0 to 12;

structural units represented by the following formula (8):

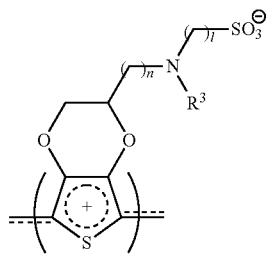

(8)

wherein $R^3$, n and l are as defined in the above formula (7);

structural units represented by the following formula (9):

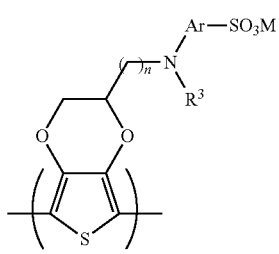

(9)

wherein $R^4$ is a hydrogen atom, a $C_{1-6}$ alkyl group or $C_{6-20}$ aryl group which may have a substituent, or —Ar—$SO_3M$, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, Ar is a $C_{6-20}$ arylene group which may have a substituent, and n is an integer of form 0 to 12;

structural units represented by the following formula (10):

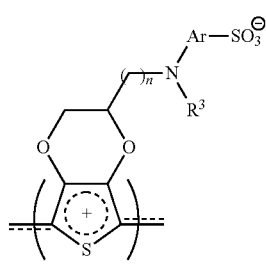

(10)

wherein $R^4$, Ar and n are as defined in the above formula (9);

structural units represented by the following formula (11):

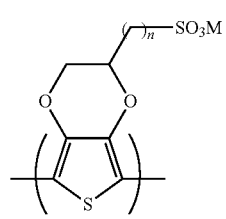

(11)

wherein M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, and n is an integer of from 0 to 12; and structural units represented by the following formula (12):

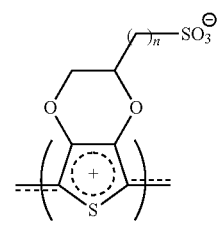

(12)

wherein n is as defined in the above formula (11).

[3] The polythiophene according to the above [1], which contains at least one type of structural units selected from the group consisting of structural units represented by the following formula (13):

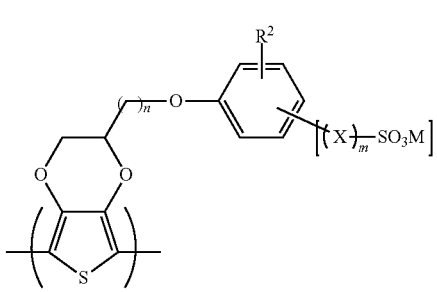

(13)

wherein M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, X is a $C_{1-6}$ alkylene group which may have a substituent, $R^2$ is a hydrogen atom, or a $C_{1-6}$ alkyl group or alkoxy group which may have a substituent, n is an integer of from 0 to 6, m is an integer of 0 or 1, and l is an integer of from 1 to 4; and structural units represented by the following formula (14):

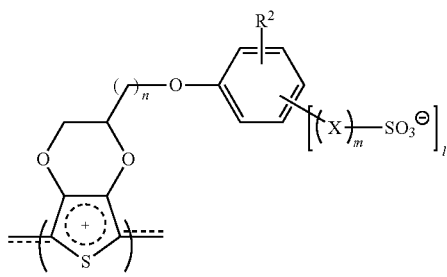
(14)

wherein $R^2$, X, n, m, and l are as defined in the above formula (13).

[4] The polythiophene according to the above [3], wherein in the structural units represented by the formula (13) or (14), $R^2$ is a hydrogen atom and l=1.

[5] The polythiophene according to any one of the above [1] to [4], which has a weight average molecular weight within a range of from 1,000 to 1,000,000 as calculated as polystyrene sulfonic acid.

[6] A water-soluble electrically conductive polymer aqueous solution comprising an aqueous solution of the polythiophene as defined in any one of the above [1] to [5].

[7] A method for producing an electrically conductive coating film, which comprises applying the aqueous solution as defined in the above [6] to a substrate, followed by drying.

[8] Use of the aqueous solution as defined in the above [6] for an electrically conductive coating film.

[9] A method for producing the polythiophene as defined in any one of the above [1] to [5], which comprises polymerizing at least one thiophene compound selected from the group consisting of a thiophene compound represented by the following formula (15), a thiophene compound represented by the following formula (16) and a thiophene compound represented by the following formula (17) in water or an alcohol solvent in the presence of an oxidizing agent:

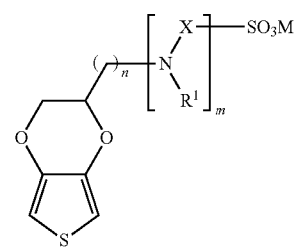
(15)

wherein $R^1$ is a hydrogen atom, a $C_{1-6}$ alkyl group or $C_{6-20}$ aryl group which may have a substituent, or —X—$SO_3M$, X is a $C_{1-6}$ alkylene group or $C_{6-20}$ arylene group which may have a substituent, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, m is an integer of from 0 to 3, and n is an integer of from 0 to 12, provided that n+m≥1;

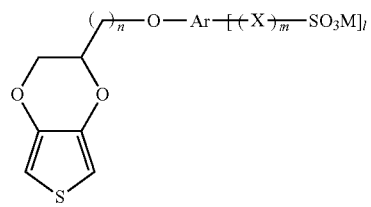
(16)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, n is an integer of from 0 to 6, m is an integer of 0 or 1, and l is an integer of from 1 to 4; and

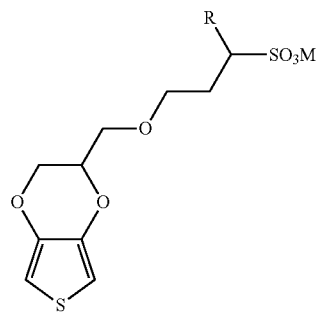
(17)

wherein R is a $C_{1-6}$ linear or branched alkyl group or a fluorine atom, M is a hydrogen atom, an alkali metal selected from the group consisting of Li, Na and K, $NH(R^1)_3$ or $HNC_5H_5$, and $R^1$ is each independently a hydrogen atom or a $C_{1-6}$ alkyl group which may have a substituent.

[10] The production method according to the above [9], wherein the thiophene compound is at least one member selected from the group consisting of a compound represented by the following formula (18), a compound represented by the following formula (19) and a compound represented by the following formula (20):

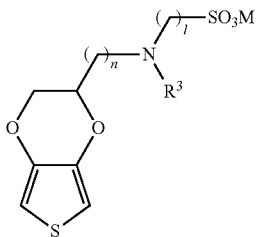
(18)

wherein $R^3$ is a hydrogen atom, a $C_{1-6}$ alkyl group or $C_{6-20}$ aryl group which may have a substituent, or —$(CH_2)_l$—$SO_3M$, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, l is an integer of from 1 to 6, and n is an integer of from 0 to 12:

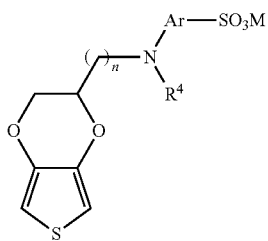
(19)

wherein $R^4$ is a hydrogen atom, a $C_{1-6}$ alkyl group or $C_{6-20}$ aryl group which may have a substituent, or —Ar—SO$_3$M, M is a hydrogen atom, an alkali metal selected from the group consisting of Li, Na and K, NH($R^2$)$_3$ or HNC$_5$H$_5$, $R^2$ is each independently a hydrogen atom or a $C_{1-6}$ alkyl group which may have a substituent, Ar is a $C_{6-20}$ arylene group which may have a substituent, and n is an integer of from 0 to 12;

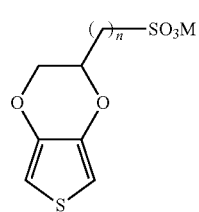
(20)

wherein M is a hydrogen atom, an alkali metal selected from the group consisting of Li, Na and K, NH($R^2$)$_3$ or HNC$_5$H$_5$, $R^2$ is each independently a hydrogen atom or a $C_{1-6}$ alkyl group which may have a substituent, and n is an integer of from 0 to 12.

[11] The production method according to the above [9], wherein the thiophene compound is at least one member selected from the group consisting of a compound represented by the following formula (21):

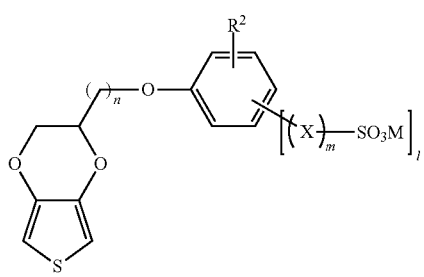
(21)

wherein M is a hydrogen atom, an alkali metal selected from the group consisting of Li, Na and K, NH($R^1$)$_3$ or HNC$_5$H$_5$, $R^1$ is each independently a hydrogen atom or a $C_{1-6}$ alkyl group which may have a substituent, $R^2$ is a hydrogen atom, or a $C_{1-6}$ alkyl group or alkoxy group which may have a substituent, X is a $C_{1-6}$ alkylene group which may have a substituent, n is an integer of from 0 to 6, m is an integer of 0 or 1, and l is an integer of from 1 to 4.

[12] The method for producing a polythiophene according to any one of the above [9] to [11], wherein the oxidizing agent is an iron (III) salt or a combination of a persulfate and an iron (III) salt.

[13] Use of at least one thiophene compound selected from the group consisting of a thiophene compound represented by the following formula (15), a thiophene compound represented by the following formula (16) and a thiophene compound represented by the following formula (17) as a material for producing the polythiophene as defined in the above [1]:

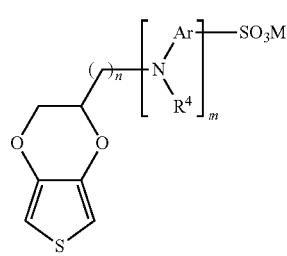
(15)

wherein $R^1$ is a hydrogen atom, a $C_{1-6}$ alkyl group or $C_{6-20}$ aryl group which may have a substituent, or —X—SO$_3$M, X is a $C_{1-6}$ alkylene group or $C_{6-20}$ arylene group which may have a substituent, M is a hydrogen atom, an alkali metal selected from the group consisting of Li, Na and K, NH($R^2$)$_3$ or HNC$_6$H$_5$, $R^2$ is each independently a hydrogen atom or a $C_{1-6}$ alkyl group which may have a substituent, m is an integer of from 0 to 3, and n is an integer of from 0 to 12, provided that n+m≥1:

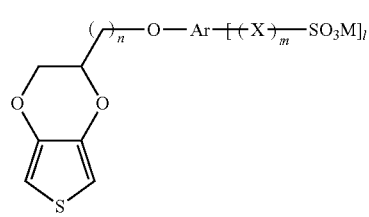
(16)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, NH($R^1$)$_3$ or HNC$_5$H$_5$, $R^1$ is each independently a hydrogen atom or a $C_{1-6}$ alkyl group which may have a substituent, n is an integer of from 0 to 6, m is an integer of 0 or 1, and l is an integer of from 1 to 4; and

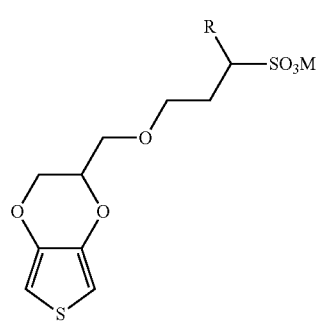
(17)

wherein R is a $C_{1-6}$ linear or branched alkyl group or a fluorine atom, M is a hydrogen atom, an alkali metal selected from the group consisting of Li, Na and K, NH($R^1$)$_3$ or HNC$_5$H$_5$, and $R^1$ is each independently a hydrogen atom or a $C_{1-6}$ alkyl group which may have a substituent.

[14] The use according to the above [13], wherein the thiophene compound is at least one member selected from the group consisting of a compound represented by the following formula (18), a compound represented by the following formula (19) and a compound represented by the following formula (20):

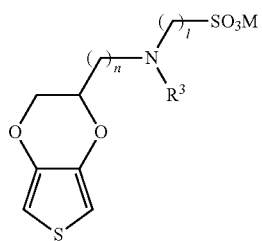

(18)

wherein $R^3$ is a hydrogen atom, a $C_{1-6}$ alkyl group or $C_{6-20}$ aryl group which may have a substituent, or —$(CH_2)_l$—$SO_3M$, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, l is an integer of from 1 to 6, and n is an integer of from 0 to 12:

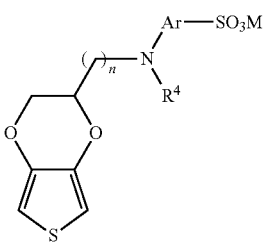

(19)

wherein $R^4$ is a hydrogen atom, a $C_{1-6}$ alkyl group or $C_{6-20}$ aryl group which may have a substituent, or —Ar—$SO_3M$, M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, Ar is a $C_{6-20}$ arylene group which may have a substituent, and n is an integer of from 0 to 12; and

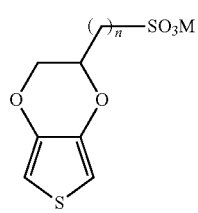

(20)

wherein M is a hydrogen atom, an alkali metal selected from the group consisting of Li, Na and K, $NH(R^2)_3$ or $HNC_5H_5$, $R^2$ is each independently a hydrogen atom or a $C_{1-6}$ alkyl group which may have a substituent, and n is an integer of from 0 to 12.

[15] The use according to the above [13], wherein the thiophene compound is at least one member selected from the group consisting of a compound represented by the following formula (21):

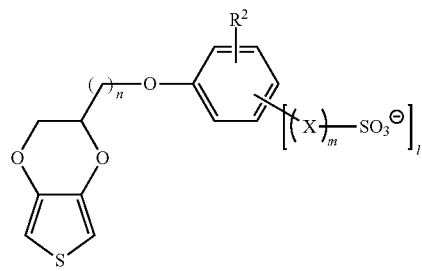

(21)

wherein M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, $R^2$ is a hydrogen atom, or a $C_{1-6}$ alkyl group or alkoxy group which may have a substituent, X is a $C_{1-6}$ alkylene group which may have a substituent, n is an integer of from 0 to 6, m is an integer of 0 or 1, and l is an integer of from 1 to 4.

Advantageous Effects of Invention

According to the present invention, a polythiophene which has all of favorable electrical conductivity, formability and sufficient water solubility, and a thiophene compound as the material thereof can be provided.

Further, since the polythiophene of the present invention has a very small polymer particle size when formed into an aqueous solution, for example, it readily infiltrate into a chemically treated etched aluminum foil of an aluminum solid electrolytic capacitor, thus increasing the area covered with the electrically conductive polymer.

Here, among the polythiophenes of the present invention, a polythiophene having a substituent at the α-position of the sulfo group, is different from PEDT-S disclosed in Patent Document 5, and its electric conductivity is improved as compared with PEDT-S.

DESCRIPTION OF EMBODIMENTS

Figure 1:
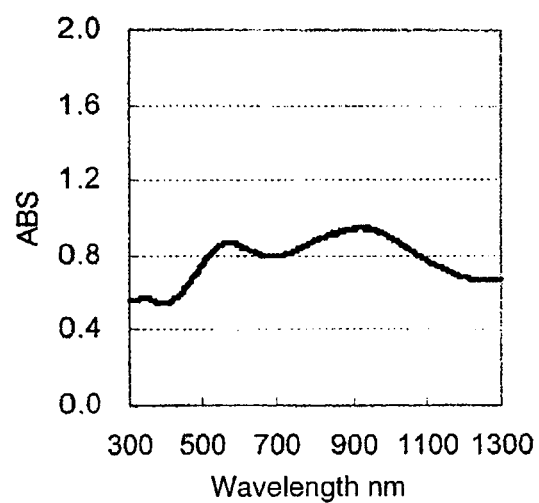
FIG. 1 illustrates UV-Vis-NIR analysis results of polymer (39) obtained in Example 5.

The polythiophene of the present invention is characterized by comprising at least one type of structural units selected from the group consisting of structural units represented by the above formula (1), structural units represented by the above formula (2), structural units represented by the above formula (3), structural units represented by the above formula (4), structural units represented by the above formula (5) and structural units represented by the above formula (6). Here, the structural unit represented by the above formula (2) represents a doped state of the structural unit represented by the above formula (1), the structural unit represented by the above formula (4) represents a doped state of the structural unit represented by the above formula (3), and the structural unit represented by the above formula (6) represents a doped state of the structural unit represented by the above formula (5).

The dopants which cause insulator-metal transition by doping are classified into acceptors and donors. The former enter into the vicinity of a polymer chain of the electrically conductive polymer by doping and deprive the conjugated system of the main chain of high electrons. As a result, positive charge (positive holes, holes) is injected into the main chain, and accordingly, the acceptors are also called p-type dopants. Specifically, a halogen ($Br_2$, $I_2$ or $Cl_2$), a Lewis acid ($BF_3$, $PF_5$ or $AsF_5$), a protonic acid ($H_2SO_4$, HCl or $CF_3SO_3H$), a transition metal halide ($FeCl_3$) or an organic material (TCNQ) may, for example, be mentioned.

Further, the latter impart electrons to the conjugated system of the main chain on the contrary, and the electrons move in the conjugated system of the main chain, and accordingly, the donors are also called n-type dopants. Specifically, an alkali metal (Li, Na, K or Cs) or an alkyl ammonium ion may, for example, be mentioned.

The dopant in the present invention is a sulfo group or a sulfonate group bonded into the polymer molecule by a covalent bond, and is a p-type dopant. Such a polymer which develops electrical conductivity without adding a dopant from outside is called a self-doping polymer.

First, a polythiophene (A) containing at least one type of structural units selected from the group consisting of structural units represented by the above formula (1) and structural units represented by the above formula (2) will be described.

In the above formula (1), $R^1$, M, X, n and m are as defined in the above formula (15). That is, $R^1$ is a hydrogen atom, a $C_{1-6}$ alkyl group or $C_{6-20}$ aryl group which may have a substituent, or —X—$SO_3$M. X is a $C_{1-6}$ alkylene group or $C_{6-20}$ arylene group which may have a substituent. M is a hydrogen atom, an alkali metal selected from the group consisting of Li, Na and K, $NH(R^2)_3$ or $HNC_5H_5$. $R^2$ is each independently a hydrogen atom or a $C_{1-6}$ alkyl group which may have a substituent. m is an integer of from 0 to 3, and n is an integer of from 0 to 12, provided that n+m≥1.

Further, in the above formula (2), $R^1$, X, n and m are as defined in the above formula (1).

The polythiophene (A) in the present invention specifically preferably contains at least one type of structural units selected from the group consisting of structural units represented by the above formula (7), structural units represented by the above formula (8), structural units represented by the above formula (9), structural units represented by the above formula (10), structural units represented by the above formula (11) and structural units represented by the above formula (12).

In the above formula (7), $R^3$, M, n and l are as defined in the above formula (18). That is, $R^3$ is a hydrogen atom, a $C_{1-6}$ alkyl group or $C_{6-20}$ aryl group which may have a substituent, or —$(CH_2)_l$—$SO_3$M, M is a hydrogen atom, an alkali metal selected from the group consisting of Li, Na and K, $NH(R^2)_3$ or $HNC_5H_5$. $R^2$ is each independently a hydrogen atom or a $C_{1-6}$ alkyl group which may have a substituent. l is an integer of from 1 to 6. n is an integer of from 0 to 12.

Further, in the above formula (8), $R^3$, n and l are as defined in the above formula (7). The structural unit represented by the above formula (8) represents a doped state of the structural unit represented by the above formula (7).

In the above formula (9), $R^4$, Ar, M and n are as defined in the above formula (19). That is, $R^4$ is a hydrogen atom, a $C_{1-6}$ alkyl group or $C_{6-20}$ aryl group which may have a substituent, or —Ar—$SO_3$M. M is a hydrogen atom, an alkali metal selected from the group consisting of Li, Na and K, $NH(R^2)_3$ or $HNC_5H_5$. $R^2$ is each independently a hydrogen atom, or a $C_{1-6}$ alkyl group which may have a substituent. Ar is a $C_{6-20}$ arylene group which may have a substituent. n is an integer of from 0 to 12.

Further, in the above formula (10), $R^4$, Ar and n are as defined in the above formula (9). The structural unit represented by the above formula (10) represents a doped state of the structural unit represented by the above formula (9).

In the above formula (11), M and n are as defined in the above formula (20). That is, M is a hydrogen atom, an alkali metal selected from the group consisting of Li, Na and K, $NH(R^2)_3$ or $HNC_5H_5$. $R^2$ is each independently a hydrogen atom or a $C_{1-6}$ alkyl group which may have a substituent. n is an integer of from 0 to 12.

Further, in the above formula (12), n is as defined in the above formula (11). The structural unit represented by the above formula (12) represents a doped state of the structural unit represented by the above formula (11).

Now, a polythiophene (B) containing at least one type of structural units selected from the group consisting of structural units represented by the above formula (3) and structural units represented by the above formula (4) will be described.

In the above formula (3), Ar, X, M, n, m and l are as defined in the above formula (16). That is, Ar is a $C_{6-20}$ arylene group which may have a substituent. X is a $C_{1-6}$ alkylene group which may have a substituent. M is a hydrogen atom, an alkali metal selected from the group consisting of Li, Na and K, $NH(R^1)_3$ or $HNC_5H_5$. $R^1$ is each independently a hydrogen atom or a $C_{1-6}$ alkyl group which may have a substituent. n is an integer of from 0 to 6. m is an integer of 0 or 1. l is an integer of from 1 to 4.

Further, in the above formula (4), Ar, X, n, m and l are as defined in the above formula (3).

The polythiophene in the present invention specifically preferably contains at least one type of structural units selected from the group consisting of structural units represented by the above formula (13) and structural units represented by the above formula (14).

In the above formula (13), $R^2$, X, M, n, m and l are as defined in the above formula (21). That is, M is a hydrogen atom, an alkali metal selected from the group consisting of Li, Na and K, $NH(R^1)_3$ or $HNC_5H_5$. $R^1$ is each independently a hydrogen atom or a $C_{1-6}$ alkyl group which may have a substituent. $R^2$ is a hydrogen atom, or a $C_{1-6}$ alkyl group or alkoxy group which may have a substituent. X is a $C_{1-6}$ alkylene group which may have a substituent. n is an integer of from 0 to 6. m is an integer of 0 or 1. l is an integer of from 1 to 4.

Further, in the above formula (14), $R^2$, X, n, m and l are as defined in the above formula (13). The structural unit represented by the above formula (14) represents a doped state of the structural unit represented by above formula (13).

Considering the application to a water-soluble electrically conductive polymer, more preferred is a polythiophene containing the structural units represented by the above formula (13) or the structural units represented by the above formula (14), wherein $R^2$ is a hydrogen atom and l=1.

Now, a polythiophene (C) containing at least one type of structural units selected from the group consisting of structural units represented by the above formula (5) and structural units represented by the above formula (6) will be described.

In the above formulae (5) and (6), R is a $C_{1-6}$ linear or branched alkyl group or a fluorine atom. The $C_{1-6}$ linear or branched alkyl group may, for example, be a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a cyclopentyl group, a n-hexyl group, a 2-ethylbutyl group, a cyclohexyl group or a n-octyl group.

In the above formula (5), M is a hydrogen atom, an alkali metal selected from the group consisting of Li, Na and K, $NH(R^1)_3$ or $HNC_5H_5$. On that occasion, $R^1$ is each independently a hydrogen atom or a $C_{1-6}$ alkyl group which may have a substituent. The substituent $R^1$ may be the same as the above substituent R, and is more preferably a hydrogen atom or a methyl group. Further, in a case where $R^1$ is an alkyl group which has a substituent, the substituent may, for example, be a $C_{1-6}$ alkyl group or alkoxy group, a $C_{1-20}$ aryl group, a hydroxy group, an amino group or a carboxy group, and is more preferably an alkyl group having a hydroxy group, such as a 2-hydroxyethyl group, a 3-hydroxypropyl group, a 2-hydroxypropyl group or a 2,3-dihydroxypropyl group.

The weight average molecular weight of the polythiophene of the present invention is not particularly limited, and is usually within a range of from 1,000 to 1,000,000 as calculated as polystyrene sulfonic acid, and is preferably within a range of from 1,000 to 200,000 for the application to a water-soluble electrically conductive polymer. With a view to removing unreacted monomers, low molecular weight impurities and inorganic salts from the polymer, it is more preferably within a range of from 3,500 to 100,000.

By forming the polythiophene of the present invention into an aqueous solution, processing for various applications as a water-soluble electrically conductive polymer aqueous solution will easily be carried out. A method for preparing a water-soluble electrically conductive polymer aqueous solution is not particularly limited, and the aqueous solution can be prepared by mixing the polymer with water and dissolving it at room temperature or with heating (preferably at most 100° C.). On that occasion, a conventional mixing and dissolution operation by a stirrer chip or an agitating blade may be employed, or as another method, ultrasonic irradiation or homogenization (for example, use of a mechanical homogenizer, an ultrasonic homogenizer, a high pressure homogenizer or the like) may be carried out. In the case of carrying out homogenization, it is preferably carried out under cooling, so as to prevent heat deterioration of the polymer.

The concentration of the polythiophene in the water-soluble electrically conductive polymer aqueous solution is not particularly limited, and is usually at most 50 wt %, preferably at most 20 wt %, and from the viewpoint of the viscosity, more preferably at most 10 wt %. It is particularly preferably from 0.01 to 10 wt %.

In the present invention, water solubility sufficient for processing for various applications, means water solubility to such an extent that of a polymer aqueous solution having a concentration of at most 10 wt % prepared at room temperature or with heating, the particle size (D50) measured by a particle size distribution measuring apparatus is at most 20 nm, and such an aqueous solution passes through a 0.05 μm filter.

Further, in the present invention, a favorable electrical conductivity means an electrical conductivity with an electric conductivity (electrical conductivity) in a film state of at least $10^{-1}$ S/cm.

Now, the method for producing the polythiophene of the present invention will be described.

The method for producing the polythiophene of the present invention is characterized by polymerizing at least one thiophene compound selected from the group consisting of a thiophene compound represented by the above formula (15), a thiophene compound represented by the above formula (16) and a thiophene compound represented by the above formula (17) in water or an alcohol solvent in the presence of an oxidizing agent.

Specifically, by polymerizing at least one thiophene compound selected from the group consisting of a thiophene compound represented by the above formula (15) in water or an alcohol solvent in the presence of an oxidizing agent, the polythiophene (A) of the present invention is obtained.

Further, by polymerizing at least one thiophene compound selected from the group consisting of a thiophene compound represented by the above formula (16) in water or an alcohol solvent in the presence of an oxidizing agent, the polythiophene (B) of the present invention is obtained.

Still further, by polymerizing at least one thiophene compound selected from the group consisting of a thiophene compound represented by the above formula (17) in water or an alcohol solvent in the presence of an oxidizing agent, the polythiophene (C) of the present invention is obtained.

The solvent used in this polymerization reaction is water or an alcohol solvent. Water is not limited so long as it is pure water, and it may be distilled water or deionized water. The alcohol solvent may be an alcohol such as methanol, ethanol, propanol or butanol. Such an alcohol solvent may be used alone or in combination with water. In the present invention, preferred is water or methanol, more preferred is water. Further, the solvent may be degassed or replaced with an inert gas such as nitrogen.

The amount of the solvent used in this polymerization reaction is not particularly limited so long as the thiophene compound used as a material is dissolved in the solvent, however, it is preferably from 0.1 to 100 times, more preferably from 0.1 to 50 times the weight of the thiophene compound charged.

The oxidizing agent used in this polymerization reaction is not particularly limited so long as it makes oxidative polymerization by an oxidative dehydrogenation reaction proceed, and it may, for example, be a persulfate, an iron (III) salt, hydrogen peroxide, a permanganate, a dichromate, cerium(IV) sulfate or oxygen, and they may be used alone or as a mixture of two or more.

Here, the persulfate may, for example, be specifically persulfuric acid, ammonium persulfate, sodium persulfate or potassium persulfate.

Further, the iron (III) salt may, for example, be specifically $FeCl_3$, $Fe_2(SO_4)_3$, iron perchlorate or iron(III) p-toluenesulfonate. They may be either an anhydride or a hydrate.

Further, the permanganate may, for example, be specifically sodium permanganate, potassium permanganate or magnesium permanganate.

Further, the dichromate may, for example, be specifically ammonium dichromate or potassium dichromate.

Among such oxidizing agents, preferred is an iron (III) salt or a combination of a persulfate and an iron (III) salt. The iron (III) salt is preferably $FeCl_3$ or $Fe_2(SO_4)_3$.

The amount of the oxidizing agent used in this polymerization reaction is not particularly limited, and is preferably within a range of from 1 to 50 molar times, more preferably from 1 to 20 molar times to the number of moles of the thiophene compound used as a material charged.

In a case where the oxidizing agent used in this polymerization reaction is, for example, an iron (III) salt alone, it is preferably used in such an amount that the amount of the iron (III) salt is at least equimolar to the number of moles of the thiophene compound used as a material charged, and the iron concentration to the solvent is at least 10 wt %, to carry out polymerization. From the viewpoint of doping required to develop more favorable electrical conductivity, the iron concentration to the solvent is more preferably at least 20 wt %. "The iron concentration" here means a value represented by iron salt/(iron salt+water)×100 (wt %), and the iron salt is calculated as an anhydride. Further, in a case where the oxidizing agent used in this polymerization reaction is, for example, a combination of a persulfate and an iron (III) salt, the amount of the oxidizing agent is such an amount that the amount of the persulfate is within a range of from 0.5 to 20 molar times, and the amount of the Fe (III) salt is within a range of from 0.01 to 10 molar times, to the number of moles of the thiophene compound used as a material charged. More preferably, the amount of the persulfate is within a range of from 1.5 to 10 molar times, and the amount of the Fe (III) salt is within a range of from 0.05 to 5 molar times.

The pressure in this polymerization reaction may be any of normal pressure, reduced pressure and elevated pressure.

The reaction atmosphere of this polymerization reaction may be the air or an inert gas such as nitrogen or argon. It is more preferably inert gas.

The reaction temperature of this polymerization reaction is not particularly limited so long as the thiophene compound used as a material undergoes oxidative polymerization, and is preferably from −10 to 150° C., more preferably from 20 to 100° C.

The reaction time of this polymerization reaction is not particularly limited so long as the oxidative polymerization of the thiophene compound used as a material sufficiently proceeds, and is preferably from 0.5 to 200 hours, more preferably from 0.5 to 80 hours.

The reaction method of this polymerization reaction is not particularly limited, and for example, in a case where the oxidizing agent used in this polymerization reaction is an iron (III) salt alone, the thiophene compound used as a material is formed into an aqueous solution, and a solid or an aqueous solution of the oxidizing agent may be dropwise added to the aqueous solution all at once or slowly, or the aqueous solution of the thiophene compound may be dropwise added to a solid or an aqueous solution of the oxidizing agent all at once or slowly. Further, in the case of a combination of a persulfate and an iron (III) salt, the persulfate and the iron (III) salt as a solid or an aqueous solution may be simultaneously or sequentially added to the aqueous solution of the thiophene compound, or on the contrary, the aqueous solution of the thiophene compound may be added to an aqueous solution of the persulfate and the iron (III) salt.

The method for purifying the polythiophene of the present invention obtained by this polymerization reaction is not particularly limited, and for example, washing with a solvent, re-precipitation, centrifugal sedimentation, ultrafiltration, dialysis or ion exchange resin treatment may be mentioned. They may be conducted alone or in combination.

For example, a typical method for isolating and purifying the polythiophene of the present invention is as follows.

First, the polymer aqueous solution after the polymerization reaction is added to a poor solvent such as acetone and the polymer is precipitated, and then the polymer obtained by filtration under reduced pressure is washed with the poor solvent until the filtrate becomes colorless and transparent. If this polymer contains a Fe salt which is insoluble in water, the polymer is preferably once added to a sodium hydroxide aqueous solution to be converted to a Na salt-form polymer which is soluble in water.

Then, the polymer is added to a poor solvent such as an alcohol and the polymer is precipitated and at the same time, an alkali content is removed, and a solid obtained by filtration under reduced pressure is washed with a poor solvent such as an alcohol. Then, the solid is washed with a poor solvent such as acetone, to obtain a Na salt-form polymer.

In a case where the obtained Na salt-form polymer is continuously converted to a H-form polymer, it is treated with a cation exchange resin. As a treatment method, for example, a method of passing an aqueous solution of the obtained Na salt-form polymer through a column packed with a cation exchange resin, or a body feed method of adding a cation exchange resin to the aqueous solution, may, for example, be mentioned. In such a case, it is preferred to remove the cation exchange resin e.g. by filter paper after the treatment. The aqueous solution thus obtained is roughly concentrated, and the concentrate is added to a poor solvent such as acetone to precipitate a solid, and the solid obtained by filtration under reduced pressure is thoroughly washed with the poor solvent and dried under reduced pressure to obtain a H-form polymer.

Further, in a case where a salt with an amine is to be formed, to an aqueous solution of the H-form polymer, an amine as it is undiluted, in the form of an aqueous solution or as diluted with a proper solvent is added, whereby the H-form polymer can easily be converted to an amine salt-form polymer. For example, in the case of treatment with ammonia water, the reaction liquid is roughly concentrated, and the resulting aqueous solution is added to a poor solvent such as acetone to precipitate a polymer, and a solid obtained by filtration under reduced pressure is washed with the poor solvent and dried under reduced pressure to obtain an ammonium salt-form polymer.

In each step of treatment after polymerization, as the case requires, centrifugal sedimentation or homogenization may be carried out, whereby the filtration efficiency may be improved. Further, in a case where a persulfate is used as the polymerization oxidizing agent, to remove the inorganic salt, ultrafiltration or dialysis, or cation/anion exchange resin mixing treatment may be carried out.

Now, the thiophene compound (monomer) used as a material in the method for producing the polythiophene of the present invention will be described.

First, the thiophene compound represented by the above formula (15) will be described.

In the above formula (15), $R^1$ is a hydrogen atom, a $C_{1-6}$ alkyl group or $C_{6-20}$ aryl group which may have a substituent, or —X—$SO_3$M. In a case where $R^1$ is an alkyl group or aryl group which has a substituent, the substituent may, for example, be a $C_{1-6}$ alkyl group or alkoxy group, a $C_{6-20}$ aryl group, a hydroxy group, an amino group or a carboxy group.

The substituent $R^1$ in the above formula (15) is not particularly limited so long as it meets the above definition, and may, for example, be a hydrogen atom; a $C_{1-6}$ alkyl group such as a methyl group, an ethyl group, a n-propyl group, an isopropyl group, a n-butyl group, an isobutyl group, a sec-methyl group, a tert-butyl group, a n-pentyl group, an isopentyl group, a neopentyl group, a tert-pentyl group, a cyclopentyl group, a n-hexyl group, a 2-ethylbutyl group, a 3,3-dimethylbutyl group, a cyclohexyl group, a n-heptyl group, a cyclohexylmethyl group, a n-octyl group or a trifluoromethyl group; a $C_{6-20}$ aryl group such as a phenyl group, a methylphenyl group, a methoxyphenyl group, a hydroxyphenyl group, an aminophenyl group, a trifluoromethylphenyl group, a naphthyl group or a biphenyl group; or —X—$SO_3$M.

Among them, $R^1$ is more preferably a hydrogen atom, a methyl group or —X—$SO_3$M.

In the above formula (15), X is a $C_{1-6}$ alkylene group or $C_{6-20}$ arylene group which may have a substituent. In a case where X is an alkylene group or arylene group which has a substituent, the substituent may, for example, be a $C_{1-6}$ alkyl group or alkoxy group, a $C_{6-20}$ aryl group, a hydroxy group, an amino group or a carboxy group.

X in the above formula (15) is not particularly limited so long as it meets the above definition and may, for example, be methylene, dimethylene, trimethylene, tetramethylene, hexamethylene, phenylene, biphenylene, naphthylene or anthrylene.

Among them, X is more preferably dimethylene, trimethylene, tetramethylene or phenylene.

In the above formula (15), n is an integer of from 0 to 12. n is preferably an integer of from 0 to 6.

In the above formula (15), m is an integer of from 0 to 3.

In the above formula (15), M is a hydrogen atom, an alkali metal selected from the group consisting of Li, Na and K, $NH(R^2)_3$ or $HNC_5H_5$.

$R^2$ is each independently a hydrogen atom or a $C_{1-6}$ alkyl group which may have a substituent. The substituent $R^2$ may be the same as $R^1$ and is more preferably a hydrogen atom or a methyl group. In a case where $R^2$ is an alkyl group which has a substituent, the substituent may, for example, be a $C_{1-6}$ alkyl group or alkoxy group, a $C_{6-20}$ aryl group, a hydroxy group, an amino group or a carboxy group.

The compound represented by the above formula (15) may, for example, be specifically as follows.

N-(2,3-dihydro-thieno[3,4-b][1,4]dioxin-2-ylmethyl)-2-aminoethanesulfonic acid, sodium N-(2,3-dihydro-thieno[3,4-b][1,4]dioxin-2-ylmethyl)-2-aminoethanesulfonate, lithium N-(2,3-dihydro-thieno[3,4-b][1,4]dioxin-2-ylmethyl)-2-aminoethanesulfonate, potassium N-(2,3-dihydro-thieno[3,4-b][1,4]dioxin-2-ylmethyl)-2-aminoethanesulfonate, ammonium N-(2,3-dihydro-thieno[3,4-b][1,4]dioxin-2-ylmethyl)-2-aminoethanesulfonate, triethylammonium N-(2,3-dihydro-thieno[3,4-b][1,4]dioxin-2-ylmethyl)-2-aminoethanesulfonate, pyridinium N-(2,3-dihydro-thieno[3,4-b][1,4]dioxin-2-ylmethyl)-2-aminoethanesulfonate, N-(2,3-dihydro-thieno[3,4-b][1,4]dioxin-2-ylmethyl)-bis(sodium 2-aminoethanesulfonate), N-(2,3-dihydro-thieno[3,4-b][1,4]dioxin-2-ylmethyl)-bis(potassium 2-aminoethanesulfonate), N-methyl-N-(2,3-dihydro-thieno[3,4-b][1,4]dioxin-2-ylmethyl)-2-aminoethanesulfonic acid, sodium N-methyl-N-(2,3-dihydro-thieno[3,4-b][1,4]dioxin-2-ylmethyl)-2-aminoethanesulfonate, lithium N-methyl-N-(2,3-dihydro-thieno[3,4-b][1,4]dioxin-2-ylmethyl)-2-aminoethanesulfonate, potassium N-methyl-N-(2,3-dihydro-thieno[3,4-b][1,4]dioxin-2-ylmethyl)-2-aminoethanesulfonate, ammonium N-methyl-N-(2,3-dihydro-thieno[3,4-b][1,4]dioxin-2-ylmethyl)-2-aminoethanesulfonate, triethylammonium N-methyl-N-(2,3-dihydro-thieno[3,4-b][1,4]dioxin-2-ylmethyl)-2-aminoethanesulfonate, pyridinium N-methyl-N-(2,3-dihydro-thieno[3,4-b][1,4]dioxin-2-ylmethyl)-2-aminoethanesulfonate, N-(2,3-dihydro-thieno[3,4-b][1,4]dioxin-2-ylmethyl)-3-aminopropanesulfonic acid, sodium N-(2,3-dihydro-thieno[3,4-b][1,4]dioxin-2-ylmethyl)-3-aminopropanesulfonate, lithium N-(2,3-dihydro-thieno[3,4-b][1,4]dioxin-2-ylmethyl)-3-aminopropanesulfonate, potassium N-(2,3-dihydro-thieno[3,4-b][1,4]dioxin-2-ylmethyl)-3-aminopropanesulfonate, ammonium N-(2,3-dihydro-thieno[3,4-b][1,4]dioxin-2-ylmethyl)-3-aminopropanesulfonate, triethylammonium N-(2,3-dihydro-thieno[3,4-b][1,4]dioxin-2-ylmethyl)-3-aminopropanesulfonate, pyridinium N-(2,3-dihydro-thieno[3,4-b][1,4]dioxin-2-ylmethyl)-2-aminopropanesulfonate, pyridinium N-(2,3-dihydro-thieno[3,4-b][1,4]dioxin-2-ylmethyl)-3-aminopropanesulfonate, N-(2,3-dihydro-thieno[3,4-b][1,4]dioxin-2-ylmethyl)-bis(sodium 3-aminopropanesulfonate), N-(2,3-dihydro-thieno[3,4-b][1,4]dioxin-2-ylmethyl)-bis(potassium 3-aminopropanesulfonate), N-methyl-N-(2,3-dihydro-thieno[3,4-b][1,4]dioxin-2-ylmethyl)-3-aminopropanesulfonate, sodium N-methyl-N-(2,3-dihydro-thieno[3,4-b][1,4]dioxin-2-ylmethyl)-3-aminopropanesulfonate, lithium N-methyl-N-(2,3-dihydro-thieno[3,4-b][1,4]dioxin-2-ylmethyl)-3-aminopropanesulfonate, potassium N-methyl-N-(2,3-dihydro-thieno[3,4-b][1,4]dioxin-2-ylmethyl)-3-aminopropanesulfonate, ammonium N-methyl-N-(2,3-dihydro-thieno[3,4-b][1,4]dioxin-2-ylmethyl)-3-aminopropanesulfonate, triethylammonium N-methyl-N-(2,3-dihydro-thieno[3,4-b][1,4]dioxin-2-ylmethyl)-3-aminopropanesulfonate, pyridinium N-methyl-N-(2,3-dihydro-thieno[3,4-b][1,4]dioxin-2-ylmethyl)-3-aminopropanesulfonate, N-(2,3-dihydro-thieno[3,4-b][1,4]dioxin-2-ylmethyl)-4-aminobutanesulfonic acid, sodium N-(2,3-dihydro-thieno[3,4-b][1,4]dioxin-2-ylmethyl)-4-aminobutanesulfonate, lithium N-(2,3-dihydro-thieno[3,4-b][1,4]dioxin-2-ylmethyl)-4-aminobutanesulfonate, potassium N-(2,3-dihydro-thieno[3,4-b][1,4]dioxin-2-ylmethyl)-4-aminobutanesulfonate, ammonium N-(2,3-dihydro-thieno[3,4-b][1,4]dioxin-2-ylmethyl)-4-aminobutanesulfonate, triethylammonium N-(2,3-dihydro-thieno[3,4-b][1,4]dioxin-2-ylmethyl)-4-aminobutanesulfonate, pyridinium N-(2,3-dihydro-thieno[3,4-b][1,4]dioxin-2-ylmethyl)-4-aminobutanesulfonate, N-(2,3-dihydro-thieno[3,4-b][1,4]dioxin-2-ylmethyl)-bis(sodium 4-aminobutanesulfonate), N-(2,3-dihydro-thieno[3,4-b][1,4]dioxin-2-ylmethyl)-bis(potassium 4-aminobutanesulfonate), N-methyl-N-(2,3-dihydro-thieno[3,4-b][1,4]dioxin-2-ylmethyl)-4-aminobutanesulfonic acid, sodium N-methyl-N-(2,3-dihydro-thieno[3,4-b][1,4]dioxin-2-ylmethyl)-4-aminobutanesulfonate, lithium N-methyl-N-(2,3-dihydro-thieno[3,4-b][1,4]dioxin-2-ylmethyl)-4-aminobutanesulfonate, potassium N-methyl-N-(2,3-dihydro-thieno[3,4-b][1,4]dioxin-2-ylmethyl)-4-aminobutanesulfonate, ammonium N-methyl-N-(2,3-dihydro-thieno[3,4-b][1,4]dioxin-2-ylmethyl)-4-aminobutanesulfonate, triethylammonium N-methyl-N-(2,3-dihydro-thieno[3,4-b][1,4]dioxin-2-ylmethyl)-4-aminobutanesulfonate, pyridinium N-methyl-N-(2,3-dihydro-thieno[3,4-b][1,4]dioxin-2-ylmethyl)-4-aminobutanesulfonate, N-(2,3-dihydro-thieno[3,4-b][1,4]dioxin-2-ylmethyl)-4-aminobenzenesulfonic acid, sodium N-(2,3-dihydro-thieno[3,4-b][1,4]dioxin-2-ylmethyl)-4-aminobenzenesulfonate, lithium N-(2,3-dihydro-thieno[3,4-b][1,4]dioxin-2-ylmethyl)-4-aminobenzenesulfonate, potassium N-(2,3-dihydro-thieno[3,4-b][1,4]dioxin-2-ylmethyl)-4-aminobenzenesulfonate, ammonium N-(2,3-dihydro-thieno[3,4-b][1,4]dioxin-2-ylmethyl)-4-aminobenzenesulfonate, triethylammonium N-(2,3-dihydro-thieno[3,4-b][1,4]dioxin-2-ylmethyl)-4-aminobenzenesulfonate, pyridinium N-(2,3-dihydro-thieno[3,4-b][1,4]dioxin-2-ylmethyl)-4-aminobenzenesulfonate, N-(2,3-dihydro-thieno[3,4-b][1,4]dioxin-2-ylmethyl)-bis(sodium 4-aminobenzenesulfonate), N-(2,3-dihydro-thieno[3,4-b][1,4]dioxin-2-ylmethyl)-bis(potassium 4-aminobenzenesulfonate), N-methyl-N-(2,3-dihydro-thieno[3,4-b][1,4]dioxin-2-ylmethyl)-4-aminobenzenesulfonic acid, sodium N-methyl-N-(2,3-dihydro-thieno[3,4-b][1,4]dioxin-2-ylmethyl)-4-aminobenzenesulfonate, lithium N-methyl-N-(2,3-dihydro-thieno[3,4-b][1,4]dioxin-2-ylmethyl)-4-aminobenzenesulfonate, potassium N-methyl-N-(2,3-dihydro-thieno[3,4-b][1,4]dioxin-2-ylmethyl)-4-aminobenzenesulfonate, ammonium N-methyl-N-(2,3-dihydro-thieno[3,4-b][1,4]dioxin-2-ylmethyl)-4-aminobenzenesulfonate, triethylammonium N-methyl-N-(2,3-dihydro-thieno[3,4-b][1,4]dioxin-2-ylmethyl)-4-aminobenzenesulfonate, pyridinium N-methyl-N-(2,3-dihydro-thieno[3,4-b][1,4]dioxin-2-ylmethyl)-4-aminobenzenesulfonate, N-(2,3-dihydro-thieno[3,4-b][1,4]dioxin-2-ylmethyl)-3-aminobenzenesulfonic acid, sodium N-(2,3-dihydro-thieno[3,4-b][1,4]dioxin-2-ylmethyl)-3-aminobenzenesulfonate, lithium N-(2,3-dihydro-thieno[3,4-b][1,4]dioxin-2-ylmethyl)-3-aminobenzenesulfonate, potassium N-(2,3-dihydro-thieno[3,4-b][1,4]dioxin-2-ylmethyl)-3-aminobenzenesulfonate, ammonium N-(2,3-dihydro-thieno[3,4-b][1,4]dioxin-2-ylmethyl)-3-aminobenzenesulfonate, triethylammonium N-(2,3-dihydro-thieno[3,4-b][1,4]dioxin-2-ylmethyl)-3-aminobenzenesulfonate, pyridinium N-(2,3-dihydro-thieno[3,4-b][1,4]dioxin-2-ylmethyl)-3-aminobenzenesulfonate, N-(2,3-dihydro-thieno[3,4-b][1,4]dioxin-2-ylmethyl)-bis(sodium 3-aminobenzenesulfonate), N-(2,3-dihydro-thieno[3,4-b][1,4]dioxin-2-ylmethyl)-bis(potassium 3-aminobenzenesulfonate), N-methyl-N-(2,3-dihydro-thieno[3,4-b][1,4]dioxin-2-ylmethyl)-3-aminobenzenesulfonic acid, sodium N-methyl-N-(2,3-dihydro-thieno[3,4-b][1,4]dioxin-2-ylmethyl)-3-aminobenzenesulfonate, lithium N-methyl-N-(2,3-dihydro-thieno[3,4-b][1,4]dioxin-2-ylmethyl)-3-aminobenzenesulfonate, potassium N-methyl-N-(2,3-dihydro-thieno[3,4-b][1,4]dioxin-2-ylmethyl)-3-aminobenzenesulfonate, ammonium N-methyl-N-(2,3-dihydro-thieno[3,4-b][1,4]dioxin-2-ylmethyl)-3-aminobenzenesulfonate, triethylammonium N-methyl-N-(2,3-dihydro-thieno[3,4-b][1,4]dioxin-2-ylmethyl)-3-aminobenzenesulfonate, pyridinium N-methyl-N-(2,3-dihydro-thieno[3,4-b][1,4]dioxin-2-ylmethyl)-3-aminobenzenesulfonate, N-(2,3-dihydro-thieno[3,4-b][1,4]dioxin-2-yl)-2-aminoethanesulfonic acid, sodium N-(2,3-dihydro-thieno[3,4-b][1,4]dioxin-2-yl)-2-aminoethanesulfonate, lithium N-(2,3-dihydro-thieno[3,4-b][1,4]dioxin-2-yl)-2-aminoethanesulfonate, potassium N-(2,3-dihydro-thieno[3,4-b][1,4]dioxin-2-yl)-2-aminoethanesulfonate, ammonium N-(2,3-dihydro-thieno[3,4-b][1,4]dioxin-2-yl)-2-aminoethanesulfonate, triethylammonium N-(2,3-dihydro-thieno[3,4-b][1,4]dioxin-2-yl)-2-aminoethanesulfonate, pyridinium N-(2,3-dihydro-thieno[3,4-b][1,4]dioxin-2-yl)-2-aminoethanesulfonate, N-methyl-N-(2,3-dihydro-thieno[3,4-b][1,4]dioxin-2-yl)-2-aminoethanesulfonic acid, sodium N-methyl-N-(2,3-dihydro-thieno[3,4-b][1,4]dioxin-2-yl)-2-aminoethanesulfonate, lithium N-methyl-N-(2,3-dihydro-thieno[3,4-b][1,4]dioxin-2-yl)-2-aminoethanesulfonate, potassium N-methyl-N-(2,3-dihydro-thieno[3,4-b][1,4]dioxin-2-yl)-2-aminoethanesulfonate, ammonium N-methyl-N-(2,3-dihydro-thieno[3,4-b][1,4]dioxin-2-yl)-2-aminoethanesulfonate, triethylammonium N-methyl-N-(2,3-dihydro-thieno[3,4-b][1,4]dioxin-2-yl)-2-aminoethanesulfonate, pyridinium N-methyl-N-(2,3-dihydro-thieno[3,4-b][1,4]dioxin-2-yl)-2-aminoethanesulfonate, N-(2,3-dihydro-thieno[3,4-b][1,4]dioxin-2-yl)-3-aminopropanesulfonate, sodium N-(2,3-dihydro-thieno[3,4-b][1,4]dioxin-2-yl)-3-aminopropanesulfonate, lithium N-(2,3-dihydro-thieno[3,4-b][1,4]dioxin-2-yl)-3-aminopropanesulfonate, potassium N-(2,3-dihydro-thieno[3,4-b][1,4]dioxin-2-yl)-3-aminopropanesulfonate, ammonium N-(2,3-dihydro-thieno[3,4-b][1,4]dioxin-2-yl)-3-aminopropanesulfonate, triethylammonium N-(2,3-dihydro-thieno[3,4-b][1,4]dioxin-2-yl)-3-aminopropanesulfonate, pyridinium N-(2,3-dihydro-thieno[3,4-b][1,4]dioxin-2-yl)-2-aminopropanesulfonate, pyridinium N-(2,3-dihydro-thieno[3,4-b][1,4]dioxin-2-yl)-3-aminopropanesulfonate, N-methyl-N-(2,3-dihydro-thieno[3,4-b][1,4]dioxin-2-yl)-3-aminopropanesulfonic acid, sodium N-methyl-N-(2,3-dihydro-thieno[3,4-b][1,4]dioxin-2-yl)-3-aminopropanesulfonate, lithium N-methyl-N-(2,3-dihydro-thieno[3,4-b][1,4]dioxin-2-yl)-3-aminopropanesulfonate, potassium N-methyl-N-(2,3-dihydro-thieno[3,4-b][1,4]dioxin-2-yl)-3-aminopropanesulfonate, ammonium N-methyl-N-(2,3-dihydro-thieno[3,4-b][1,4]dioxin-2-yl)-3-aminopropanesulfonate, triethylammonium N-methyl-N-(2,3- dihydro-thieno[3,4-b][1,4]dioxin-2-yl)-3-aminopropanesulfonate, pyridinium N-methyl-N-(2,3-dihydro-thieno[3,4-b][1,4]dioxin-2-yl)-3-aminopropanesulfonate, N-(2,3-dihydro-thieno[3,4-b][1,4]dioxin-2-yl)-3-aminobenzenesulfonic acid, sodium N-(2,3-dihydro-thieno[3,4-b][1,4]dioxin-2-yl)-3-aminobenzenesulfonate, lithium N-(2,3-dihydro-thieno[3,4-b][1,4]dioxin-2-yl)-3-aminobenzenesulfonate, potassium N-(2,3-dihydro-thieno[3,4-b][1,4]dioxin-2-yl)-3-aminobenzenesulfonate, ammonium N-(2,3-dihydro-thieno[3,4-b][1,4]dioxin-2-yl)-3-aminobenzenesulfonate, triethylammonium N-(2,3-dihydro-thieno[3,4-b][1,4]dioxin-2-yl)-3-aminobenzenesulfonate, pyridinium N-(2,3-dihydro-thieno[3,4-b][1,4]dioxin-2-yl)-3-aminobenzenesulfonate, N-methyl-N-(2,3-dihydro-thieno[3,4-b][1,4]dioxin-2-yl)-3-aminobenzenesulfonic acid, sodium N-methyl-N-(2,3-dihydro-thieno[3,4-b][1,4]dioxin-2-yl)-3-aminobenzenesulfonate, lithium N-methyl-N-(2,3-dihydro-thieno[3,4-b][1,4]dioxin-2-yl)-3-aminobenzenesulfonate, potassium N-methyl-N-(2,3-dihydro-thieno[3,4-b][1,4]dioxin-2-yl)-3-aminobenzenesulfonate, ammonium N-methyl-N-(2,3-dihydro-thieno[3,4-b][1,4]dioxin-2-yl)-3-aminobenzenesulfonate, triethylammonium N-methyl-N-(2,3-dihydro-thieno[3,4-b][1,4]dioxin-2-yl)-3-aminobenzenesulfonate, pyridinium N-methyl-N-(2,3-dihydro-thieno[3,4-b][1,4]dioxin-2-yl)-3-aminobenzenesulfonate, and the like.

Among them, the material monomer of the water-soluble electrically conductive polymer is preferably a compound represented by any one of the above formulae (18) to (20).

In the above formula (18), $R^3$ is a hydrogen atom, a $C_{1-6}$ alkyl group or $C_{6-20}$ aryl group which may have a substituent, or —(CH$_2$)$_l$—SO$_3$M. l is an integer of from 1 to 6. n and M are as defined in the above formula (15).

In the formula (19), $R^4$ is a hydrogen atom, a $C_{1-6}$ alkyl group which may have a substituent, a $C_{6-20}$ aryl group or —Ar—SO$_3$M. Ar is each independently a $C_{6-20}$ arylene group which may have a substituent. n and M are as defined in the above formula (15).

In a case where the substituent $R^3$ or $R^4$ is an alkyl group which has a substituent, the substituent may, for example, be a $C_{1-6}$ alkyl group or alkoxy group, a $C_{6-20}$ aryl group, a hydroxy group, an amino group or a carboxy group.

In the above formula (20), n and M are as defined in the formula (15).

The compound represented by the above formula (20) may, for example, be specifically as follows.

2,3-dihydro-thieno[3,4-b][1,4]dioxin-2-ylmethanesulfonic acid, lithium 2,3-dihydro-thieno[3,4-b][1,4]dioxin-2-ylmethanesulfonate, sodium 2,3-dihydro-thieno[3,4-b][1,4]dioxin-2-ylmethanesulfonate, potassium 2,3-dihydro-thieno[3,4-b][1,4]dioxin-2-ylmethanesulfonate, ammonium 2,3-dihydro-thieno[3,4-b][1,4]dioxin-2-ylmethanesulfonate, triethylammonium 2,3-dihydro-thieno[3,4-b][1,4]dioxin-2-ylmethanesulfonate, pyridinium 2,3-dihydro-thieno[3,4-b][1,4]dioxin-2-ylmethanesulfonate, 2-(2,3-dihydro-thieno[3,4-b][1,4]dioxin-2-yl)ethane-1-sulfonic acid, sodium 2-(2,3-dihydro-thieno[3,4-b][1,4]dioxin-2-yl)ethane-1-sulfonate, lithium 2-(2,3-dihydro-thieno[3,4-b][1,4]dioxin-2-yl)ethane-1-sulfonate, potassium 2-(2,3-dihydro-thieno[3,4-b][1,4]dioxin-2-yl)ethanesulfonate, ammonium 2-(2,3-dihydro-thieno[3,4-b][1,4]dioxin-2-yl)ethanesulfonate, triethylammonium 2-(2,3-dihydro-thieno[3,4-b][1,4]dioxin-2-yl)ethane-1-sulfonate, pyridinium 2-(2,3-dihydro-thieno[3,4-b][1,4]dioxin-2-yl)ethane-1-sulfonate, 3-(2,3-dihydro-thieno[3,4-b][1,4]dioxin-2-yl)propane-1-sulfonic acid, sodium 3-(2,3-dihydro-thieno[3,4-b][1,4]dioxin-2-yl)propane-1-sulfonate, lithium 3-(2,3-dihydro-thieno[3,4-b][1,4]dioxin-2-yl)propane-1-sulfonate, potassium 3-(2,3-dihydro-thieno[3,4-b][1,4]dioxin-2-yl)propane-1-sulfonate, ammonium 3-(2,3-dihydro-thieno[3,4-b][1,4]dioxin-2-yl)propane-1-sulfonate, triethylammonium 3-(2,3-dihydro-thieno[3,4-b][1,4]dioxin-2-yl)propane-1-sulfonate, pyridinium 3-(2,3-dihydro-thieno[3,4-b][1,4]dioxin-2-yl)propane-1-sulfonate, pyridinium 3-(2,3-dihydro-thieno[3,4-b][1,4]dioxin-2-yl)propane-1-sulfonate, 6-(2,3-dihydro-thieno[3,4-b][1,4]dioxin-2-yl)hexane-1-sulfonic acid, sodium 6-(2,3-dihydro-thieno[3,4-b][1,4]dioxin-2-yl)hexane-1-sulfonate, lithium 6-(2,3-dihydro-thieno[3,4-b][1,4]dioxin-2-yl)hexane-1-sulfonate, potassium 6-(2,3-dihydro-thieno[3,4-b][1,4]dioxin-2-yl)hexane-1-sulfonate, ammonium 6-(2,3-dihydro-thieno[3,4-b][1,4]dioxin-2-yl)hexane-1-sulfonate, triethylammonium 6-(2,3-dihydro-thieno[3,4-b][1,4]dioxin-2-yl)hexane-1-sulfonate, pyridinium 6-(2,3-dihydro-thieno[3,4-b][1,4]dioxin-2-yl)hexane-1-sulfonate, pyridinium 6-(2,3-dihydro-thieno[3,4-b][1,4]dioxin-2-yl)hexane-1-sulfonate, and the like.

The thiophene compound represented by any one of the above formulae (15) to (19) of the present invention is easily obtained by reacting a thiophene compound represented by the following formula (22) and a compound represented by the following formula (23) in a polar solvent in the presence of a base:

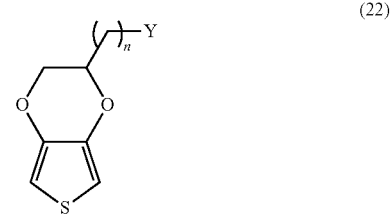

(22)

wherein Y is tosylate, mesylate, triflate, chloride, bromide or iodide, and n is an integer of from 0 to 12;

(23)

wherein $R^1$ is a hydrogen atom, a $C_{1-6}$ alkyl group or $C_{6-20}$ aryl group which may have a substituent, or —X—SO$_3$M, X is a $C_{1-6}$ alkylene group or $C_{6-20}$ arylene group which may have a substituent, M is a hydrogen atom, an alkali metal selected from the group consisting of Li, Na, and K, NH($R^2$)$_3$ or HNC$_5$H$_5$, and $R^2$ is each independently a hydrogen atom or a $C_{1-6}$ alkyl group which may have a substituent.

In the compound represented by the above formula (22), Y is tosylate, mesylate, triflate, chloride, bromide or iodide. n is as defined in the formula (15).

The compound represented by the above formula (22) may, for example, be specifically 2,3-dihydro-thieno[3,4-b][1,4]dioxin-2-ylmethyl chloride, 2,3-dihydro-thieno[3,4-b][1,4]dioxin-2-ylmethyl bromide, 2,3-dihydro-thieno[3,4-b][1,4]dioxin-2-ylmethyl iodide, 2,3-dihydro-thieno[3,4-b][1,4]dioxin-2-ylmethyl tosylate, 2,3-dihydro-thieno[3,4-b][1,4]dioxin-2-ylmethyl mesylate, 2,3-dihydro-thieno[3,4-b][1,4]dioxin-2-ylmethyl triflate, 2,3-dihydro-thieno[3,4-b][1,4]dioxin-2-ylmethyl chloride, 2,3-dihydro-thieno[3,4-b][1,4]

dioxin-2-ylethyl bromide, 2,3-dihydro-thieno[3,4-b][1,4]dioxin-2-ylethyl iodide, 2,3-dihydro-thieno[3,4-b][1,4]dioxin-2-ylethyl tosylate, 2,3-dihydro-thieno[3,4-b][1,4]dioxin-2-ylethyl mesylate, 2,3-dihydro-thieno[3,4-b][1,4]dioxin-2-ylethyl triflate, 2,3-dihydro-thieno[3,4-b][1,4]dioxin-2-ylpropyl chloride, 2,3-dihydro-thieno[3,4-b][1,4]dioxin-2-ylpropyl bromide, 2,3-dihydro-thieno[3,4-b][1,4]dioxin-2-ylpropyl iodide, 2,3-dihydro-thieno[3,4-b][1,4]dioxin-2-ylpropyl tosylate, 2,3-dihydro-thieno[3,4-b][1,4]dioxin-2-ylpropyl mesylate, or 2,3-dihydro-thieno[3,4-b][1,4]dioxin-2-ylpropyl triflate.

In the compound represented by the above formula (23), $R^1$, X and M are as defined in the above formula (15).

The compound represented by above formula (23) may, for example, be specifically 2-aminoethanesulfonic acid, sodium 2-aminoethanesulfonate, potassium 2-aminoethanesulfonate, lithium 2-aminoethanesulfonate, ammonium 2-aminoethanesulfonate, N-methyl-2-aminoethanesulfonate, sodium N-methyl-2-aminoethanesulfonate, potassium N-methyl-2-aminoethanesulfonate, lithium N-methyl-2-aminoethanesulfonate, ammonium N-methyl-2-aminoethanesulfonate, 3-aminopropanesulfonate, sodium 3-aminopropanesulfonate, potassium 3-aminopropanesulfonate, lithium 3-aminopropanesulfonate, ammonium 3-aminopropanesulfonate, N-methyl-3-aminopropanesulfonic acid, sodium N-methyl-3-aminopropanesulfonate, potassium N-methyl-3-aminopropanesulfonate, lithium N-methyl-3-aminopropanesulfonate, ammonium N-methyl-3-aminopropanesulfonate, 4-aminobutanesulfonic acid, sodium 4-aminobutanesulfonate, potassium 4-aminobutanesulfonate, lithium 4-aminobutanesulfonate, ammonium 4-aminobutanesulfonate, N-methyl-4-aminobutanesulfonic acid, sodium N-methyl-4-aminobutanesulfonate, potassium N-methyl-4-aminobutanesulfonate, lithium N-methyl-4-aminobutanesulfonate, or ammonium N-methyl-4-aminobutanesulfonate.

The polar solvent used in this reaction is not particularly limited so long as the reaction proceeds in it, and may, for example, be N,N-dimethylaminoformamide, N-methylformamide, N-methylpyrrolidone, N,N-dimethylacetamide, methanol, acetone or water. Among them, more preferred is N,N-dimethylformamide. They may be used alone or as mixed optionally.

The amount of the polar solvent used is not particularly limited so long as the compound represented by the above formula (22) and the compound represented by the above formula (23) as materials are dissolved in the polar solvent, and is preferably from 0.1 to 200 times, more preferably from 1 to 100 times the total weight of the compound represented by the above formula (22) and the compound represented by the above formula (23) charged.

The base used in this reaction is not particularly limited so long as the reaction proceeds, and may, for example, be sodium carbonate, potassium carbonate, cesium carbonate, sodium hydrogen carbonate, sodium hydride, lithium hydroxide, sodium hydroxide, potassium hydroxide, rubidium hydroxide, calcium hydroxide, ammonia water, pyridine, trimethylamine, triethylamine or tributylamine. Among them, more preferred is sodium carbonate or potassium carbonate.

The amount of the base used is preferably from 1 to 100 molar times, more preferably from 1 to 10 molar times, further preferably from 2 to 5 molar times to the total number of moles of the compound represented by the above formula (22) and the compound represented by the above formula (23).

The reaction temperature of this reaction is not particularly limited so long as the reaction proceeds, and is preferably from −20 to 200° C., more preferably from 30 to 180° C., further preferably from 50 to 120° C.

The reaction atmosphere of this reaction is preferably in the air or in nitrogen or argon, more preferably in nitrogen.

The reaction pressure of this reaction may be ordinary pressure or elevated pressure, preferably ordinary pressure.

The thiophene compound represented by the above formula (20) is easily obtained by reacting the thiophene compound represented by the above formula (22) with a sulfite in a water solvent.

The sulfite used in this reaction may, for example, be sodium sulfite, potassium sulfite or ammonium sulfite.

The amount of the sulfite used in this reaction is preferably from 0.5 to 50 molar times, more preferably from 1 to 3 molar times to the moles of the compound represented by the above formula (22) charged.

The amount of the water solvent used in this reaction may, for example, be such an amount that the thiophene compound and the sulfite are dissolved and is not particularly limited, and is preferably from 0.1 to 200 times, more preferably from 1 to 100 times the weight of the compound represented by the above formula (22) charged.

The temperature of this reaction is not particularly limited so long as the reaction proceeds, and is preferably from 0° C. to the reflux temperature (about 100° C.), more preferably from 50 to the reflux temperature (about 100° C.).

Another method to obtain the thiophene compound represented by the above formula (20) may, for example, be a method of reacting a thiophene compound represented by the following formula (22a) with a bisulfite in a mixed solvent of water and an alcohol in the presence of a radical initiator:

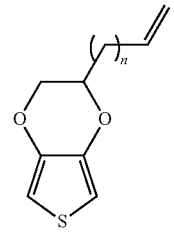

(22a)

The compound represented by the above formula (22a) may, for example, be specifically 2-(2,3-dihydro-thieno[3,4-b][1,4]dioxin-2-yl)-1-ethene, 3-(2,3-dihydro-thieno[3,4-b][1,4]dioxin-2-yl)-1-propene, 4-(2,3-dihydro-thieno[3,4-b][1,4]dioxin-2-yl)-1-butene, 6-(2,3-dihydro-thieno[3,4-b][1,4]dioxin-2-yl)-1-hexene, or 8-(2,3-dihydro-thieno[3,4-b][1,4]dioxin-2-yl)-1-octene.

The method and procedure of charge in this reaction are not particularly limited, and the thiophene compound represented by the above formula (20) may be obtained, for example, by dropwise adding a separately prepared aqueous solution containing a bisulfite and a small amount of a sulfite to an alcohol solution containing the thiophene compound represented by the above formula (22a) and a radical initiator, followed by reaction at room temperature or with heating.

The alcohol used in this reaction may, for example, be methanol, ethanol, propanol or butanol. Suitably, methanol or ethanol is used. Further, the amount of the alcohol used in this reaction may, for example, be such an amount that the thiophene compound represented by the above formula (22a) is dissolved or suspended and is not particularly limited, and is preferably from 0.1 to 200 times, more preferably from 1 to 100 times the weight of the compound represented by the above formula (22a) charged.

The amount of water used in this reaction may, for example, be such an amount that the bisulfite and a small amount of the sulfite are dissolved and is not particularly limited, and is preferably from 0.1 to 200 times, more preferably from 1 to 100 times the weight of the bisulfite charged.

The bisulfite used in this reaction may, for example, be sodium bisulfite, potassium bisulfite or ammonium bisulfite. Further, the amount of the bisulfite used in this reaction is preferably from 0.5 to 100 molar times, more preferably from 1 to 10 molar times to the thiophene compound represented by the above formula (22a).

The sulfite used in this reaction may, for example, be sodium sulfite, potassium sulfite or ammonium sulfite. Further, the amount of the sulfite used in this reaction is preferably from 0.0001 to 10 molar times, more preferably from 0.001 to 1 molar time to the moles of the compound represented by the above formula (22a) charged.

The temperature of this reaction is not particularly limited so long as the reaction proceeds, and is preferably from 0° C. to the reflux temperature (about 100° C.), more preferably from 50 to the reflux temperature (about 100° C.).

The reaction atmosphere of this reaction is preferably in the air or in nitrogen or argon, more preferably in nitrogen.

The reaction pressure of this reaction may be ordinary pressure or elevated pressure, preferably ordinary pressure.

The thiophene compound used as the material is more preferably one having water solubility to such an extent that it is dissolved in water at room temperature or with heating in an amount of at least 0.5 wt %.

Now, the thiophene represented by the above formula (16) will be described.

In the above formula (16), Ar is a $C_{6-20}$ arylene group which may have a substituent. In a case where Ar is an arylene group which has a substituent, the substituent may, for example, be a $C_{1-6}$ alkyl group or alkoxy group, a $C_{6-20}$ aryl group, a hydroxy group, an amino group or a carboxy group.

In the above formula (16), Ar is not particularly limited, and may, for example, be a phenylene group, a naphthylene group, a biphenylene group or an anthrylene group.

In the above formula (16), X is a $C_{1-6}$ alkylene group which may have a substituent.

In a case where X is an alkylene group which has a substituent, the substituent may, for example, be a $C_{1-6}$ alkyl group or alkoxy group, a $C_{6-20}$ aryl group, a hydroxy group, an amino group or a carboxy group.

In the above formula (16), X is not particularly limited and may, for example, be specifically a methylene group, a dimethylene group, a trimethylene group, a tetramethylene group or a hexamethylene group.

In the above formula (16), M is a hydrogen atom, an alkali metal selected from the group consisting of Li, Na and K, $NH(R^1)_3$ or $HNC_5H_5$.

Further, $R^1$ is each independently a hydrogen atom or a $C_{1-6}$ alkyl group which may have a substituent. The substituent $R^1$ is not particularly limited may and, for example, be a hydrogen atom or a $C_{1-6}$ alkyl group such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a cyclopentyl group, a n-hexyl group, a 2-ethylbutyl group, a cyclohexyl group or a n-octyl group. Preferred is a hydrogen atom, a methyl group, an ethyl group or a propyl group. Further, in a case where $R^1$ is an alkyl group which has a substituent, the substituent may, for example, be a $C_{1-6}$ alkyl group or alkoxy group, a $C_{1-20}$ aryl group, a hydroxy group, an amino group or a carboxy group.

In the above formula (16), n is an integer of from 0 to 6, m is an integer of 0 or 1, and l is an integer of from 1 to 4.

In the present invention, the compound represented by the above formula (16) may, for example, be specifically as follows.

O-(2,3-dihydro-thieno[3,4-b][1,4]dioxin-2-ylmethyl)-4-phenolsulfonic acid, sodium O-(2,3-dihydro-thieno[3,4-b][1,4]dioxin-2-ylmethyl)-4-phenolsulfonate, lithium O-(2,3-dihydro-thieno[3,4-b][1,4]dioxin-2-ylmethyl)-4-phenolsulfonate, potassium O-(2,3-dihydro-thieno[3,4-b][1,4]dioxin-2-ylmethyl)-4-phenolsulfonate, ammonium O-(2,3-dihydro-thieno[3,4-b][1,4]dioxin-2-ylmethyl)-4-phenolsulfonate, triethylammonium O-(2,3-dihydro-thieno[3,4-b][1,4]dioxin-2-ylmethyl)-4-phenolsulfonate, pyridinium O-(2,3-dihydro-thieno[3,4-b][1,4]dioxin-2-ylmethyl)-4-phenolsulfonate, O-(2,3-dihydro-thieno[3,4-b][1,4]dioxin-2-ylmethyl)-3-phenolsulfonic acid, sodium O-(2,3-dihydro-thieno[3,4-b][1,4]dioxin-2-ylmethyl)-3-phenolsulfonate, lithium O-(2,3-dihydro-thieno[3,4-b][1,4]dioxin-2-ylmethyl)-3-phenolsulfonate, potassium O-(2,3-dihydro-thieno[3,4-b][1,4]dioxin-2-ylmethyl)-3-phenolsulfonate, ammonium O-(2,3-dihydro-thieno[3,4-b][1,4]dioxin-2-ylmethyl)-3-phenolsulfonate, triethylammonium O-(2,3-dihydro-thieno[3,4-b][1,4]dioxin-2-ylmethyl)-3-phenolsulfonate, pyridinium O-(2,3-dihydro-thieno[3,4-b][1,4]dioxin-2-ylmethyl)-3-phenolsulfonate, O-(2,3-dihydro-thieno[3,4-b][1,4]dioxin-2-ylmethyl)-2-phenolsulfonic acid, sodium O-(2,3-dihydro-thieno[3,4-b][1,4]dioxin-2-ylmethyl)-2-phenolsulfonate, lithium O-(2,3-dihydro-thieno[3,4-b][1,4]dioxin-2-ylmethyl)-2-phenolsulfonate, potassium O-(2,3-dihydro-thieno[3,4-b][1,4]dioxin-2-ylmethyl)-2-phenolsulfonate, ammonium O-(2,3-dihydro-thieno[3,4-b][1,4]dioxin-2-ylmethyl)-2-phenolsulfonate, triethylammonium O-(2,3-dihydro-thieno[3,4-b][1,4]dioxin-4-ylmethyl)-2-phenolsulfonate, pyridinium O-(2,3-dihydro-thieno[3,4-b][1,4]dioxin-2-ylmethyl)-2-phenolsulfonate, 2-methyl-4-(2,3-dihydro-thieno[3,4-b][1,4]dioxin-2-ylmethoxy)benezenesulfonic acid, sodium 2-methyl-4-(2,3-dihydro-thieno[3,4-b][1,4]dioxin-2-ylmethoxy)benezenesulfonate, lithium 2-methyl-4-(2,3-dihydro-thieno[3,4-b][1,4]dioxin-2-ylmethoxy)benezenesulfonate, potassium 2-methyl-4-(2,3-dihydro-thieno[3,4-b][1,4]dioxin-2-ylmethoxy)benezenesulfonate, ammonium 2-methyl-4-(2,3-dihydro-thieno[3,4-b][1,4]dioxin-2-ylmethoxy)benezenesulfonate, triethylammonium 2-methyl-4-(2,3-dihydro-thieno[3,4-b][1,4]dioxin-2-ylmethoxy)benezenesulfonate, pyridinium 2-methyl-4-(2,3-dihydro-thieno[3,4-b][1,4]dioxin-2-ylmethoxy)benezenesulfonate, 3-methyl-4-(2,3-dihydro-thieno[3,4-b][1,4]dioxin-2-ylmethoxy)benezenesulfonic acid, sodium 3-methyl-4-(2,3-dihydro-thieno[3,4-b][1,4]dioxin-2-ylmethoxy)benezenesulfonate, lithium 3-methyl-4-(2,3-dihydro-thieno[3,4-b][1,4]dioxin-2-ylmethoxy)benezenesulfonate, potassium 3-methyl-4-(2,3-dihydro-thieno[3,4-b][1,4]dioxin-2-ylmethoxy)benezenesulfonate, ammonium 3-methyl-4-(2,3-dihydro-thieno[3,4-b][1,4]dioxin-2-ylmethoxy)benezenesulfonate, triethylammonium 3-methyl-4-(2,3-dihydro-thieno[3,4-b][1,4]dioxin-2-ylmethoxy)benezenesulfonate, pyridinium 3-methyl-4-(2,3-dihydro-thieno[3,4-b][1,4]dioxin-2-ylmethoxy)benezenesulfonate, 2-methoxy-4-(2,3-dihydro-thieno[3,4-b][1,4]dioxin-2-ylmethoxy)benezenesulfonic acid, sodium 2-methoxy-4-(2,3-dihydro-thieno[3,4-b][1,4]dioxin-2-ylmethoxy)benezenesulfonate, lithium 2-methoxy-4-(2,3-dihydro-thieno[3,4-b][1,4]dioxin-2-ylmethoxy)benezenesulfonate, potassium 2-methoxy-4-(2,3-dihydro-thieno[3,4-b][1,4]dioxin-2-ylmethoxy)benezenesulfonate, ammonium 2-methoxy-4-(2,3-dihydro-thieno[3,4-b][1,4]dioxin-2-ylmethoxy)benezenesulfonate, triethylammonium 2-methoxy-4-(2,3-dihydro-thieno[3,4-b][1,4]dioxin-2-ylmethoxy)benezenesulfonate, pyridinium 2-methoxy-4-(2,3-dihydro-thieno[3,4-b][1,4]dioxin-2-ylmethoxy)benezenesulfonate, 3-methoxy-4-(2,3-dihydro-thieno[3,4-b][1,4]dioxin-2-ylmethoxy)benezenesulfonic acid, sodium 3-methoxy-4-(2,3-dihydro-thieno[3,4-b][1,4]dioxin-2-ylmethoxy)benezenesulfonate, lithium 3-methoxy-4-(2,3-dihydro-thieno[3,4-b][1,4]dioxin-2-ylmethoxy)benezenesulfonate, potassium 3-methoxy-4-(2,3-dihydro-thieno[3,4-b][1,4]dioxin-2-ylmethoxy)benezenesulfonate, ammonium 3-methoxy-4-(2,3-dihydro-thieno[3,4-b][1,4]dioxin-2-ylmethoxy)benezenesulfonate, triethylammonium 3-methoxy-4-(2,3-dihydro-thieno[3,4-b][1,4]dioxin-2-ylmethoxy)benezenesulfonate, pyridinium 3-methoxy-4-(2,3-dihydro-thieno[3,4-b][1,4]dioxin-2-ylmethoxy)benezenesulfonate, (2,3-dihydro-thieno[3,4-b][1,4]dioxin-2-ylmethoxybenezen-4-yl)-2-ethane-1-sulfonic acid, sodium (2,3-dihydro-thieno[3,4-b][1,4]dioxin-2-ylmethoxybenezen-4-yl)-2-ethane-1-sulfonate, lithium (2,3-dihydro-thieno[3,4-b][1,4]dioxin-2-ylmethoxybenezen-4-yl)-2-ethane-1-sulfonate, potassium (2,3-dihydro-thieno[3,4-b][1,4]dioxin-2-ylmethoxybenezen-4-yl)-2-ethane-1-sulfonate, ammonium (2,3-dihydro-thieno[3,4-b][1,4]dioxin-2-ylmethoxybenezen-4-yl)-2-ethane-1-sulfonate, triethylammonium (2,3-dihydro-thieno[3,4-b][1,4]dioxin-2-ylmethoxybenezen-4-yl)-2-ethane-1-sulfonate, pyridinium (2,3-dihydro-thieno[3,4-b][1,4]dioxin-2-ylmethoxybenezen-4-yl)-2-ethane-1-sulfonate, (2,3-dihydro-thieno[3,4-b][1,4]dioxin-2-ylmethoxybenezen-4-yl)-3-propane-1-sulfonic acid, sodium (2,3-dihydro-thieno[3,4-b][1,4]dioxin-2-ylmethoxybenezen-4-yl)-3-propane-1-sulfonate, lithium (2,3-dihydro-thieno[3,4-b][1,4]dioxin-2-ylmethoxybenezen-4-yl)-3-propane-1-sulfonate, potassium (2,3-dihydro-thieno[3,4-b][1,4]dioxin-2-ylmethoxybenezen-4-yl)-3-propane-1-sulfonate, ammonium (2,3-dihydro-thieno[3,4-b][1,4]dioxin-2-ylmethoxybenezen-4-yl)-3-propane-1-sulfonate, triethylammonium (2,3-dihydro-thieno[3,4-b][1,4]dioxin-2-ylmethoxybenezen-4-yl)-3-propane-1-sulfonate, pyridinium (2,3-dihydro-thieno[3,4-b][1,4]dioxin-2-ylmethoxybenezen-4-yl)-3-propane-1-sulfonate, (2,3-dihydro-thieno[3,4-b][1,4]dioxin-2-ylmethoxybenezen-4-yl)-4-butane-1-sulfonic acid, sodium (2,3-dihydro-thieno[3,4-b][1,4]dioxin-2-ylmethoxybenezen-4-yl)-4-butane-1-sulfonate, lithium (2,3-dihydro-thieno[3,4-b][1,4]dioxin-2-ylmethoxybenezen-4-yl)-4-butane-1-sulfonate, potassium (2,3-dihydro-thieno[3,4-b][1,4]dioxin-2-ylmethoxybenezen-4-yl)-4-butane-1-sulfonate, ammonium (2,3-dihydro-thieno[3,4-b][1,4]dioxin-2-ylmethoxybenezen-4-yl)-4-butane-1-sulfonate, triethylammonium (2,3-dihydro-thieno[3,4-b][1,4]dioxin-2-ylmethoxybenezen-4-yl)-4-butane-1-sulfonate, pyridinium (2,3-dihydro-thieno[3,4-b][1,4]dioxin-2-ylmethoxybenezen-4-yl)-4-butane-1-sulfonate, (2,3-dihydro-thieno[3,4-b][1,4]dioxin-2-ylmethoxybenezen-4-yl)-6-hexane-1-sulfonic acid, sodium (2,3-dihydro-thieno[3,4-b][1,4]dioxin-2-ylmethoxybenezen-4-yl)-6-hexane-1-sulfonate, lithium (2,3-dihydro-thieno[3,4-b][1,4]dioxin-2-ylmethoxybenezen-4-yl)-6-hexane-1-sulfonate, potassium (2,3-dihydro-thieno[3,4-b][1,4]dioxin-2-ylmethoxybenezen-4-yl)-6-hexane-1-sulfonate, ammonium (2,3-dihydro-thieno[3,4-b][1,4]dioxin-2-ylmethoxybenezen-4-yl)-6-hexane-1-sulfonate, triethylammonium (2,3-dihydro-thieno[3,4-b][1,4]dioxin-2-ylmethoxybenezen-4-yl)-6-hexane-1-sulfonate, pyridinium (2,3-dihydro-thieno[3,4-b][1,4]dioxin-2-ylmethoxybenezen-4-yl)-6-hexane-1-sulfonate, (2,3-dihydro-thieno[3,4-b][1,4]dioxin-2-ylmethoxybenezen-3-yl)-2-ethane-1-sulfonic acid, sodium (2,3-dihydro-thieno[3,4-b][1,4]dioxin-2-ylmethoxybenezen-3-yl)-2-ethane-1-sulfonate, lithium (2,3-dihydro-thieno[3,4-b][1,4]dioxin-2-ylmethoxybenezen-3-yl)-2-ethane-1-sulfonate, potassium (2,3-dihydro-thieno[3,4-b][1,4]dioxin-3-ylmethoxybenezen-3-yl)-2-ethane-1-sulfonate, ammonium (2,3-dihydro-thieno[3,4-b][1,4]dioxin-2-ylmethoxybenezen-3-yl)-2-ethane-1-sulfonate, triethylammonium (2,3-dihydro-thieno[3,4-b][1,4]dioxin-2-ylmethoxybenezen-3-yl)-2-ethane-1-sulfonate, pyridinium (2,3-dihydro-thieno[3,4-b][1,4]dioxin-2-ylmethoxybenezen-3-yl)-2-ethane-1-sulfonate, (2,3-dihydro-thieno[3,4-b][1,4]dioxin-2-ylmethoxybenezen-3-yl)-3-propane-1-sulfonic acid, sodium (2,3-dihydro-thieno[3,4-b][1,4]dioxin-2-ylmethoxybenezen-3-yl)-3-propane-1-sulfonate, lithium (2,3-dihydro-thieno[3,4-b][1,4]dioxin-2-ylmethoxybenezen-3-yl)-3-propane-1-sulfonate, potassium (2,3-dihydro-thieno[3,4-b][1,4]dioxin-2-ylmethoxybenezen-3-yl)-3-propane-1-sulfonate, ammonium (2,3-dihydro-thieno[3,4-b][1,4]dioxin-2-ylmethoxybenezen-3-yl)-3-propane-1-sulfonate, triethylammonium (2,3-dihydro-thieno[3,4-b][1,4]dioxin-2-ylmethoxybenezen-3-yl)-3-propane-1-sulfonate, pyridinium (2,3-dihydro-thieno[3,4-b][1,4]dioxin-2-ylmethoxybenezen-3-yl)-3-propane-1-sulfonate, (2,3-dihydro-thieno[3,4-b][1,4]dioxin-2-ylmethoxybenezen-3-yl)-4-butane-1-sulfonic acid, sodium (2,3-dihydro-thieno[3,4-b][1,4]dioxin-2-ylmethoxybenezen-3-yl)-4-butane-1-sulfonate, lithium (2,3-dihydro-thieno[3,4-b][1,4]dioxin-2-ylmethoxybenezen-3-yl)-4-butane-1-sulfonate, potassium (2,3-dihydro-thieno[3,4-b][1,4]dioxin-2-ylmethoxybenezen-3-yl)-4-butane-1-sulfonate, ammonium (2,3-dihydro-thieno[3,4-b][1,4]dioxin-2-ylmethoxybenezen-3-yl)-4-butane-1-sulfonate, triethylammonium (2,3-dihydro-thieno[3,4-b][1,4]dioxin-2-ylmethoxybenezen-3-yl)-4-butane-1-sulfonate, pyridinium (2,3-dihydro-thieno[3,4-b][1,4]dioxin-2-ylmethoxybenezen-3-yl)-4-butane-1-sulfonate, (2,3-dihydro-thieno[3,4-b][1,4]dioxin-2-ylmethoxybenezen-3-yl)-6-hexane-1-sulfonic acid, sodium (2,3-dihydro-thieno[3,4-b][1,4]dioxin-2-ylmethoxybenezen-3-yl)-6-hexane-1-sulfonate, lithium (2,3-dihydro-thieno[3,4-b][1,4]dioxin-2-ylmethoxybenezen-3-yl)-6-hexane-1-sulfonate, potassium (2,3-dihydro-thieno[3,4-b][1,4]dioxin-2-ylmethoxybenezen-3-yl)-6-hexane-1-sulfonate, ammonium (2,3-dihydro-thieno[3,4-b][1,4]dioxin-2-ylmethoxybenezen-3-yl)-6-hexane-1-sulfonate, triethylammonium (2,3-dihydro-thieno[3,4-b][1,4]dioxin-2-ylmethoxybenezen-3-yl)-6-hexane-1-sulfonate, pyridinium (2,3-dihydro-thieno[3,4-b][1,4]dioxin-2-ylmethoxybenezen-3-yl)-6-hexane-1-sulfonate, and the like.

In the above formula (16), Ar is a phenylene group or naphthylene group which may have a substituent.

Further, the compound represented by the above formula (16) is preferably the compound represented by the above formula (21).

In the above formula (21), $R^2$ is a hydrogen atom or a $C_{1-6}$ alkyl group or alkoxy group which may have a substituent.

In the above formula (21), $R^2$ is not particularly limited and may, for example, be specifically a hydrogen atom, a $C_{1-6}$ alkyl group such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a cyclopentyl group, a n-hexyl group, a 2-ethylbutyl group, a cyclohexyl group or a n-octyl group, or an alkylene group. Preferred is a hydrogen atom, a methyl group, an ethyl group or a propyl group. Further, in a case where $R^2$ is an alkyl group or alkoxy group which has a substituent, the substituent may, for example, be a $C_{1-6}$ alkyl group or alkoxy group, a $C_{6-20}$ aryl group, a hydroxy group, an amino group or a carboxy group.

In the above formula (21), n, m, l and M are as defined in the above formula (16).

In the thiophene compound represented by the above formula (21), it is preferred that $R^2$ is a hydrogen atom and l=1.

The thiophene compound represented by the above formula (16) of the present invention is easily obtained by reacting a thiophene compound represented by the following formula (21) and a compound represented by the following formula (25) in an aprotic polar solvent in the presence of a base:

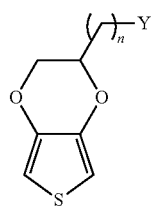

(24)

wherein Y is tosylate, mesylate, triflate, chloride, bromide or iodide, and n is an integer of from 0 to 6;

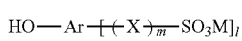

(25)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, $NH(R^1)_3$ or $HNC_5H_5$. $R^1$ is each independently a hydrogen atom or a $C_{1-6}$ alkyl group which may have a substituent, m is an integer of 0 or 1, and l is an integer of from 1 to 4.

The compound represented by the above formula (24) may, for example, be specifically 2,3-dihydro-thieno[3,4-b][1,4]dioxin-2-ylmethyl chloride, 2,3-dihydro-thieno[3,4-b][1,4]dioxin-2-ylmethyl bromide, 2,3-dihydro-thieno[3,4-b][1,4]dioxin-2-ylmethyl iodide, 2,3-dihydro-thieno[3,4-b][1,4]dioxin-2-ylmethyl tosylate, 2,3-dihydro-thieno[3,4-b][1,4]dioxin-2-ylmethyl mesylate, 2,3-dihydro-thieno[3,4-b][1,4]dioxin-2-ylmethyl triflate, 2,3-dihydro-thieno[3,4-b][1,4]dioxin-2-ylethyl chloride, 2,3-dihydro-thieno[3,4-b][1,4]dioxin-2-ylethyl bromide, 2,3-dihydro-thieno[3,4-b][1,4]dioxin-2-ylethyl iodide, 2,3-dihydro-thieno[3,4-b][1,4]dioxin-2-ylethyl tosylate, 2,3-dihydro-thieno[3,4-b][1,4]dioxin-2-ylethyl mesylate, 2,3-dihydro-thieno[3,4-b][1,4]dioxin-2-ylethyl triflate, 2,3-dihydro-thieno[3,4-b][1,4]dioxin-2-ylpropyl chloride, 2,3-dihydro-thieno[3,4-b][1,4]dioxin-2-ylpropyl bromide, 2,3-dihydro-thieno[3,4-b][1,4]dioxin-2-ylpropyl iodide, 2,3-dihydro-thieno[3,4-b][1,4]dioxin-2-ylpropyl tosylate, 2,3-dihydro-thieno[3,4-b][1,4]dioxin-2-ylpropyl mesylate, or 2,3-dihydro-thieno[3,4-b][1,4]dioxin-2-ylpropyl triflate.

The compound represented by the above formula (25) may, for example, be specifically as follows. 4-Phenolsulfonic acid, sodium 4-phenolsulfonate, potassium 4-phenolsulfonate, lithium 4-phenolsulfonate, ammonium 4-phenolsulfonate, 3-phenolsulfonic acid, sodium 3-phenolsulfonate, potassium 3-phenolsulfonate, lithium 3-phenolsulfonate, ammonium 3-phenolsulfonate, 2-phenolsulfonic acid, sodium 2-phenolsulfonate, potassium 2-phenolsulfonate, lithium 2-phenolsulfonate, ammonium 2-phenolsulfonate, 2,4-phenoldisulfonic acid, sodium 2,4-phenoldisulfonate, potassium 2,4-phenoldisulfonate, lithium 2,4-phenoldisulfonate, ammonium 2,4-phenoldisulfonate, 3,4-phenoldisulfonic acid, sodium 3,4-phenoldisulfonate, potassium 3,4-phenoldisulfonate, lithium 3,4-phenoldisulfonate, ammonium 3,4-phenoldisulfonate, 2-methyl-4-phenolsulfonic acid, sodium 2-methyl-4-phenolsulfonate, potassium 2-methyl-4-phenolsulfonate, lithium 2-methyl-4-phenolsulfonate, ammonium 2-methyl-4-phenolsulfonate, 2-methyl-3-phenolsulfonic acid, sodium 2-methyl-3-phenolsulfonate, potassium 2-methyl-3-phenolsulfonate, lithium 2-methyl-3-phenolsulfonate, ammonium 2-methyl-3-phenolsulfonate, 4-methyl-2-phenolsulfonic acid, sodium 4-methyl-2-phenolsulfonate, potassium 4-methyl-2-phenolsulfonate, lithium 4-methyl-2-phenolsulfonate, ammonium 4-methyl-2-phenolsulfonate, 3-methyl-2,4-phenoldisulfonic acid, sodium 3-methyl-2,4-phenoldisulfonate, potassium 3-methyl-2,4-phenoldisulfonate, lithium 3-methyl-2,4-phenoldisulfonate, ammonium 3-methyl-2,4-phenoldisulfonate, 2-methyl-3,4-phenoldisulfonic acid, sodium 2-methyl-3,4-phenoldisulfonate, potassium 2-methyl-3,4-phenoldisulfonate, lithium 2-methyl-3,4-phenoldisulfonate, ammonium 2-methyl-3,4-phenoldisulfonate, and the like.

The polar solvent used in this reaction is not particularly limited so long as the reaction proceeds in it, and may, for example, be N,N-dimethylaminoformamide, N-methylformamide, N-methylpyrrolidone, N,N-dimethylacetamide, methanol, acetone or water. Among them, more preferred is N,N-dimethylformamide. They may be used alone or as mixed optionally.

The amount of the polar solvent used is not particularly limited so long as it is such an amount that the compounds represented by the above formulae (24) and (25) as materials are dissolved, and for example, it is preferably within a range of from 0.1 to 200 times, more preferably from 1 to 100 times the weight of the compounds represented by the above formulae (24) and (25) charged.

The base used in this reaction is not particularly limited so long as the reaction proceeds, and may, for example, be sodium carbonate, potassium carbonate, cesium carbonate, sodium hydrogen carbonate, sodium hydride, lithium hydroxide, sodium hydroxide, potassium hydroxide, rubidium hydroxide, calcium hydroxide, ammonia water, pyridine, trimethylamine, triethylamine or tributylamine. Among them, more preferred is sodium carbonate or potassium carbonate.

The amount of the base used is not particularly limited, and for example, it is usually within a range of from 1 to 100 molar times, preferably within a range of from 1 to 10 molar times, further preferably within a range of from 2 to 5 molar times to the total number of moles of the compounds represented by the above formulae (24) and (25).

The reaction temperature of this reaction is not particularly limited so long as the reaction proceeds, and for example, it is usually within a range of from −20 to 200° C., preferably within a range of from 30 to 180° C., more preferably within a range of from 50 to 130° C.

The reaction atmosphere of this reaction is not particularly limited, and is preferably in the air, in nitrogen or in argon, more preferably in nitrogen.

The reaction pressure of this reaction may be ordinary pressure or elevated pressure and is not particularly limited, and is preferably ordinary pressure.

The thiophene compound used as a material is more preferably one having water solubility to such an extent that it is soluble in water at room temperature or with heating in an amount of at least 0.5 wt %.

Now, the thiophene compound represented by the above formula (17) will be described.

The compound represented by the above formula (17) may, for example, be specifically as follows.

Sodium 3-[(2,3-dihydrothieno[3,4-b][1,4]dioxin-2-yl)methoxy]-1-methyl-1-propanesulfonate, sodium 3-[(2,3-dihydrothieno[3,4-b]-[1,4]dioxin-2-yl)methoxy]-1-ethyl-1-propanesulfonate, sodium 3-[(2,3-dihydrothieno[3,4-b]-[1,4]dioxin-2-yl)methoxy]-1-propyl-1-propanesulfonate, sodium 3-[(2,3-dihydrothieno[3,4-b]-[1,4]dioxin-2-yl)methoxy]-1-butyl-1-propanesulfonate, sodium 3-[(2,3-dihydrothieno[3,4-b]-[1,4]dioxin-2-yl)methoxy]-1-pentyl-1-propanesulfonate, sodium 3-[(2,3-dihydrothieno[3,4-b]-[1,4]dioxin-2-yl)methoxy]-1-hexyl-1-propanesulfonate, sodium 3-[(2,3-dihydrothieno[3,4-b]-[1,4]dioxin-2-yl)methoxy]-1-isopropyl-1-propanesulfonate, sodium 3-[(2,3-dihydrothieno[3,4-b]-[1,4]dioxin-2-yl)methoxy]-1-isobutyl-1-propanesulfonate, sodium 3-[(2,3-dihydrothieno[3,4-b]-[1,4]dioxin-2-yl)methoxy]-1-isopentyl-1-propanesulfonate, sodium 3-[(2,3-dihydrothieno[3,4-b]-[1,4]dioxin-2-yl)methoxy]-1-fluoro-1-propanesulfonate, potassium 3-[(2,3-dihydrothieno[3,4-b]-[1,4]dioxin-2-yl)methoxy]-1-methyl-1-propanesulfonate, 3-[(2,3-dihydrothieno[3,4-b]-[1,4]dioxin-2-yl)methoxy]-1-methyl-1-propanesulfonic acid, ammonium 3-[(2,3-dihydrothieno[3,4-b]-[1,4]dioxin-2-yl)methoxy]-1-methyl-1-propanesulfonate, triethylammonium 3-[(2,3-dihydrothieno[3,4-b]-[1,4]dioxin-2-yl)methoxy]-1-methyl-1-propanesulfonate and the like.

Each of the above exemplified thiophene monomers may easily be prepared from thieno[3,4-b]-1,4-dioxin-2-methanol and a branched sultone compound in accordance with a known method (for example, Journal of Electroanalytical Chemistry, 443, 217 to 226 (1998)). Further, as the case requires, a thiophene monomer represented by the following formula (26) may be converted to a sulfonic acid wherein $M^1$ is a hydrogen atom by an acid treatment. Further, by subjecting the sulfonic acid to amine treatment, an ammonium salt may be obtained.

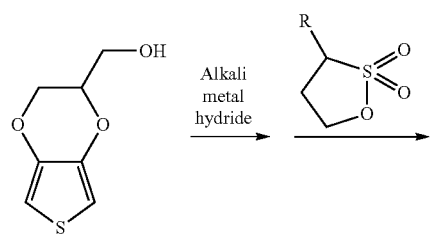

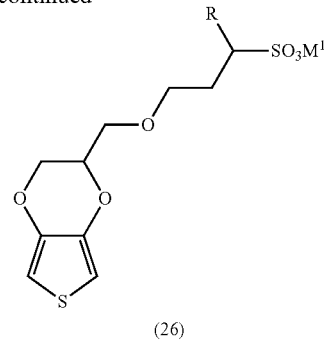

(26)

wherein R is the same as R in the above formula (5), and $M^1$ is an alkali metal.

EXAMPLES

Now, the present invention will be described with reference to Examples regarding the polythiophene (A) of the present invention. However, it should be understood that the present invention is by no means restricted to such specific Examples. Analytical instruments and measurement methods employed in Examples are mentioned below.

[GC Measurement]
Apparatus: manufactured by Shimadzu Corporation, GC-2014.

[NMR Measurement]
Apparatus: manufactured by Varian, Gemini-200.

[UV-Vis-NIR Analysis]
Apparatus: manufactured by Shimadzu Corporation, UV-3100.

[GPC Measurement]
Apparatus: manufactured by Tosoh Corporation,
Column: α-6000+α-3000,
Detector: UV-8020.

[IR Analysis]
Apparatus: manufactured by PerkinElmer, System 2000 FT-IR

[Surface Resistivity Measurement]
Apparatus: manufactured by Mitsubishi Chemical Corporation, Loresta GP MCP-T600.

[Film Thickness Measurement]
Apparatus: manufactured by Bruker, DEKTAK XT.

[Electric Conductivity Measurement]
0.5 ml of an aqueous solution containing 0.5 wt % of an electrically conductive polymer was applied to a 25 mm square alkali-free glass plate, dried overnight at room temperature, and then heated on a hot plate at 120° C. for 20 minutes and further at 160° C. for 10 minutes to obtain an electrically conductive polymer film. The electric conductivity was calculated from the film thickness and the surface resistivity in accordance with the following formula.

Electric conductivity [S/cm]=$10^4$/(surface resistivity [Ω/□]×film thickness [μm])

[Particle Size Measurement]
Apparatus: manufactured by Nikkiso Co., Ltd., Microtrac Nanotrac UPA-UT151.

[Test on Liquid Passing Through Filter]
Filter: manufactured by Nihon Entegris K.K., Optimizer V-47 disposable filter (hydrophilic), removed particle size: 0.05 μm.

A thiophene compound used as a material may be prepared in accordance with the following scheme. The starting material (22) was prepared from commercially available compound (27) by a known method used for preparation of 3,4-ethylenedioxythiophene.

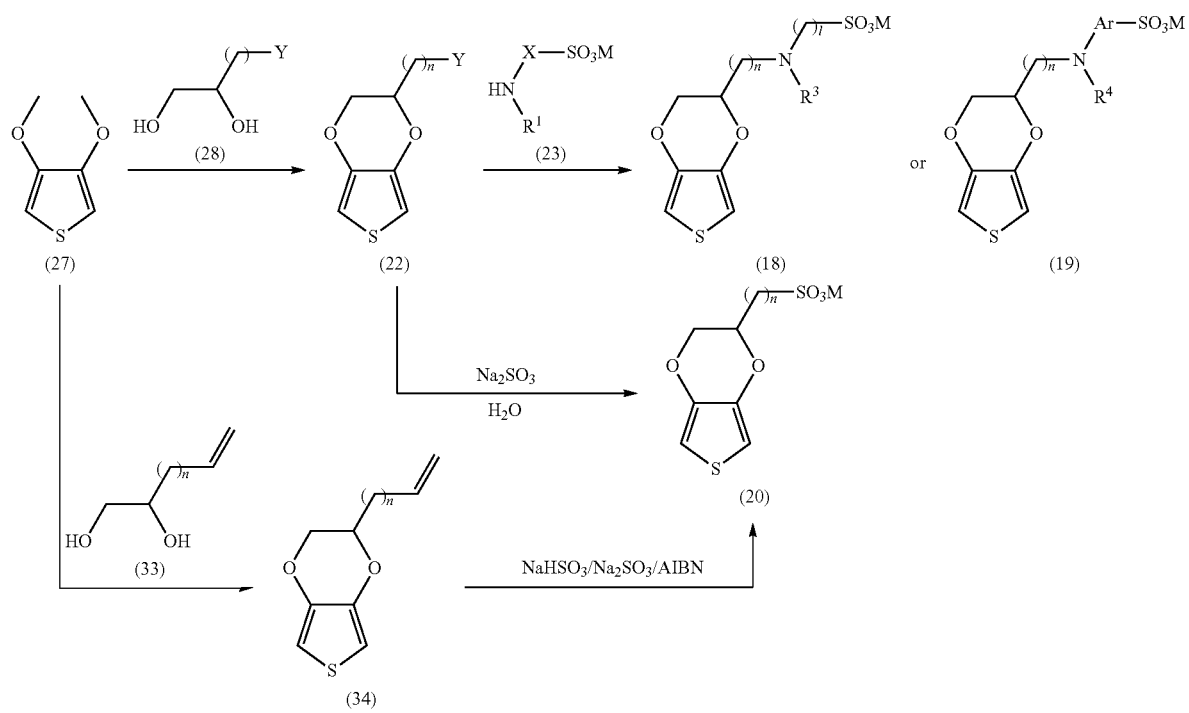

Preparation Example 1: Preparation of 2,3-dihydro-thieno[3,4-b][1,4]dioxin-2-ylmethyl bromide (Compound Represented by the Following Formula (29))

Into a 500 mL separable flask equipped with a condenser tube, a thermometer insertion tube, an agitating blade and a nitrogen induction tube, 20.0 g (134.5 mmol) of 3,4-dimethoxythiophene (corresponding to the above compound (27)), 25.0 g (161.5 mmol) of 3-bromo-1,2-propanediol [corresponding to the above compound (28)], p-toluenesulfonic acid monohydrate (5.33 g, 30.9 mmol) and 340 ml of toluene were charged and reacted in nitrogen atmosphere at 90° C. for 20 hours. The obtained black liquid was allowed to cool, diluted with methylene chloride and washed with water. The obtained green brown organic layer was dried over magnesium surface, and the filtrate was concentrated to obtain a yellow brown liquid. Continuously, the liquid was purified by silica gel chromatography (eluent: hexane/toluene=4/1) and concentrated, to obtain 18.9 g of compound represented by the following formula (29) (white solid, yield: 58%):

Example 1: Preparation of Potassium N-(2,3-dihydro-thieno[3,4-b][1,4]dioxin-2-ylmethyl)-2-aminoethanesulfonate (Compound Represented by the Following Formula (30))

In nitrogen, into a 200 mL three-necked flask, 3.00 g (12.6 mmol) of compound represented by the above formula (29) obtained in Preparation Example A-1, 1.57 g (12.6 mmol) of 2-aminoethanesulfonic acid (corresponding to the above compound (23)), 5.21 g (37.7 mmol) of potassium carbonate (base) and 131 mL of N,N-dimethylformamide (polar solvent) were charged and reacted in nitrogen atmosphere at 100° C. for 17 hours. From TLC (thin layer chromatography) analysis and GC (gas chromatography) analysis, disappearance of compound represented by the above formula (29) was confirmed. After the reaction mixture was allowed to cool, the precipitate was collected by filtration and washed with dimethylformamide. The obtained filtrate was roughly concentrated, washed with a methylene chloride/hexane mixed solvent and subjected to filtration under reduced pressure to obtain 3.01 g of the desired compound represented by the following formula (30) as a pale red solid (yield: 74%). This compound had water solubility of at least 1 wt % at room temperature. Further, it could be stored and handled in air.

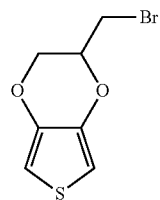

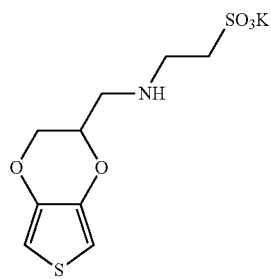

¹H-NMR (200 MHz, D₂O, internal standard: sodium 2,2,3,3-d(4)-3-(trimethylsilyl)propionate, the same applies hereinafter) δ (ppm) 6.67-6.53 (2H, m), 4.55-4.15 (4H, m), 3.31-2.88 (6H, m).

¹³C-NMR (50 MHz, D₂O, sodium 2,2,3,3-d(4)-3-(trimethylsilyl)propionate) δ (ppm) 46.66, 50.50, 52.65, 69.29, 75.55, 102.89, 103.18, 143.12, 143.31.

Example 2: Preparation of Sodium N-methyl-N-(2,3-dihydro-thieno[3,4-b][1,4]dioxin-2-ylmethyl)-2-aminoethanesulfonate (Compound Represented by the Following Formula (31))

Into a 500 mL four-necked separable flask equipped with a condenser tube, a thermometer insertion tube, an agitating blade and a nitrogen introduction tube, 3.00 g of compound represented by the above formula (29) obtained in Preparation Example 1, 3.42 g (13.8 mmol) of a 65 wt % aqueous solution of sodium N-methyltaurine (corresponding the above compound (1-6)), 5.21 g (37.7 mmol) of potassium carbonate (base) and 130 mL of N,N-dimethylformamide (polar solvent) were charged and reacted in nitrogen atmosphere at 90° C. for 22 hours. From TLC analysis and GC analysis, disappearance of compound represented by the above formula (29) was confirmed. After the reaction mixture was allowed to cool, the precipitate was collected by filtration and washed with dimethylformamide. The obtained filtrate was roughly concentrated, washed with a methylene chloride/hexane mixed solvent and subjected to filtration under reduced pressure to obtain 3.90 g of the desired compound represented by the following formula (31) as a white solid (yield: 99%). This compound had water solubility of at least 1 wt % at room temperature. Further, it could be stored and handled in air.

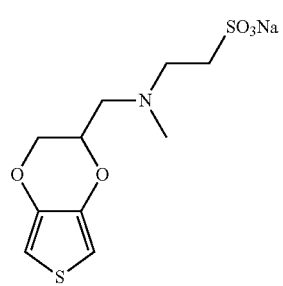

(31)

¹H-NMR (200 MHz, D₂O, sodium 2,2,3,3-d(4)-3-(trimethylsilyl)propionate) δ (ppm) 6.54-6.52 (2H, m), 4.50-4.45 (1H, m), 3.16-2.62 (8H, m), 2.37 (3H, s).

¹³C-NMR (50 MHz, D₂O, sodium 2,2,3,3-d(4)-3-(trimethylsilyl)propionate) δ (ppm) 44.28, 49.90, 54.46, 58.12, 69.53, 74.05, 102.86, 103.33, 142.94, 143.25.

Example 3: Preparation of Sodium 2,3-dihydro-thieno[3,4-b][1,4]dioxin-2-ylmethanesulfonate (Compound Represented by the Following Formula (32))

Into a 30 mL reaction tube, 1.00 g (4.25 mmol) of compound represented by the above formula (29) obtained in Preparation Example 1, 1.07 g (8.51 mmol) of sodium sulfite and 5 mL was water were charged and reacted in nitrogen atmosphere at 90° C. for 36 hours. From TLC analysis and GC analysis, disappearance of compound represented by the above formula (29) was confirmed. After the reaction mixture was allowed to cool, it was concentrated and evaporated to dryness, washed with methylene chloride and further subjected to extraction with dimethylformamide and filtration, and the obtained filtrate was roughly concentrated. Continuously, the obtained solid was washed with acetone and subjected to filtration under reduced pressure to obtain 1.02 g of the desired compound represented by the following formula (32) as a white solid (yield: 93%). This compound had water solubility of at least 1 wt % at room temperature. Further, it could be stored and handled in air.

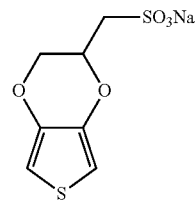

(32)

¹H-NMR (200 MHz, D₂O, sodium 2,2,3,3-d(4)-3-(trimethylsilyl)propionate) δ (ppm) 6.55 (2H, s), 4.33-4.10 (3H, m), 3.31-3.28 (2H, m).

¹³C-NMR (50 MHz, D₂O, sodium 2,2,3,3-d(4)-3-(trimethylsilyl)propionate) δ (ppm) 53.78, 69.82, 72.84, 103.07, 103.61, 142.59, 143.05.

Example 4: Preparation of sodium 6-(2,3-dihydro-thieno[3,4-b][1,4]dioxin-2-yl)-1-hexanesulfonate (36) (compound corresponding to the above formula (20))

(4-1) Preparation of 6-(2,3-dihydro-thieno[3,4-b][1,4]dioxin-2-yl)-1-hexene (35) (Compound Represented by the Above Formula (34))

Into a 500 mL separable flask equipped with a condenser tube, a thermometer insertion tube, an agitating blade and a nitrogen introduction tube, 20.0 g (97.0 GC %, 134.5 mmol) of commercially available 3,4-dimethoxythiophene (compound represented by the above formula (27)), 23.3 g (161.5 mmol) of 7-octene-1,2-diol (compound corresponding to the above formula (33)), sodium p-toluenesulfonate monohydrate (5.3 g, 30.9 mmol) and 400 mL of toluene were charged and reacted at 90° C. for 42 hours. After the reaction mixture was allowed to cool, it was put in a separatory funnel, washed with water and a saturated sodium hydrogen carbonate aqueous solution and extracted with dichloromethane. The obtained organic layer was dried over magnesium sulfate, and the filtrate was concentrated to obtain a pale yellow liquid. Continuously, the liquid was purified by silica gel chromatography (eluent: hexane/toluene=4/1) to obtain 14.9 g (yield: 49%) of the desired compound (35) as a pale yellow oil.

(35)

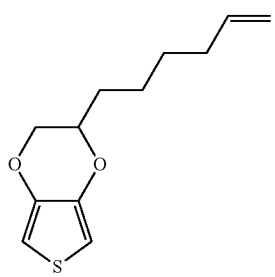

¹H-NMR (200 MHz, CDCl₃, internal standard: TMS) δ (ppm) 6.29 (2H, s), 5.91-5.70 (1H, m), 5.07-4.92 (2H, m), 4.15-4.03 (2H, m), 3.84 (1H, dd, J=10.6 Hz, 8.4 Hz), 2.13-2.03 (2H, m), 1.70-1.43 (6H, m).

¹³C-NMR (50 MHz, CDCl₃, TMS) δ (ppm) 24.45, 28.68, 30.49, 33.49, 68.34, 73.63, 99.12, 99.18, 114.54, 141.53, 141.99.

(4-2) Preparation of sodium 6-(2,3-dihydro-thieno [3,4-b][1,4]dioxin-2-yl)-1-hexanesulfonate (36) (compound corresponding the above formula (20))

Into a 500 mL separable flask equipped with a condenser tube, a thermometer insertion tube, an agitating blade and a nitrogen introduction tube, 14.9 g (98.0 GC %, 65.1 mmol) of compound represented by the above formula (35), 140.8 mg (0.98 mmol) of azobisisobutyronitrile and 150 mL of methanol were charged for dissolution at room temperature, and a separately prepared aqueous solution having 10.2 g (97.6 mmol) of sodium bisulfite and 2.1 g (16.3 mmol) of sodium sulfite dissolved in 130 mL of water was dropwise added thereto at room temperature. The clouded reaction liquid was reacted under reflux conditions for 44 hours. As the reaction proceeded, insoluble matters were once precipitated from the clouded liquid and then re-dissolved to obtain a uniform liquid. After the liquid was allowed to cool, it was concentrated to obtain a white solid, to which ethanol was added, followed by stirring and extraction overnight at room temperature. Continuously, insoluble matters were removed by filtration under reduced pressure, and the obtained colorless filtrate was concentrated to obtain 11.9 g (yield: 56%) of the desired compound (36) as a white solid. This compound had water solubility of at least 1 wt % at room temperature. Further, it could be stored and handled in air.

(36)

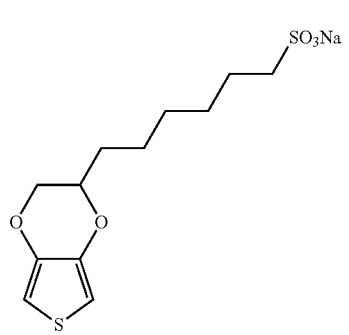

¹H-NMR (200 MHz, D₂O, sodium 2,2,3,3-d(4)-3-(trimethylsilyl)propionate) δ (ppm) 6.34 (2H, s), 4.20-4.14 (2H, m), 3.90-3.84 (1H, m), 2.88 (2H, t, J=8.2 Hz), 1.73-1.37 (10H, m).

¹³C-NMR (50 MHz, D₂O, sodium 2,2,3,3-d(4)-3-(trimethylsilyl)propionate) δ (ppm) 26.85, 27.07, 30.56, 53.84, 70.92, 76.91, 102.51, 102.58, 143.66, 143.95.

Example 5: Preparation of Polymer (39) (Polymer Containing Structural Units Represented by the Following Formula (37) or (38))

Figure 12:
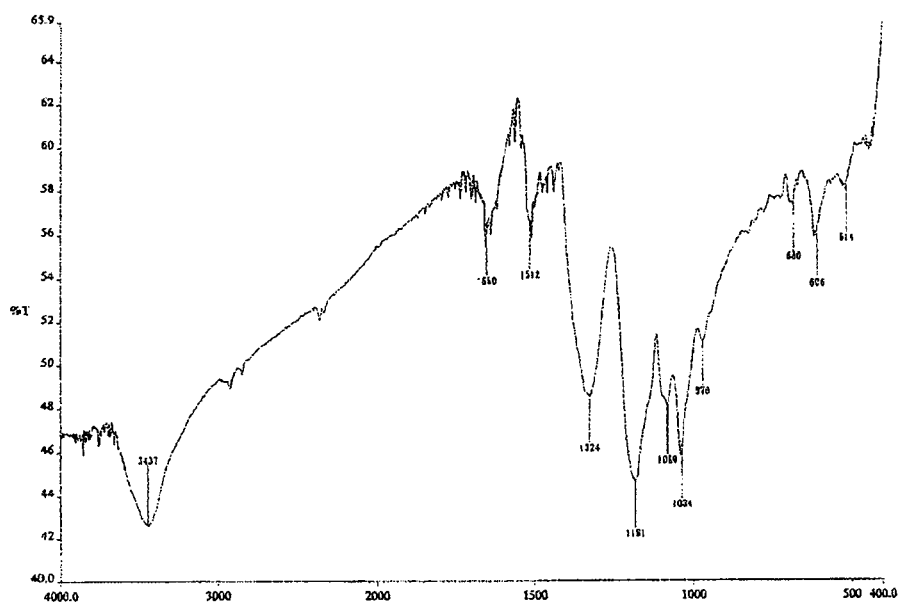
FIG. 12 illustrates IR analysis results of polymer (39) obtained in Example 5.

0.50 g (1.60 mmol) of compound represented by the above formula (31) obtained in Example 2 was dissolved in 4 mL of water to obtain a monomer aqueous solution. Then, the monomer aqueous solution was slowly added to 2.06 g (12.7 mmol) of FeCl₃ preliminarily charged in a 30 mL reaction tube equipped with a nitrogen line, followed by stirring in nitrogen at 80° C. for 60 hours. The obtained black liquid was slowly added to 500 mL of acetone with stirring, and the obtained precipitate was recovered by filtration under reduced pressure (0.39 g, black solid). This solid was suspended in 5 mL of water, and 24 g of a 0.1N NaOH aqueous solution was added thereto with vigorous stirring, to obtain a deep blue liquid. Continuously, this liquid was slowly added to 150 mL of ethanol with stirring, and the obtained precipitate was recovered by filtration under reduced pressure. Continuously, the precipitate was re-dissolved in 50 g of water, and the obtained polymer aqueous solution was subjected to filtration under reduced pressure to remove iron hydroxide. The filtrate was concentrated and dried to obtain 354 mg of the desired Na salt-form polymer (39) (black solid). As a result of UV-Vis-NIR analysis (ultraviolet/visible/near infrared spectroscopy) with respect to an aqueous solution containing 100 ppm of this polymer, long-wavelength absorption resulting from doping was observed (FIG. 1). In FIG. 12 are shown results of IR analysis (near infrared spectroscopy), and characteristics band absorption in the vicinity of from 3,600 to 1,800 cm⁻¹ resulting from doping was observed. Further, the electric conductivity of a film obtained by casting a 0.5 wt % aqueous solution of this polymer on an alkali-free glass plate was 3.7 S/cm. The particle size (D50) of the polymer in a 0.5 wt % aqueous solution was at most the detection limit (0.8 nm), and the aqueous solution passed through a 0.05 μm filter.

(37)

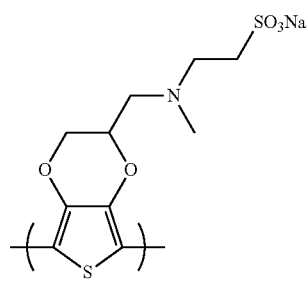

(38)

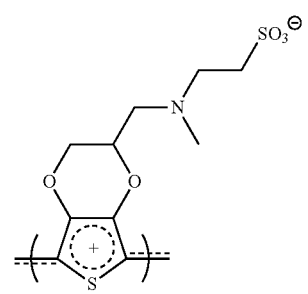

Example 6: Preparation of Polymer (42) (Polymer Containing Structural Units Represented by the Following Formula (40) or (41))

Figure 2:
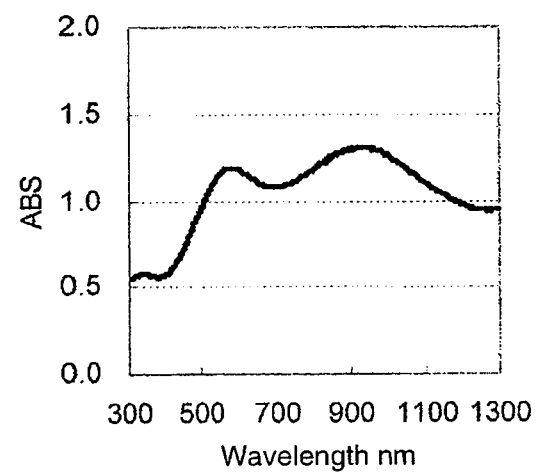
FIG. 2 illustrates UV-Vis-NIR analysis results of polymer (42) obtained in Example 6.
Figure 13:
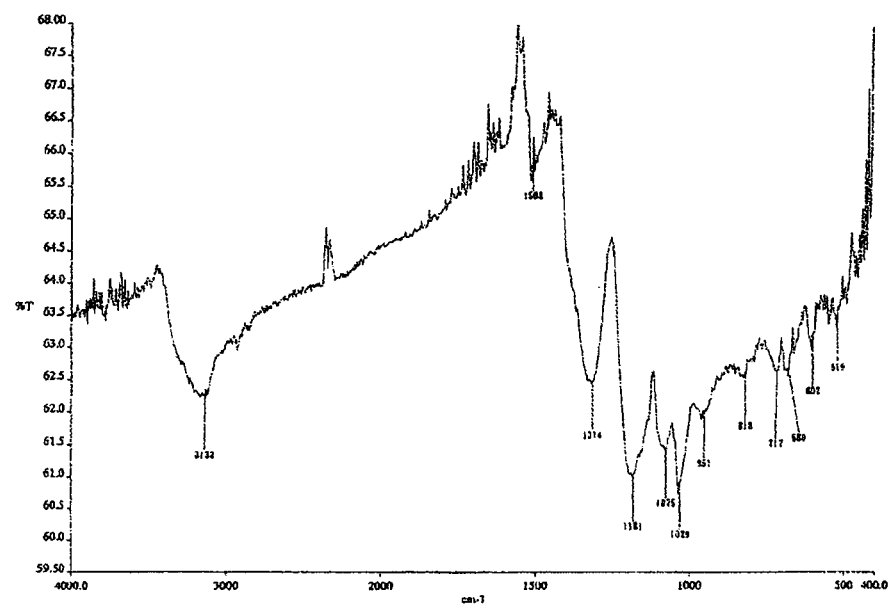
FIG. 13 illustrates IR analysis results of polymer (42) obtained in Example 6.

150 mg of Na salt-form polymer (39) obtained in Example 5 was diluted with water and dissolved into 15 g of a solution. To the aqueous solution, cation exchange resin Amberlite (IR120H) was added, followed by stirring overnight. Amberlite was removed by filtration under reduced pressure to obtain a deep blue H-form polymer aqueous solution. The aqueous solution was roughly concentrated, a 2.8 wt % ammonia water in an amount excess to the number of moles per monomer repeating unit was added thereto, followed by stirring in nitrogen at room temperature overnight. The reaction mixture was subjected to filtration under reduced pressure, the obtained filtrate was roughly concentrated, the resulting aqueous solution was added to acetone, and the obtained precipitate was recovered by filtration under reduced pressure. After drying, 99 mg (yield: 66%) of the desired $NH_4$ salt-form black polymer (42) was obtained. As a result of UV-Vis-NIR analysis with respect to an aqueous solution containing 100 ppm of this polymer, long-wavelength absorption resulting from doping was observed (FIG. 2). In FIG. 13 are shown results of IR analysis, and characteristics band absorption in the vicinity of from 3,600 to 1,800 $cm^{-1}$ resulting from doping was observed. Further, the electric conductivity of a film obtained by casting a 0.5 wt % aqueous solution of this polymer on an alkali-free glass plate was 4.9 S/cm. The particle size (D50) of the polymer in a 0.5 wt % aqueous solution was at most the detection limit (0.8 nm), and the aqueous solution passed through a 0.05 μm filter. The weight average molecular weight (as calculated as polystyrene sulfonic acid, the same applies hereinafter) by GPC was 15,000.

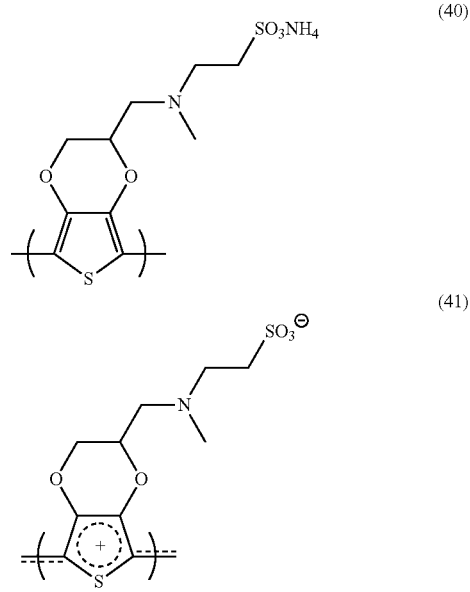

Example 7: Preparation of Polymer (39) (Polymer Containing Structural Units Represented by the Above Formula (37) or (38))

Figure 3:
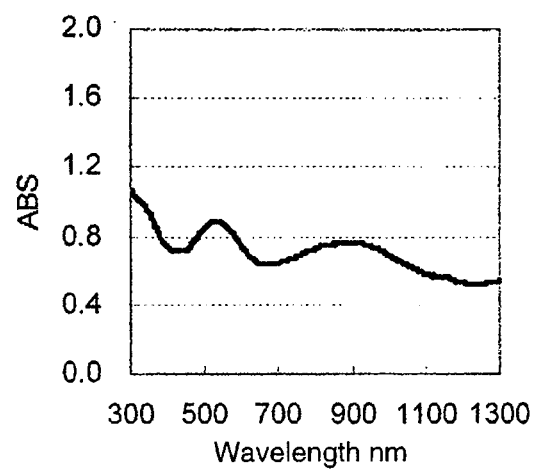
FIG. 3 illustrates UV-Vis-NIR analysis results of polymer (39) obtained in Example 7.

The same operation as in Example 5 was carried out except that the polymerization temperature was changed to room temperature, to obtain 370 mg of the desired Na salt-form polymer (39) (black solid). As a result of UV-Vis-NIR analysis with respect to an aqueous solution containing 100 ppm of this polymer, long-wavelength absorption resulting from doping was observed (FIG. 3). Further, the electric conductivity of a film obtained by casting a 0.5 wt % aqueous solution of this polymer on an alkali-free glass plate was 2.9 S/cm. The particle size (D50) of the polymer in a 0.5 wt % aqueous solution was at most the detection limit (0.8 nm), and the aqueous solution passed through a 0.05 μm filter.

Example 8: Preparation of Polymer (42) (Polymer Containing Structural Units Represented by the Following Formula (40) or (41))

Figure 4:
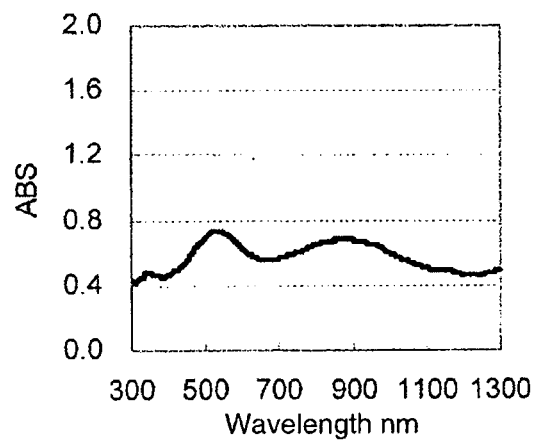
FIG. 4 illustrates UV-Vis-NIR analysis results of polymer (42) obtained in Example 8.

157 mg of Na salt-form polymer (39) obtained in Example 7 was diluted with water and dissolved into 15 g of a solution. To the aqueous solution, cation exchange resin Amberlite (IR120H) was added, followed by stirring overnight. Amberlite was removed by filtration under reduced pressure to obtain a deep blue H-form polymer aqueous solution (the particle size was at most the detection limit by Microtrac, and the aqueous solution passed through a 20 nm filter). The aqueous solution was roughly concentrated, a 2.8 wt % ammonia water in an amount excess to the number of moles per monomer repeating unit was added thereto, followed by stirring in nitrogen at room temperature overnight. The reaction mixture was subjected to filtration under reduced pressure, the obtained filtrate was roughly concentrated, the resulting aqueous solution was added to acetone, and the obtained precipitate was recovered by filtration under reduced pressure. After drying, 90 mg of the desired $NH_4$ salt-form black polymer (42) was obtained. As a result of UV-Vis-NIR analysis with respect to an aqueous solution containing 100 ppm of this polymer, long-wavelength absorption resulting from doping was observed (FIG. 4). Further, the electric conductivity of a film obtained by casting a 0.5 wt % aqueous solution of this polymer on an alkali-free glass plate was 2.4 S/cm. The particle size (D50) of the polymer in a 0.5 wt % aqueous solution was at most the detection limit (0.8 nm), and the aqueous solution passed through a 0.05 μm filter. The weight average molecular weight by GPC was 12,000.

Example 9: Preparation of Polymer (45) (Polymer Containing Structural Units Represented by the Following Formula (43) or (44))

Figure 5:
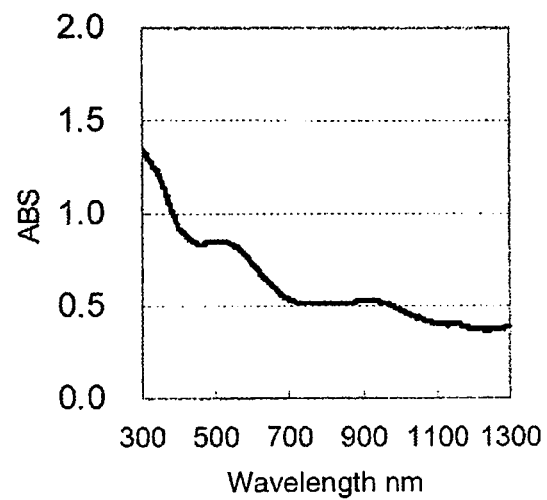
FIG. 5 illustrates UV-Vis-NIR analysis results of polymer (45) obtained in Example 9.

1.01 g (3.18 mmol) of compound represented by the above formula (30) obtained in Example 1 was dissolved in 14 mL of water to obtain a monomer aqueous solution. Then, the monomer aqueous solution was slowly added to 4.12 g (25.4 mmol) of $FeCl_3$ preliminarily charged in a 30 mL reaction tube equipped with a nitrogen line, followed by stirring in nitrogen at 80° C. for 60 hours. The obtained black liquid was slowly added to 200 mL of acetone with stirring, and the obtained precipitate was recovered by filtration under reduced pressure (0.96 g, black solid). This solid was suspended in 10 mL of water, and 48 g of a 0.1N NaOH aqueous solution was added thereto with vigorous stirring, to obtain a deep blue liquid. Continuously, this liquid was slowly added to 700 mL of ethanol with stirring, and the obtained black precipitate was recovered by filtration under reduced pressure. Continuously, the precipitate was re-dissolved in 100 g of water, and the obtained polymer aqueous solution was subjected to filtration under reduced pressure to remove iron hydroxide. The filtrate was concentrated and dried to obtain 860 mg (black solid) of the desired Na salt-form polymer (45). As a result of UV-Vis-NIR analysis with respect to an aqueous solution containing 100 ppm of this polymer, long-wavelength absorption resulting from doping was observed (FIG. 5). Further, the electric conductivity of a film obtained by casting a 0.5 wt % aqueous solution of this polymer on an alkali-free glass plate was 2.1 S/cm. The particle size (D50) of the polymer in a 0.5 wt % aqueous solution was at most the detection limit (0.8 nm), and the aqueous solution passed through a 0.05 μm filter. The weight average molecular weight by GPC was 23,000.

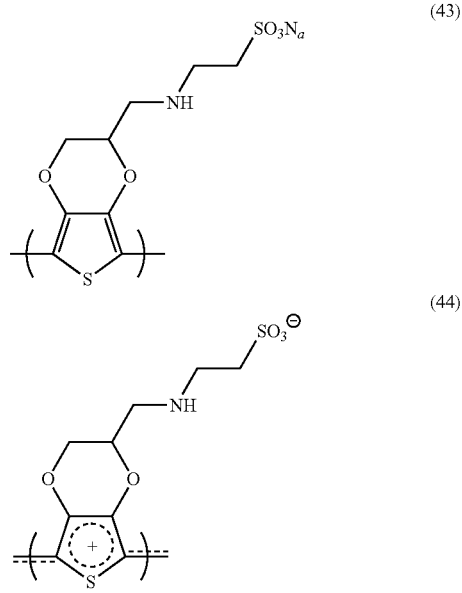

Example 10: Preparation of Polymer (48) (Polymer Containing Structural Units Represented by the Following Formula (46) or (47))

Figure 6:
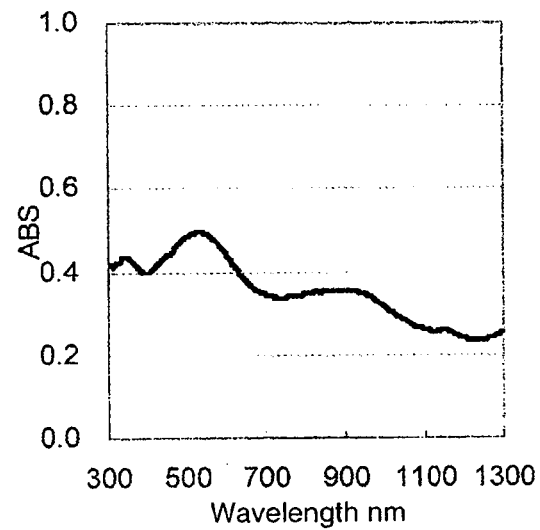
FIG. 6 illustrates UV-Vis-NIR analysis results of polymer (48) obtained in Example 10.

150 mg of Na salt-form polymer (45) obtained in Example 9 was diluted with water and dissolved into 15 g of a solution. To the aqueous solution, cation exchange resin Amberlite (IR120H) was added, followed by stirring overnight. Amberlite was removed by filtration under reduced pressure to obtain a deep blue H-form polymer aqueous solution. The aqueous solution was roughly concentrated, a 2.8 wt % ammonia water in an amount excess to the number of moles per monomer repeating unit was added thereto, followed by stirring in nitrogen at room temperature overnight. The reaction mixture was subjected to filtration under reduced pressure, the obtained filtrate was roughly concentrated, the resulting aqueous solution was added to acetone, and the obtained precipitate was recovered by filtration under reduced pressure. After drying, 18 mg of the desired $NH_4$ salt-form black polymer (48) was obtained. As a result of UV-Vis-NIR analysis with respect to an aqueous solution containing 100 ppm of this polymer, long-wavelength absorption resulting from doping was observed (FIG. 6). Further, the electric conductivity of a film obtained by casting a 0.5 wt % aqueous solution of this polymer on an alkali-free glass plate was 2.7 S/cm. The particle size (D50) of the polymer in a 0.5 wt % aqueous solution was at most the detection limit (0.8 nm), and the aqueous solution passed through a 0.05 μm filter.

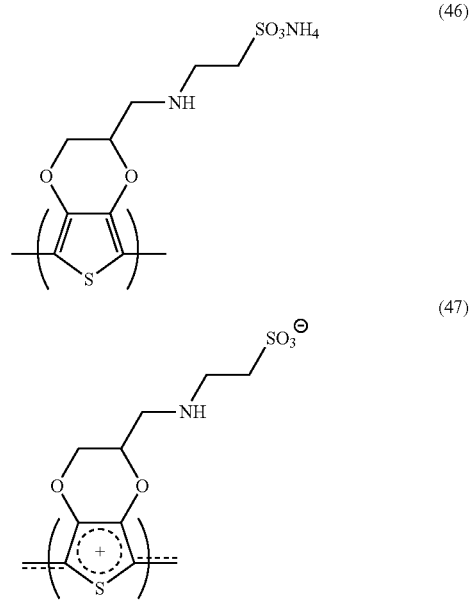

Example 11: Preparation of Polymer (51) (Polymer Containing Structural Units Represented by the Following Formula (49) or (50))

Figure 7:
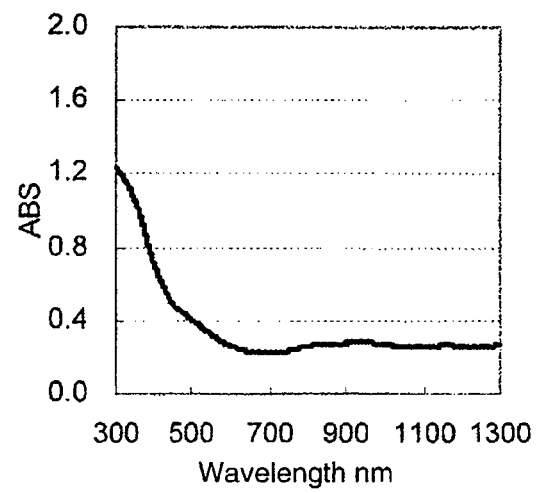
FIG. 7 illustrates UV-Vis-NIR analysis results of polymer (51) obtained in Example 11.
Figure 14:
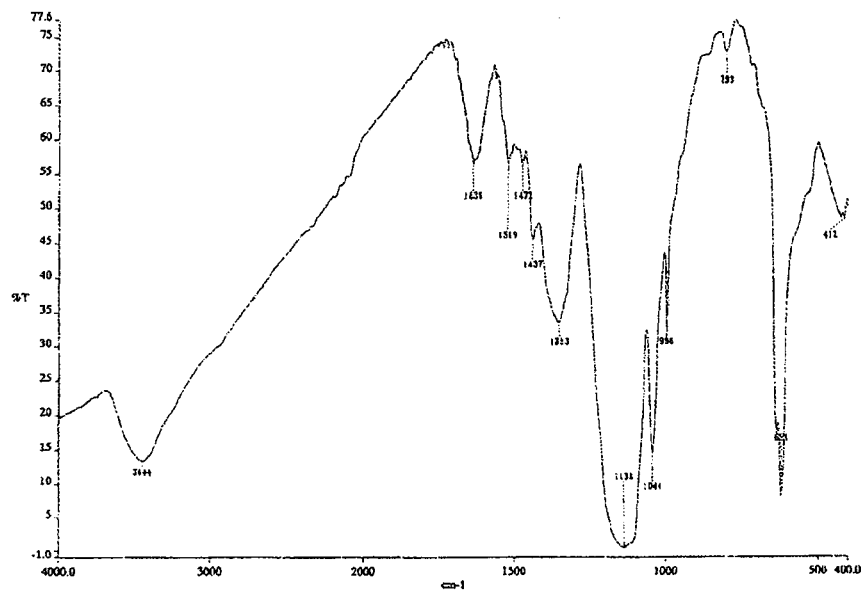
FIG. 14 illustrates IR analysis results of polymer (51) obtained in Example 11.

1,100 mg (2.26 mmol, purity: 53.1 wt %, containing inorganic salt) of compound represented by the above formula (32) obtained in Example 4 was dissolved in 12 mL of water to obtain a monomer aqueous solution. Then, the monomer aqueous solution was slowly added to 2.93 g (18.0 mmol) of $FeCl_3$ preliminarily charged in a 30 mL reaction tube equipped with a nitrogen line, followed by stirring in nitrogen at 80° C. for 60 hours. The obtained black liquid was slowly added to 200 mL of acetone with stirring, and the obtained precipitate was recovered by filtration under reduced pressure (1.06 g, black solid). This solid was suspended in 5 mL of water, and 48 g of a 0.1N NaOH aqueous solution was added thereto with vigorous stirring, to obtain a deep blue liquid. Continuously, this liquid was slowly added to 700 mL of ethanol with stirring. Further, the liquid was subjected to centrifugal sedimentation (3,000 rpm), the resulting supernatant liquid was removed, and the black precipitate was recovered by filtration under reduced pressure. Continuously, the precipitate was re-dissolved in 100 g of water to obtain a polymer aqueous solution, which was subjected to filtration under reduced pressure to remove iron hydroxide. The filtrate was concentrated and dried to obtain 960 mg of the desired Na salt-form polymer (51) (black solid). As a result of UV-Vis-NIR analysis with respect to an aqueous solution containing 100 ppm of this polymer, long-wavelength absorption resulting from doping was observed (FIG. 7). In FIG. 14 are shown results of IR analysis, and characteristic band absorption in the vicinity of from 3,600 to 1,800 $cm^{-1}$ resulting from doping was observed. Further, the electric conductivity of a film obtained by casting a 0.5 wt % aqueous solution of this polymer on an alkali-free glass plate was 0.4 S/cm. The particle size (D50) of the polymer in a 0.5 wt % aqueous solution was at most the detection limit (0.8 nm), and the aqueous solution passed through a 0.05 μm filter. The weight average molecular weight by GPC was 36,000.

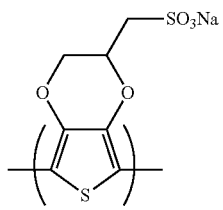

(49)

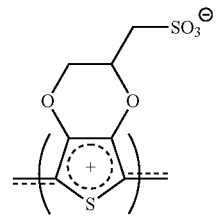

(50)

Example 12: Preparation of Polymer (54) (Polymer Containing Structural Units Represented by the Following Formula (52) or (53))

Figure 8:
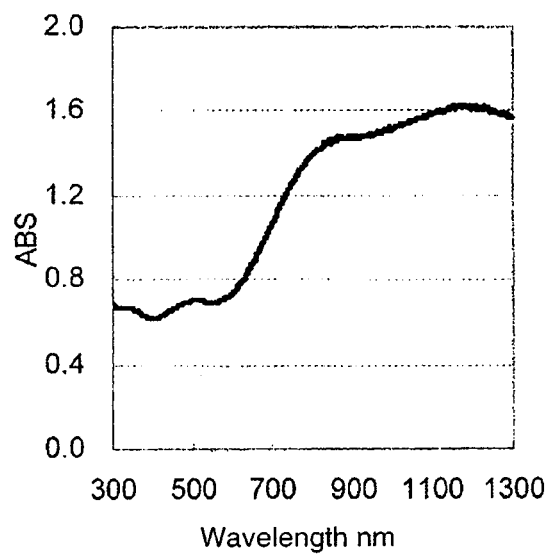
FIG. 8 illustrates UV-Vis-NIR analysis results of polymer (54) obtained in Example 12.
Figure 15:
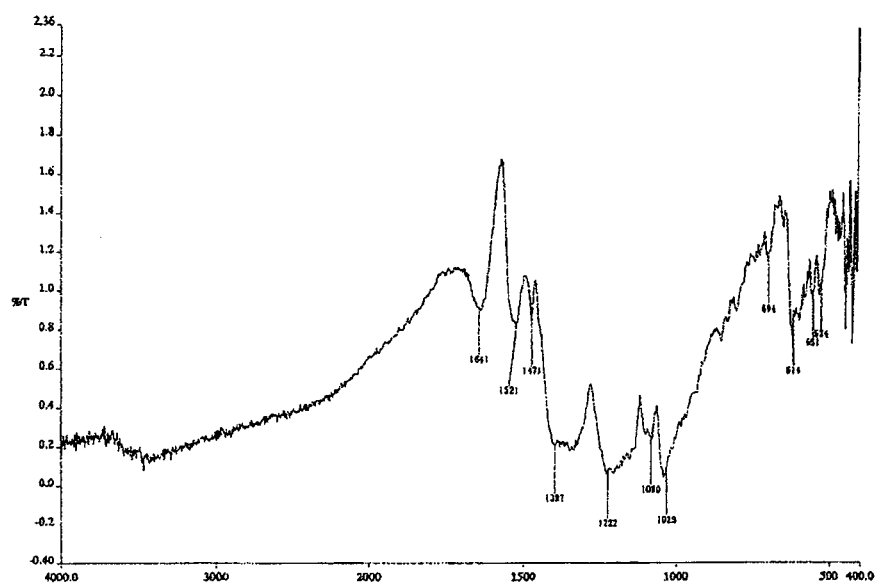
FIG. 15 illustrates IR analysis results of polymer (54) obtained in Example 12.

150 mg of Na salt-form polymer (51) obtained in Example 10 was diluted with water and dissolved into 15 g of a solution. To the aqueous solution, cation exchange resin Amberlite (IR120H) was added, followed by stirring overnight. Amberlite was removed by filtration under reduced pressure to obtain a deep blue H-form polymer aqueous solution (the particle size was at most the detection limit by Microtrac, and the aqueous solution passed through a 20 mm filter). The aqueous solution was roughly concentrated, and the concentrate was added to acetone to obtain a precipitate, which was recovered by filtration under reduced pressure. After drying, 38 mg of the desired H-form black polymer (54) was obtained. As a result of UV-Vis-NIR analysis with respect to an aqueous solution containing 100 ppm of this polymer, long-wavelength absorption resulting from doping was observed (FIG. 8). In FIG. 15 are shown results of IR analysis, and characteristic band absorption in the vicinity of from 3,600 to 1,800 cm$^{-1}$ resulting from doping was observed. Further, the electric conductivity of a film obtained by casting a 0.5 wt % aqueous solution of this polymer on an alkali-free glass plate was 2.1 S/cm. The particle size (D50) of the polymer in a 0.5 wt % aqueous solution was at most the detection limit (0.8 nm), and the aqueous solution passed through a 0.05 μm filter.

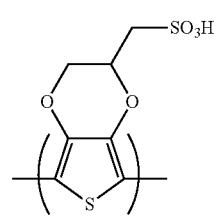

(52)

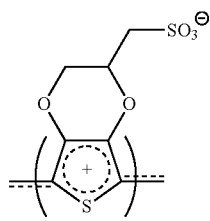

(53)

Example 13: Preparation of Polymer (57) (Polymer Containing Structural Units Represented by the Following Formula (55) or (56))

Figure 9:
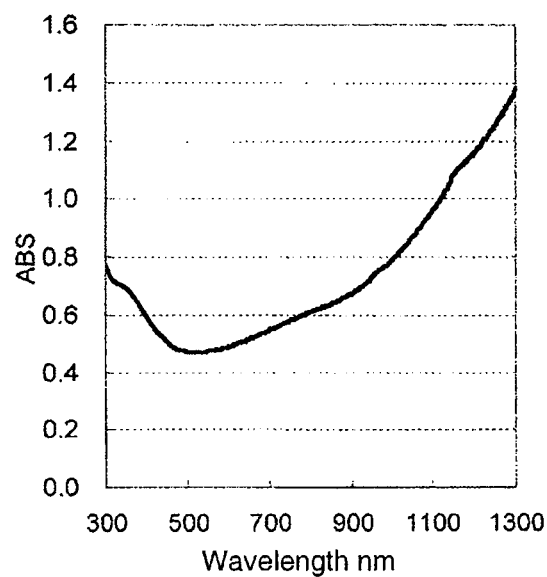
FIG. 9 illustrates UV-Vis-NIR analysis results of polymer (57) obtained in Example 13.
Figure 16:
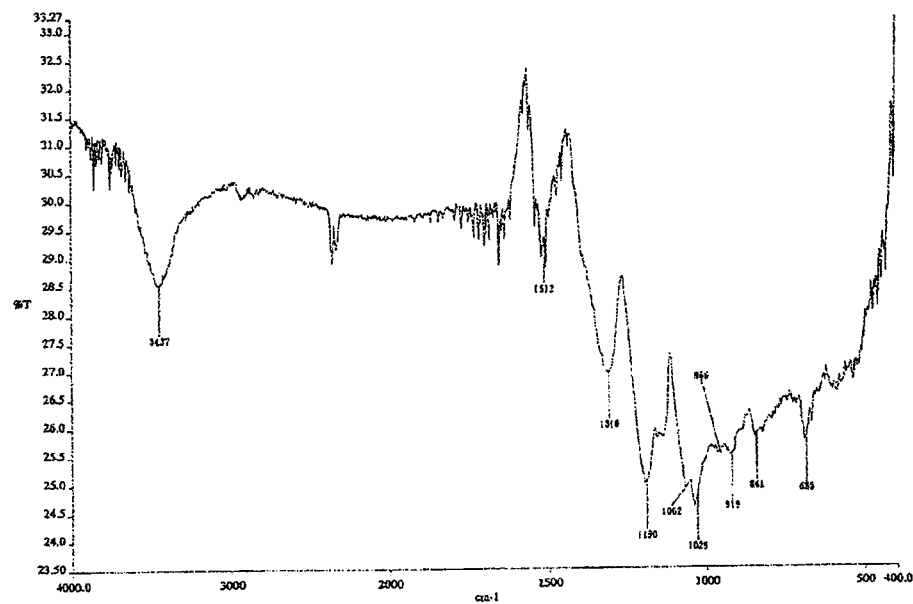
FIG. 16 illustrates IR analysis results of polymer (57) obtained in Example 13.

0.50 g (1.52 mmol) of compound represented by the above formula (36) obtained in Example 4 was dissolved in 5.9 mL of water to obtain a monomer aqueous solution. Then, the monomer aqueous solution was slowly added to 1.98 g (12.2 mmol) of FeCl$_3$ preliminarily charged in a 30 mL reaction tube equipped with a nitrogen line, followed by stirring in nitrogen at 80° C. for 48 hours. The obtained black liquid was slowly added to 150 mL of acetone with stirring, and the obtained precipitate was recovered by filtration under reduced pressure (0.45 g, black solid). This solid was suspended in 5 mL of water, and 60 g of a 0.1N NaOH aqueous solution was added thereto with vigorous stirring, to obtain a deep blue liquid. After insoluble matters were removed by filtration, this liquid was slowly added to 350 mL of ethanol with stirring. Further, the liquid was subjected to centrifugal sedimentation (3,000 rpm), the resulting supernatant liquid was removed, and the black precipitate was recovered by filtration under reduced pressure. Continuously, the precipitate was re-dissolved in 100 g of water to obtain a polymer aqueous solution, which was subjected to filtration under reduced pressure to remove iron hydroxide. The filtrate was concentrated and dried to obtain 0.27 g of the desired Na salt-form polymer (black solid). The weight average molecular weight of this polymer was 11,000. This polymer was diluted with 50 g of water and dissolved, and cation exchange resin Amberlite (IR120H) was added thereto, followed by stirring overnight. Amberlite was removed by filtration under reduced pressure to obtain a deep blue H-form polymer aqueous solution. The aqueous solution was roughly concentrated, the resulting concentrate was added to acetone, and the obtained precipitate was recovered by filtration under reduced pressure. After drying, 0.19 g of the desired H-form black polymer (57) was obtained. As a result of UV-Vis-NIR analysis with respect to an aqueous solution containing 100 ppm of this polymer, long-wavelength absorption resulting from doping was observed (FIG. 9). In FIG. 16 are shown results of IR analysis, and characteristics band absorption in the vicinity of from 3,600 to 1,800 cm$^{-1}$ resulting from doping was observed. Further, the electric conductivity of a film obtained by casting a 0.5 wt % aqueous solution of this polymer on an alkali-free glass plate was 31 S/cm. The particle size (D50) of the polymer in a 0.5 wt % aqueous solution was at most the detection limit (0.8 nm), and the aqueous solution passed through a 0.05 μm filter.

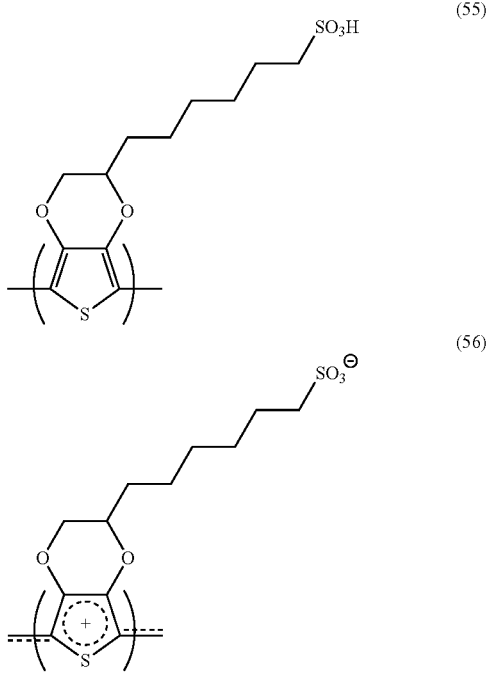

Example 14: Preparation of Polymer (57) (Polymer Containing Structural Units Represented by the Above Formula (55) or (56))

Figure 10:
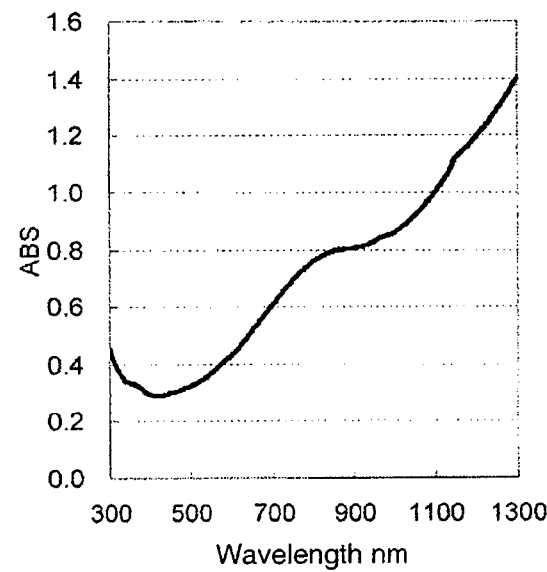
FIG. 10 illustrates UV-Vis-NIR analysis results of polymer (57) obtained in Example 14.
Figure 17:
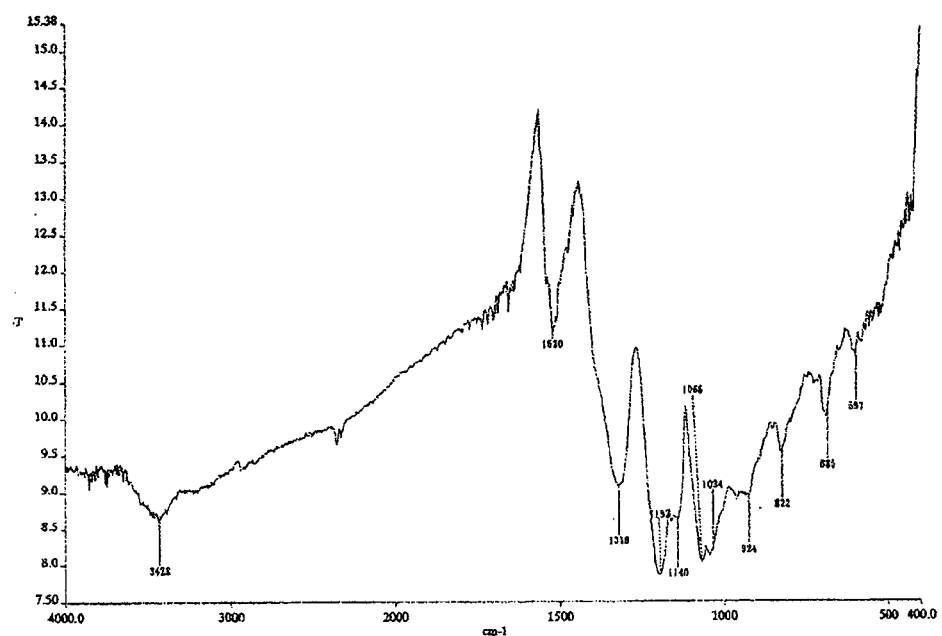
FIG. 17 illustrates IR analysis results of polymer (57) obtained in Example 14.

Into a 30 mL reaction tube, 1,000 mg (2.85 mmol) of compound (36) obtained in Example 4 and 14.8 g of water were charged to obtain a monomer aqueous solution. Then, 231 mg (1.43 mmol) of FeCl$_3$ was added, followed by stirring at room temperature for 30 minutes. To the obtained brown aqueous solution, a separately prepared oxidizing agent solution having 1,359 mg (5.71 mmol) of Na$_2$S$_2$O$_8$ dissolved in 8 mL of water was slowly added. The aqueous solution was changed to a deep blue liquid as the oxidizing agent solution was added, and the system was solidified. After polymerization at room temperature for 24 hours, the polymer liquid was poured into 700 mL of acetone to precipitate the polymer. The obtained polymer was collected by filtration to obtain 1.43 g of a pale green solid. Continuously, an aqueous solution in a total amount of 200 g was prepared with water, and cation exchange resin Amberlite (IR120H) was added thereto, followed by stirring overnight. Amberlite was removed by filtration under reduced pressure to obtain a deep blue H-form polymer aqueous solution. Further, inorganic salt was removed by dialysis (dialysis membrane: Spectra/Por MWCO=3500). The purified aqueous solution was concentrated and dried to obtain 460 mg of the desired H-form polymer (57) as a black solid (yield: 46%). As a result of UV-Vis-NIR analysis with respect to an aqueous solution containing 100 ppm of this polymer, long-wavelength absorption resulting from doping was observed (FIG. 10). In FIG. 17 are shown results of IR analysis, and characteristic band absorption in the vicinity of from 3,600 to 1,800 cm$^{-1}$ resulting from doping was observed. The electric conductivity of a film obtained by casting a 0.5 wt % aqueous solution of this polymer on an alkali-free glass plate was 10 S/cm. The particle size (D50) of the polymer in a 0.5 wt % aqueous solution was at most the detection limit (0.8 nm), and the aqueous solution passed through a 0.05 μm.

Example 15: Preparation of Polymer (39) (Polymer Containing Structural Units Represented by the Above Formula (37) or (38))

0.50 g (1.60 mmol) of compound represented by the above formula (31) obtained in Example 2 was charged into a 30 mL reaction tube equipped with a nitrogen line, and 0.8 mL of water was added thereto for dissolution to obtain a monomer aqueous solution. Then, the monomer aqueous solution was slowly added to 5.2 g (12.7 mmol) of a commercially available 40 wt % FeCl$_3$ aqueous solution (manufactured by Wako Pure Chemical Industries, Ltd.). The iron concentration to the solvent (water) in the charged liquid was 35 wt %. Then, the aqueous solution was stirred in nitrogen at 80° C. for 24 hours. The obtained black liquid was slowly added to 500 mL of acetone with stirring, and the obtained precipitate was recovered by filtration under reduced pressure (black solid, 0.26 g). This solid was suspended in 5 mL of water, and 100 g of a 0.1N NaOH aqueous solution was added thereto with vigorous stirring to obtain a deep blue liquid. Continuously, this liquid was slowly added to 600 mL of ethanol with stirring, and the obtained precipitated was collected by filtration under reduced pressure. Continuously, the precipitate was re-dissolved in 50 g of water to obtain a polymer aqueous solution, which was subjected to filtration under reduced pressure to remove iron hydroxide. The filtrate was concentrated and dried to obtain 0.24 g of the desired Na salt-form polymer (39) (black solid).

Figure 11:
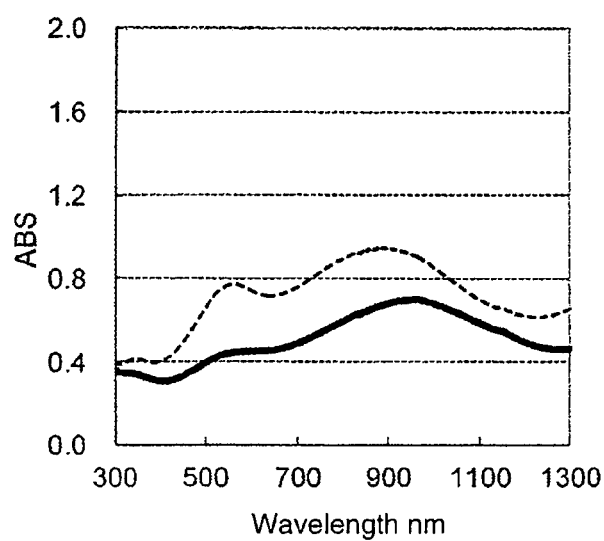
FIG. 11 illustrates UV-Vis-NIR analysis results of polymer (39) obtained Examples 15 and 16.

As a result of UV-Vis-NIR analysis with respect to an aqueous solution containing 100 ppm of this polymer, long-wavelength absorption resulting from doping was observed (FIG. 11, solid line). Further, the electric conductivity of a film obtained by casting a 0.5 wt % aqueous solution of this polymer on an alkali-free glass plate was 14.0 S/cm. Further, the particle size (D50) of the polymer in a 0.5 wt % aqueous solution was at most the detection limit (0.8 nm), and the aqueous solution passed through a 0.05 μm filter.

Example 16: Preparation of Polymer (39) (Polymer Containing Structural Units Represented by the Above Formula (37) or (38))

The same operation as in Example 15 was carried out except that the amount of the 40 wt % FeCl$_3$ aqueous solution was changed from 5.2 g (12.7 mmol) to 3.9 g (9.5 mmol), the amount of water to prepare the monomer aqueous solution was increased from 0.8 g to 2.3 g so that the monomer concentration to water agreed with that in Example 15. Here, the iron concentration to the solvent (water) in the charged liquid was 25 wt %. As a result, 0.22 g of Na salt-form polymer (39) was obtained as a black solid.

As a result of UV-Vis-NIR analysis with respect to an aqueous solution containing 100 ppm of this polymer, long-wavelength absorption resulting from doping was observed (FIG. 11, broken line). Further, the electric conductivity of a film obtained by casting a 0.5 wt % aqueous solution of this polymer on an alkali-free glass plate was 8.0 S/cm. Further, the particle size (D50) of the polymer in a 0.5 wt % aqueous solution was at most the detection limit (0.8 nm), and the aqueous solution passed through a 0.05 μm filter.

Comparative Example 1: Preparation of Polymer (64) (Polymer Containing Structural Units Represented by the Following Formula (62) or (63))

Polymer (64) was prepared in accordance with the following scheme with reference to Macromolecules, 1995, 975 to 984.

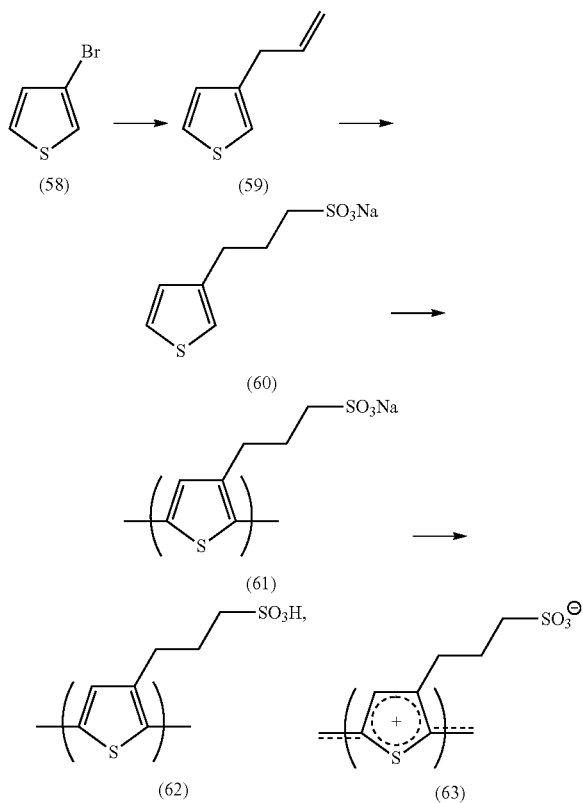

(1A) Preparation of 3-allylthiophene (59)

Into a 300 mL four-necked flask, 20.1 g (123.4 mmol) of 3-bromothiophene (58) and 80 mL of diethyl ether (dehydrated) were charged and cooled to −78° C. Then, 92 mL (147.2 mmol) of 1.6 M n-butyllithium was slowly dropwise added thereto over a period of one hour by a dropping funnel. After aging at the same temperature for 2 hours, 15.0 g (123.6 mmol) of allyl bromide was slowly added by a syringe, followed by ageing at the same temperature for 5 hours. The temperature was increased to 0° C., the reaction mixture was quenched with 100 mL of a saturated ammonium chloride aqueous solution, and the organic layer was extracted. Further, the organic layer was washed with water and a saturated sodium chloride solution, followed by liquid separation, and the obtained organic layer was dried over magnesium sulfate. The organic layer obtained by filtration was concentrated at 50° C. under a pressure of at most 20 Torr, to obtain 3.2 g of a brown oily substance. This was purified by Kugelrohr distillation (70 to 125° C., 25 Torr) to obtain 2.5 g of the desired compound (59) as a colorless transparent oily substance (yield: 16%).

(1B) Preparation of Sodium 3-(3-thienyl)propane-1-sulfonate (60)

In a 100 mL eggplant flask, 3 g (24.2 mmol) of 3-allylthiophene (59) prepared in the above (1A) was dissolved in 37 mL of methanol, and 0.05 g (0.30 mmol) of azobisisobutyronitrile was added. Further, a solution having 2.9 g (27.9 mmol) of NaHSO$_3$ and 0.59 g (4.60 mmol) of Na$_2$S$_2$O$_3$ dissolved in 24 mL of water was added at room temperature, followed by stirring at 80° C. overnight. While the reaction liquid was stirred, it was changed from a suspension to a uniform solution. After the solution was cooled, it was concentrated to obtain 7.30 g of a white solid. Continuously, the solid was washed with 35 mL of diethyl ether and subjected to filtration, and the obtained white solid was dried to obtain 5.14 g of a crude product. Further, the solid was extracted and washed with 100 mL of ethanol, and the filtrate obtained by filtration under reduced pressure was concentrated and dried to obtain 2.21 g of the desired compound (60) as a white crystal (yield: 52%).

(1C) Preparation of Polymer (61)

A monomer aqueous solution comprising 0.85 g (3.72 mmol) of compound (60) obtained in the above (1B) and 7.6 of water was slowly added to 2.40 g (14.8 mmol) of FeCl$_3$ preliminarily charged into a 30 mL reaction tube, followed by polymerization at room temperature for 22 hours. During polymerization, the reaction liquid was changed to a greenish black solution. After polymerization, the solution was slowly poured into 150 mL of acetone with stirring to precipitate polymer. The precipitate was well washed with acetone to obtain 0.17 g of black polymer. This polymer was suspended in 2 g of water, and 1.5 mL of a 1N NaOH aqueous solution was added thereto with vigorous stirring. By addition of the NaOH aqueous solution, the suspension was changed to a reddish brown uniform solution. Then, the solution was poured into 20 mL of methanol to precipitate polymer. The precipitate was collected by filtration and dried to obtain 0.12 g of the desired Na salt-form polymer (61) as a black solid (yield: 14%).

(1D) Preparation of Polymer (64)

In a 30 mL reaction tube, 122 mg of polymer (61) obtained in the above (1C) was suspended in 15 mL of water, followed by stirring for 2 hours. Then, the suspension was subjected to filtration under reduced pressure to obtain a deep red solution. 2 g of cation exchange resin (Lewatit S100 H) was added to the solution, followed by stirring overnight. The filtrate obtained by filtration was concentrated and dried to obtain 76 mg (yield: 63%) of the desired acid-form polymer (64) as a black solid. The electric conductivity of a film obtained by casting a 0.5 wt % aqueous solution of this polymer on an alkali-free glass plate was 0.06 S/cm. The particle size (D50) of the polymer in a 0.5 wt % aqueous solution was 10 nm.

Comparative Example 2: Preparation of Polymer (70) (Polymer Containing Structural Units Represented by the Following Formula (68) or (69))

Polymer (70) was prepared in accordance with the following scheme with reference to Japanese Patent No. 3182239.

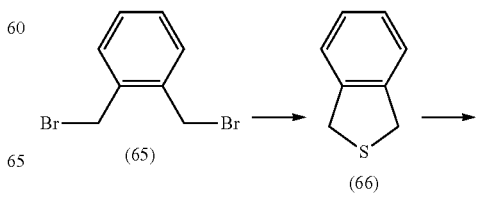

-continued

(67) → (68), (69)

(2A) Preparation of 1,3-dihydroisothianaphthene (66)

Into a 2 L separable flask, 10.0 g (38.0 mmol) of compound (65), 25.7 g (75.8 mmol) of tetra-n-butylammonium hydrogensulfide and 950 mL of chloroform were charged. After bubbling with nitrogen, a separately prepared aqueous solution having 13.9 g (57.8 mmol) of sodium sulfide nonahydrate and 6.4 g (75.6 mmol) of sodium hydrogen carbonate dissolved in 700 mL of water was dropwise added at room temperature over a period of 1.5 hours, followed by ageing further for one hour. After the reaction, the organic layer was obtained by liquid separation, and washed with 250 mL of water twice. The organic layer was dried over magnesium sulfate and concentrated to obtain a mixture of a white solid and an oily substance. Continuously, the mixture was purified by silica gel column chromatography (eluent: hexane/chloroform=4/1) to obtain 2.8 g of the desired compound (66) as a colorless transparent oily substance (yield: 55%).

(2B) Preparation of Polymer (67)

Into a 30 mL reaction tube, 3.0 g of 30 wt % fuming sulfuric acid was charged and cooled in an ice bath. Further, in a stream of nitrogen, compound (66) obtained in the above (2A) was dropwise added to the fuming sulfuric acid by a syringe. After stirring at room temperature for one hour, reaction was carried out at 70° C. for one hour. The reaction liquid was changed from brown to deep ultramarine blue immediately after dropping. After the reaction, the reaction liquid was dropwise added to 200 mL of a 0.1N NaOH-methanol solution to precipitate polymer. The polymer was sedimented by centrifugal separation (3,000 rpm) and dried to obtain 1.4 g of a black powder. Continuously, the black powder was dissolved in 100 g of water, and inorganic salt was removed by dialysis (dialysis membrane: Spectra/Por MWCO=0.1 to 0.5 K). The purified aqueous solution was concentrated and dried to obtain 1.1 g of the desired Na salt-form polymer (67) as a black solid (yield: 64%).

(2C) Preparation of Polymer (70)

Into a 30 mL reaction tube, 160 mg of Na salt-form polymer (67) obtained in the above (2B) and 23 g of water were charged to prepare an aqueous solution. To the aqueous solution, 2.5 g of cation exchange resin (Lewatit S100) which had been preliminarily converted to an acid form was added, followed by stirring overnight. The ion exchange resin was removed by filtration, and the obtained filtrate was concentrated and dried to obtain 140 mg of the desired acid-form polymer (70) as a black solid (yield: 89%). The electric conductivity of a film obtained by casting a 0.5 wt % aqueous solution of this polymer on an alkali-free glass plate was 0.1 S/cm. The particle size (D50) of the polymer in a 0.5 wt % aqueous solution was 6 nm.

Comparative Example 3: Preparation of Polymer (75) (Polymer Containing Structural Units Represented by the Following Formula (73) or (74))

Polymer (75) was prepared in accordance with the following scheme with reference to Journal of Electroanalytical Chemistry, 1998, 217 to 226 and Chemistry of Materials, 2009, 1815 to 1821.

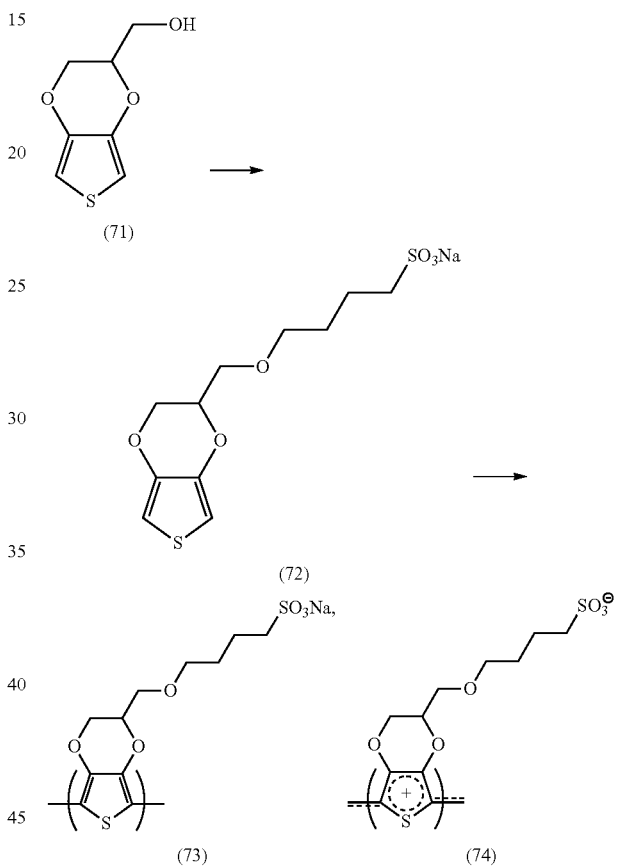

(3A) Preparation of Compound (72)

Into a 100 mL eggplant flask, 1.83 g of commercially available compound (71), 45 mL of toluene and 0.32 g (13.2 mmol) of 60 wt % NaH were charged and reacted under reflux conditions for one hour. 1.46 g (10.7 mmol) of 1,4-butanesultone dissolved in 12 mL of toluene was dropwise added under reflux. After ageing for 2 hours, the reaction mixture was cooled to room temperature and added to 200 mL of acetone to precipitate a jelly-like solid. The solid was collected by filtration with filter paper and dried under reduced pressure to obtain 2.0 g of the desired compound (72) as a pale brown solid (yield: 56%).

(3B) Preparation of Polymer (75)

Into a 50 mL schlenk tube, 0.81 g (2.44 mmol) of compound (72) obtained in the above (3A) and 12 mL of water were charged to obtain a monomer aqueous solution. A preliminarily prepared oxidizing agent aqueous solution having 1.16 g (4.86 mmol) of $Na_2S_2O_8$ and 0.02 g (0.10 mmol) of $FeCl_3$ dissolved in 12 mL of water was slowly added to the monomer aqueous solution. After polymerization at room temperature for 16 hours, the polymer liquid was poured into 160 mL of acetone to precipitate polymer. The obtained slurry was subjected to centrifugal sedimentation (3,000 rpm) to completely precipitate a solid to obtain 1.4 g of a black solid. Continuously, the solid was formed into an aqueous solution in a total amount of 80 g with water, and inorganic salt was removed by dialysis (dialysis membrane: Spectra/Por MWCO=0.1 to 0.5 K). The purified aqueous solution was concentrated and dried to obtain 553 mg of the desired Na salt-form polymer (75) as a black solid (yield: 69%). The electric conductivity of a film obtained by casting a 0.5 wt % aqueous solution of this polymer on an alkali-free glass plate was 0.3 S/cm. The particle size (D50) of the polymer in a 0.5 wt % aqueous solution was at most the detection limit (0.8 nm).

Now, Examples regarding the polythiophene (B) of the present invention will be described.

A thiophene compound used as a material may be prepared in accordance with the following scheme. Starting material (24) was prepared from commercially available compound (78) in accordance with a known method used for preparation of 3,4-ethylenedioxythiophene.

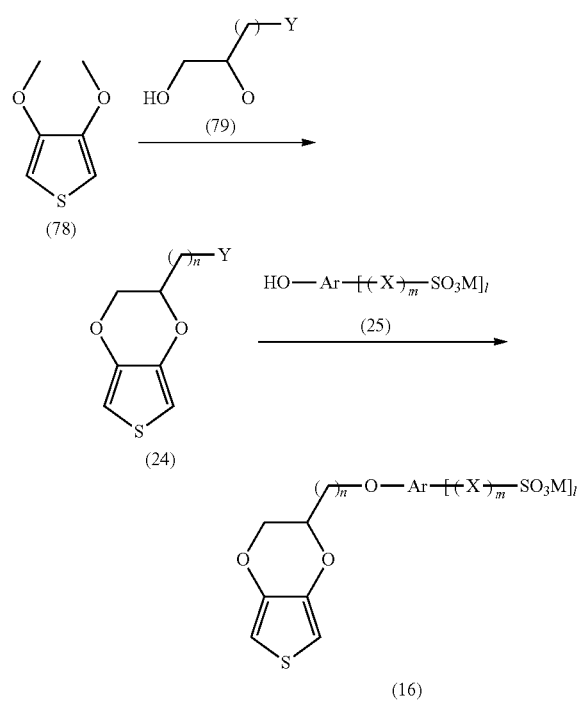

Preparation Example 2

Preparation of 2,3-dihydro-thieno[3,4-b][1,4]dioxin-2-ylmethyl bromide (Compound Represented by the Following Formula (80))

Into a 500 mL separable flask equipped with a condenser tube, a thermometer insertion tube, an agitating blade and a nitrogen introduction tube, 20.0 g (134.5 mmol) of 3,4-dimethoxythiophene (corresponding to the above compound (78)), 25.0 g (161.5 mmol) of 3-bromo-1,2-propanediol (corresponding to the above compound (23)), p-toluenesulfonic acid monohydrate (5.33 g, 30.9 mmol) and 340 mL of toluene were charged and reacted in nitrogen atmosphere at 90° C. for 20 hours. The obtained black liquid was allowed to cool, diluted with methylene chloride and washed with water. The obtained greenish brown organic layer was dried over magnesium sulfate, and the filtrate was concentrated to obtain a yellow brown liquid. Continuously, the liquid was purified by silica gel chromatography (eluent: hexane/toluene=4/1) and concentrated to obtain 18.9 g of compound represented by the following formula (80) (white solid, yield: 58%).

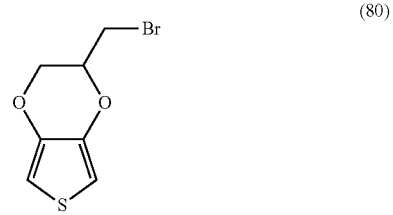 [SMILES: BrCC1COc2cscc2O1]

Example 17: Preparation of Potassium O-(2,3-dihydro-thieno[3,4-b][1,4]dioxin-2-ylmethyl)-4-phenolsulfonate (Compound Represented by the Following Formula (81))

Into a 200 mL three-necked flask equipped with a condenser tube, a thermometer insertion tube, a stirrer chip and a nitrogen introduction tube, 2.24 g (9.53 mmol) of compound represented by the above formula (80) obtained in Preparation Example 2, 2.08 g (11.9 mmol) of p-phenolsulfonic acid (corresponding to the above compound (25)), 5.78 g (41.8 mmol) of potassium carbonate (base) and 120 mL of N,N-dimethylformamide (polar solvent) were charged and reacted in nitrogen atmosphere at from 100 to 120° C. for 24 hours. From TLC analysis and GC analysis, disappearance of compound represented by the above formula (80) was confirmed. After the reaction mixture was allowed to cool, the precipitate was collected by filtration and washed with dimethylformamide. The obtained filtrate was roughly concentrated, washed with a methylene chloride/hexane mixed solvent and subjected to filtration under reduced pressure to obtain 1.96 g of the desired compound represented by the following formula (81) as a white solid (yield: 56%). This compound had water solubility of at least 1 wt %. Further, it could be stored and handled in air.

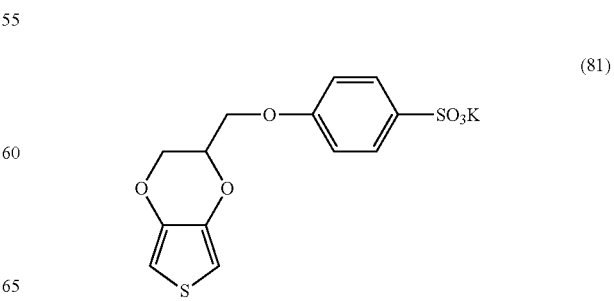

¹H-NMR (200 MHz, D₂O, sodium 2,2,3,3-d(4)-3-(trimethylsilyl)propionate) δ (ppm) 7.78-7.68 (2H, m), 7.11-6.96 (2H, m) 6.56-6.54 (2H, m), 4.76-4.61 (1H, m), 4.37-4.28 (4H, m).

¹³C-NMR (50 MHz, D₂O, sodium 2,2,3,3-d(4)-3-(trimethylsilyl)propionate) δ (ppm) 68.14, 69.35, 75.02, 103.21, 103.35, 117.47, 130.09, 138.11, 142.85, 143.20, 162.70.

Example 18: Preparation of sodium O-(2,3-dihydrothieno[3,4-b][1,4]dioxin-2-ylmethyl)-4-phenolsulfonate (Compound Represented by the Following Formula (82))

Into a 1 L separable flask equipped with a condenser tube, a thermometer insertion tube, a stirrer chip and a nitrogen introduction tube, 10.0 g (42.1 mmol) of compound (80) obtained in Preparation Example 2, 11.9 g (50.5 mmol) of sodium p-phenolsulfonate dihydrate (compound of the formula (25)), 25.6 g (185.3 mmol) of potassium carbonate (base) and 630 mL of N,N-dimethylformamide (polar solvent) were charged and reacted in nitrogen atmosphere at 120° C. for 24 hours. From TLC analysis and GC analysis, disappearance of compound (80) was confirmed. After the reaction mixture was allowed to cool, the precipitate was collected by filtration and washed with dimethylformamide. The obtained filtrate was roughly concentrated, washed with a methylene chloride/hexane mixed solvent and subjected to filtration under reduced pressure to obtain 8.6 g of the desired compound (82) as a white solid (yield: 58%). This compound had water solubility of at least 1%. Further, it could be stored and handled in air.

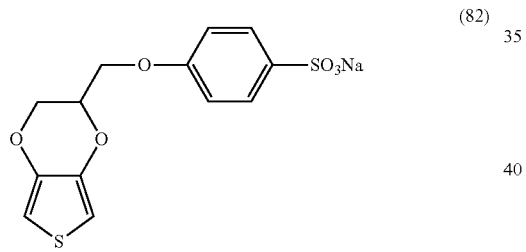

(82)

¹H-NMR (200 MHz, D₂O, sodium 2,2,3,3-d(4)-3-(trimethylsilyl)propionate) δ (ppm) 7.78-7.68 (2H, m), 7.11-6.96 (2H, m) 6.56-6.54 (2H, m), 4.76-4.61 (1H, m), 4.37-4.28 (4H, m).

¹³C-NMR (50 MHz, D₂O, sodium 2,2,3,3-d(4)-3-(trimethylsilyl)propionate) δ (ppm) 68.14, 69.35, 75.02, 103.21, 103.35, 117.47, 130.09, 138.11, 142.85, 143.20, 162.70.

Example 19: Preparation of Polymer (85) (Polymer Containing Structural Units Represented by the Following Formula (83) or (84))

Figure 18:
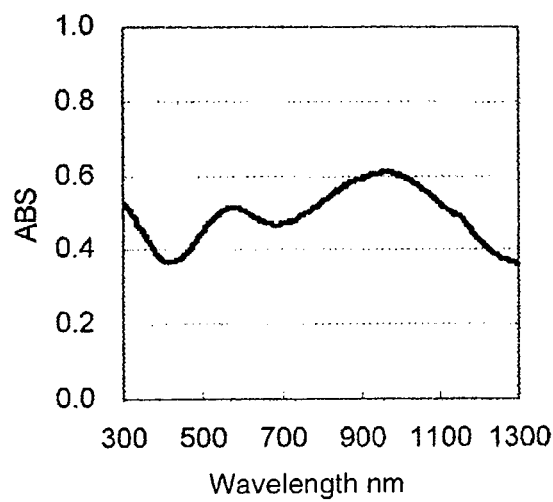
FIG. 18 illustrates UV-Vis-NIR analysis results of polymer (85) obtained in Example 19.
Figure 22:
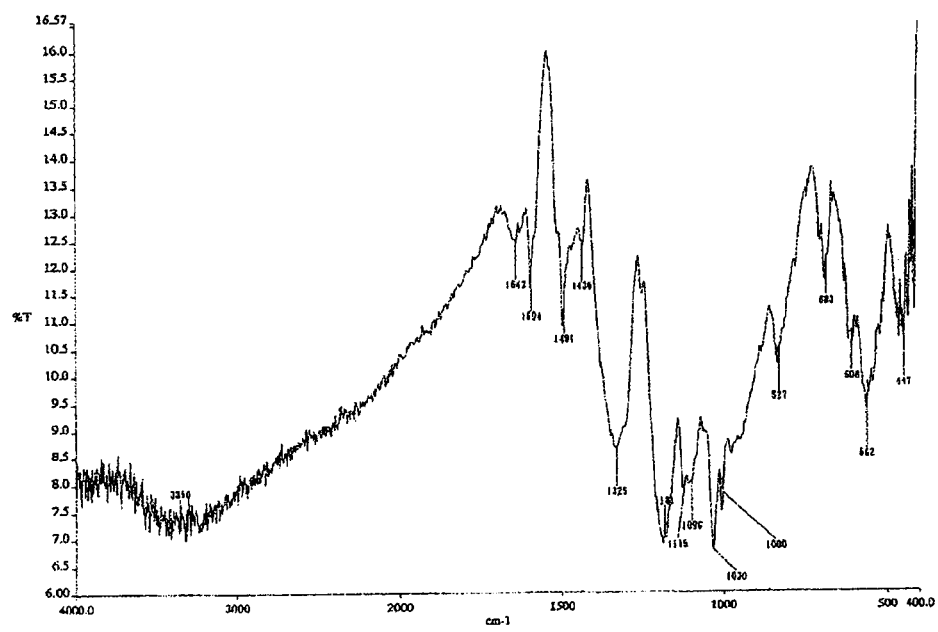
FIG. 22 illustrates IR analysis results of polymer (85) obtained in Example 19.

1.17 g (3.18 mmol) of compound represented by the above formula (81) obtained in Example 17 was dissolved in 16 mL of water to obtain a monomer aqueous solution. Then, the monomer aqueous solution was slowly added to 4.14 g (25.5 mmol) of FeCl₃ preliminarily charged in a 30 mL reaction tube equipped with a nitrogen line, followed by stirring in nitrogen at 80° C. for 60 hours. The obtained black liquid was slowly added to 500 mL of acetone with stirring, and the obtained precipitate was recovered by filtration under reduced pressure (0.41 g, deep green solid). This solid was suspended in 5 mL of water, and 50 g of a 0.1N NaOH aqueous solution was added thereto with vigorous stirring, to obtain a deep blue liquid. Continuously, this liquid was slowly added to 800 mL of ethanol with stirring, and the obtained precipitate was recovered by filtration under reduced pressure. Continuously, the precipitate was re-dissolved in 50 g of water, and the obtained polymer aqueous solution was subjected to filtration under reduced pressure to remove iron hydroxide. The filtrate was concentrated and dried to obtain 330 mg of the desired Na salt-form polymer (85) (black solid). As a result of UV-Vis-NIR analysis with respect to an aqueous solution containing 100 ppm of this polymer, long-wavelength absorption resulting from doping was confirmed (FIG. 18). In FIG. 22 are shown results of IR analysis. Characteristics band absorption in the vicinity of from 3,600 to 1,800 cm⁻¹ resulting from doping was observed. Further, the electric conductivity of a film obtained by casting a 0.5 wt % aqueous solution of this polymer on an alkali-free glass plate was 4.3 S/cm. The particle size (D50) of the polymer in a 0.5 wt % aqueous solution was at most the detection limit (0.8 nm), and the aqueous solution passed through a 0.05 μm filter. The weight average molecular weight (as calculated as polystyrene sulfonic acid, the same applies hereinafter) by GPC was 18,000.

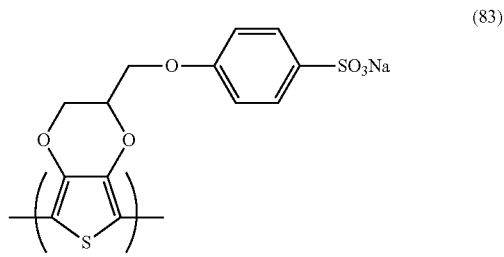

(83)

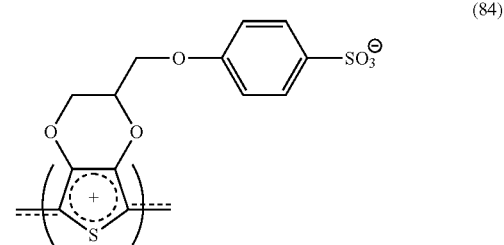

(84)

Example 20: Preparation of Polymer (88) (Polymer Containing Structural Units Represented by the Following Formula (86) or (87))

Figure 19:
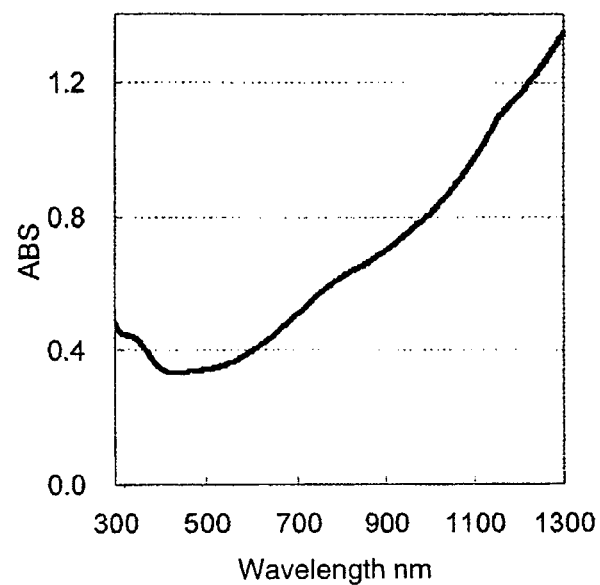
FIG. 19 illustrates UV-Vis-NIR analysis results of polymer (88) obtained in Example 20.
Figure 23:
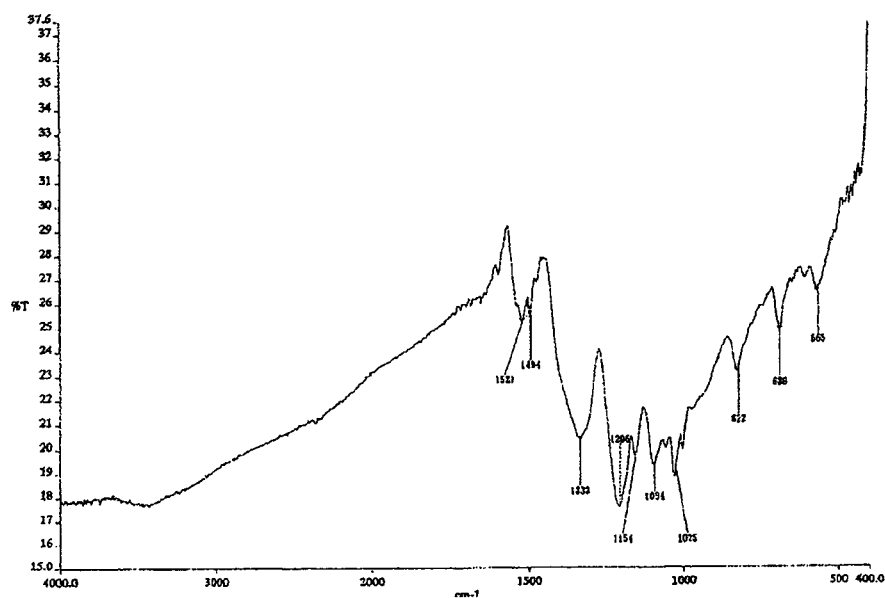
FIG. 23 illustrates IR analysis results of polymer (88) obtained in Example 20.

150 mg of Na salt-form polymer (85) obtained in Example 19 was diluted with water and dissolved into 150 ml of a solution. The aqueous solution was treated by ultrasonic homogenizer (manufactured by NIHONSEIKI KAISHA LTD., US-300T), and cation exchange resin Amberlite (IR120H) was added thereto, followed by stirring overnight. Amberlite was removed by filtration under reduced pressure to obtain a deep blue H-form polymer aqueous solution. The aqueous solution was roughly concentrated, the resulting aqueous solution was added to acetone, and the obtained precipitate was recovered by filtration under reduced pressure. After drying, 85 mg (yield: 57%) of the desired H-form polymer (88) was obtained as a black solid. As a result of UV-Vis-NIR analysis with respect to an aqueous solution containing 100 ppm of this polymer, long-wavelength absorption resulting from doping was observed (FIG. 19). In FIG. 23 are shown results of IR analysis. Characteristics band absorption in the vicinity of from 3,600 to 1,800 cm$^{-1}$ resulting from doping was observed. Further, the electric conductivity of a film obtained by casting a 0.5 wt % aqueous solution of this polymer on an alkali-free glass plate was 9.0 S/cm. The particle size (D50) of the polymer in a 1.0 wt % aqueous solution was at most the detection limit (0.8 nm), and the aqueous solution passed through a 0.05 μm filter.

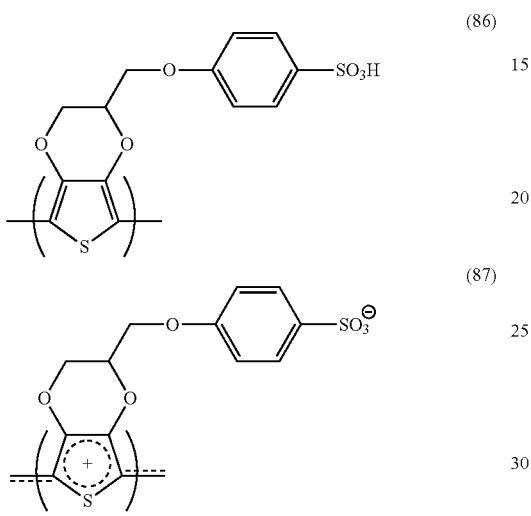

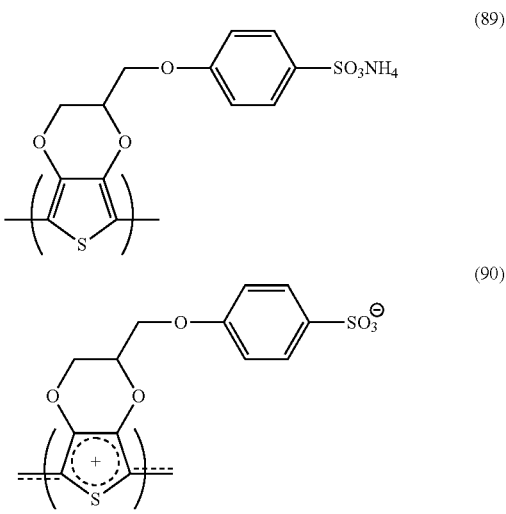

Example 21: Preparation of Polymer (91) (Polymer Containing Structural Units Represented by the Following Formula (89) or (90))

Figure 20:
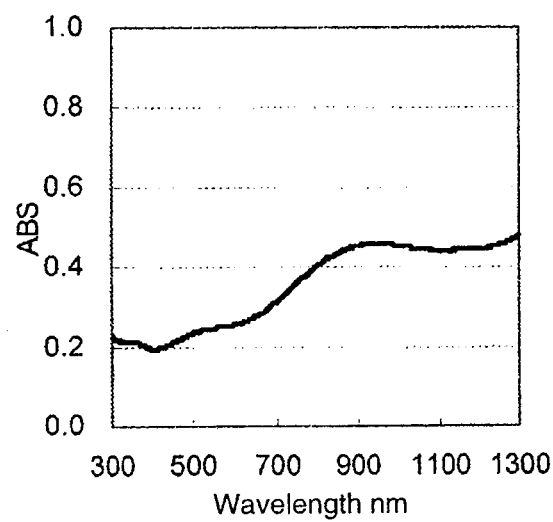
FIG. 20 illustrates UV-Vis-NIR analysis results of polymer (91) obtained in Example 21.
Figure 24:
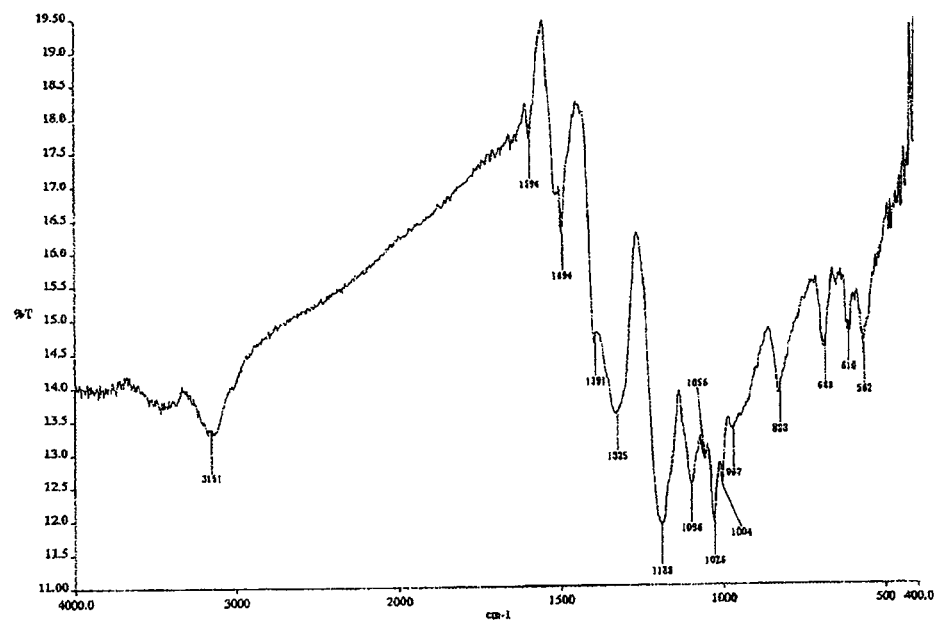
FIG. 24 illustrates IR analysis results of polymer (91) obtained in Example 21.

150 mg of Na salt-form polymer (85) obtained in Example 19 was diluted with water and dissolved into 15 g of a solution. To the aqueous solution, cation exchange resin Amberlite (IR120H) was added, followed by stirring overnight. Amberlite was removed by filtration under reduced pressure to obtain a deep blue H-form polymer aqueous solution. The aqueous solution was roughly concentrated, a 2.8 wt % ammonia water in an amount excess to the number of moles per monomer repeating unit was added thereto, followed by stirring in nitrogen at room temperature overnight. The reaction mixture was subjected to filtration under reduced pressure, the obtained filtrate was roughly concentrated, the resulting aqueous solution was added to acetone, and the obtained precipitate was recovered by filtration under reduced pressure. After drying, 90 mg (yield: 60%) of the desired NH$_4$ salt-form black polymer (91) was obtained. As a result of UV-Vis-NIR analysis with respect to an aqueous solution containing 100 ppm of this polymer, long-wavelength absorption resulting from doping was observed (FIG. 20). In FIG. 24 are shown results of IR analysis. Characteristics band absorption in the vicinity of from 3,600 to 1,800 cm$^{-1}$ resulting from doping was observed. Further, the electric conductivity of a film obtained by casting a 0.5 wt % aqueous solution of this polymer on an alkali-free glass plate was 7.5 S/cm. The particle size (D50) of the polymer in a 0.5 wt % aqueous solution was at most the detection limit (0.8 nm), and the aqueous solution passed through a 0.05 μm filter.

Example 22: Preparation of Polymer (91) (Polymer Containing Structural Units Represented by the Above Formula (89) or (90))

80 mg of H-form polymer (88) obtained in Example 20 was diluted with water and dissolved into 8 mL of a solution. To the aqueous solution, a 2.8 wt % ammonia water in an amount excess to the number of moles per monomer repeating unit was added, followed by stirring in nitrogen at room temperature overnight. The reaction mixture was subjected to filtration under reduced pressure, the obtained filtrate was roughly concentrated, the resulting aqueous solution was added to acetone, and the obtained precipitate was recovered by filtration under reduced pressure. After drying, 40 mg (yield: 50%) of the desired NH$_4$ salt-form black polymer (91) was obtained. By UV-Vis-NIR analysis and IR analysis with respect to an aqueous solution containing 100 ppm of this polymer, the same results as in Example 21 were obtained. Further, the electric conductivity of a film obtained by casting a 0.5 wt % aqueous solution of this polymer on an alkali-free glass plate was 6.0 S/cm. The particle size (D50) of the polymer in a 0.5 wt % aqueous solution was at most the detection limit (0.8 nm), and the aqueous solution passed through a 0.05 μm filter.

Example 23: Preparation of Polymer (85) (Polymer Containing Structural Units Represented by the Above Formula (83) or (84))

Figure 21:
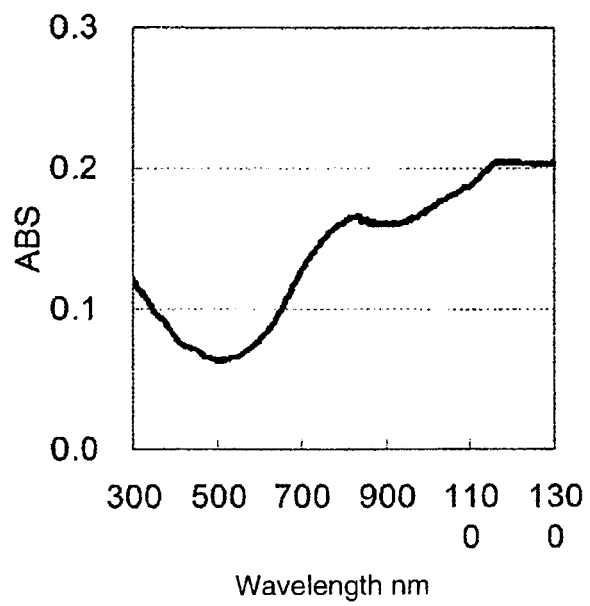
FIG. 21 illustrates UV-Vis-NIR analysis results of polymer (85) obtained in Example 23.

In a 30 mL reaction tube equipped with a nitrogen line, 580 mg (1.58 mmol) of compound represented by the above formula (82) obtained in Example 18 was dissolved in 6.3 g of water to obtain a monomer aqueous solution. Then, an oxidizing agent aqueous solution was separately prepared by dissolving 13 mg (0.08 mmol) of FeCl$_3$ and 754 mg (3.17 mmol) of Na$_2$S$_2$O$_8$ in 7.9 g of water, and it was slowly added to the monomer aqueous solution, followed by polymerization at room temperature for 14 hours. During the polymerization, the solution was changed from reddish purple to deep bluish purple. The obtained polymer solution was slowly added to 500 mL of acetone with stirring, and the obtained precipitate was recovered by filtration under reduced pressure (0.82 g, blue solid). This solid was dissolved in 30 mL of water to obtain an aqueous solution, and inorganic salt was removed by dialysis (dialysis membrane: Spectra/Por MWCO=0.1 to 0.5 K) (two days). The purified aqueous solution was roughly concentrated and added to acetone, and the obtained precipitate was recovered by filtration under reduced pressure. After drying, 170 mg (yield: 29%) of the desired Na salt-form pale green polymer (85) was obtained. As a result of UV-Vis-NIR analysis with respect to an aqueous solution containing 100 ppm of this polymer, long-wavelength absorption resulting from doping was confirmed (FIG. 21). Further, the electric conductivity of a film obtained by casting a 0.5 wt % aqueous solution of this polymer on an alkali-free glass plate was 2.8 S/cm. The particle size (D50) of the polymer in a 0.5 wt % aqueous solution was at most the detection limit (0.8 nm), and the aqueous solution passed through a 0.05 μm filter. The weight average molecular weight by GPC was 7,800.

Example 24: Preparation of Polymer (88) (Polymer Containing Structural Units Represented by the Above Formula (86) or (87))

In a 30 mL reaction tube equipped with a nitrogen line, 1.0 g (2.85 mmol) of compound represented by the above formula (82) obtained in Example 18 was dissolved in 14.3 g of water to obtain a monomer aqueous solution. Then, 0.23 g (1.42 mmol) of $FeCl_3$ was added thereto, followed by stirring for 30 minutes. To this solution, an oxidizing agent aqueous solution having 1.36 g (5.70 mmol) of $Na_2S_2O_8$ dissolved in 8.0 g of water was slowly added, followed by polymerization at room temperature for 12 hours. During the polymerization, the solution was changed from reddish purple to deep bluish purple. The obtained polymer solution was slowly added to 500 mL of acetone with stirring, and the obtained precipitate was recovered by filtration under reduced pressure (1.18 g, bluish green solid). This solid was dissolved in 300 g of water to obtain an aqueous solution, and cation exchange resin Amberlite (IR120H) was added, followed by stirring overnight. Amberlite was removed by filtration under reduced pressure to obtain a deep blue H-form polymer aqueous solution. The aqueous solution was further roughly concentrated to prepare a 1% aqueous solution, and inorganic salt was removed by dialysis (dialysis membrane: Spectra/Por MWCO=3,500) (two days). The purified aqueous solution was roughly concentrated and added to acetone, and the obtained precipitate was recovered by filtration under reduced pressure. After drying, 88 mg (yield: 9%) of the desired H-form black polymer (88) was obtained. As a result of UV-Vis-NIR analysis with respect to an aqueous solution containing 100 ppm of this polymer, long-wavelength absorption resulting from doping was confirmed. Further, the electric conductivity of a film obtained by casting a 0.5 wt % aqueous solution of this polymer on an alkali-free glass plate was 4.1 S/cm. The particle size (D50) of the polymer in a 0.5 wt % aqueous solution was at most the detection limit (0.8 nm), and the aqueous solution passed through a 0.05 μm filter. The weight average molecular weight by GPC was 14,000.

Now, Examples regarding the polythiophene (C) of the present invention will be described.

Example 25: Preparation of Sodium 3-[(2,3-dihydrothieno[3,4-b]-[1,4]dioxin-2-yl)methoxy]-1-methyl-1-propanesulfonate In nitrogen atmosphere, in a 100 mL eggplant flask, 0.437 g (10.9 mmol) of 60 wt % sodium hydride and 37 mL of toluene were charged and then 1.52 g (8.84 mL) of (2,3-dihydrothieno[3,4-b][1,4]dioxin-2-yl)methanol was added. Then, the reaction liquid was heated to the reflux temperature and stirred at the same temperature for one hour. Then, a mixed liquid comprising 1.21 g (8.89 mmol) of 2,4-butanesultone and 10 mL of toluene was dropwise added thereto, followed by stirring at the same temperature for 2 hours. After cooling, the obtained reaction liquid was dropwise added to 160 mL of acetone for re-precipitation. The obtained powder was collected by filtration and vacuum dried to obtain 1.82 g of sodium 3-[(2,3-dihydrothieno[3,4-b]-[1,4]dioxin-2-yl)methoxy]-1-methyl-1-propanesulfonate as a pale yellow powder with a yield of 62%. It was confirmed to be the desired product from $^1H$- and $^{13}C$-NMR.

$^1H$-NMR ($D_2O$) δ (ppm); 6.67 (s, 2H), 4.54-4.60 (m, 1H), 4.45 (dd, 1H, J=12.0, 2.2 Hz), 4.26 (dd, 1H, J=12.0, 6.8 Hz), 3.90-3.81 (m, 4H), 3.10-3.18 (m, 1H), 2.30-2.47 (m, 1H), 1.77-1.92 (m, 1H), 1.45 (d, 3H).

$^{13}C$-NMR ($D_2O$) δ (ppm); 14.91, 31.22, 53.13, 66.18, 69.18, 73.29, 73.36, 100.81, 100.94, 140.88, 141.06.

Example 26: Preparation of Polymer (Polymer Containing Structural Units Represented by the Following Formula (92) or (93))

In nitrogen atmosphere, in a 50 mL schlenk tube, 0.505 g (1.52 mmol) of sodium 3-[(2,3-dihydrothieno[3,4-b]-[1,4] dioxin-2-yl)methoxy]-1-methyl-1-propanesulfonate obtained in Example 25 and 7.5 mL of water were added, and 0.153 g (0.93 mmol) of anhydrous iron(III) chloride was added thereto at room temperature, followed by stirring for 20 minutes. Then, a mixed solution comprising 0.724 g (3.05 mmol) of sodium persulfate and 5 mL of water was dropwise added thereto by a syringe. After stirring at room temperature for 3 hours, the reaction liquid was dropwise added to 100 mL of acetone to precipitate black polymer. The polymer was collected by filtration and vacuum dried to obtain 0.88 g of a polymer of sodium 3-[(2,3-dihydrothieno[3,4-b]-[1,4]dioxin-2-yl)methoxy]-1-methyl-1-propanesulfonate. Then, water was added to the polymer to prepare a 1 wt % aqueous solution, to which 9.2 g of cation exchange resin (Lewatit MonoPlus S100 (H form)) was added, followed by stirring at room temperature for 13 hours. The ion exchange resin was separated by filtration to obtain a deep ultramarine blue aqueous solution. The obtained deep ultramarine blue aqueous solution was further subjected to dialysis (dialysis membrane: Spectra/Por MWCO=3,500) to remove inorganic salt. Further, the obtained deep ultramarine blue aqueous solution was concentrated to 6.3 g and re-precipitated in 120 mL of acetone to obtain 353 mg of a black powder (yield: 69%).

Figure 25:
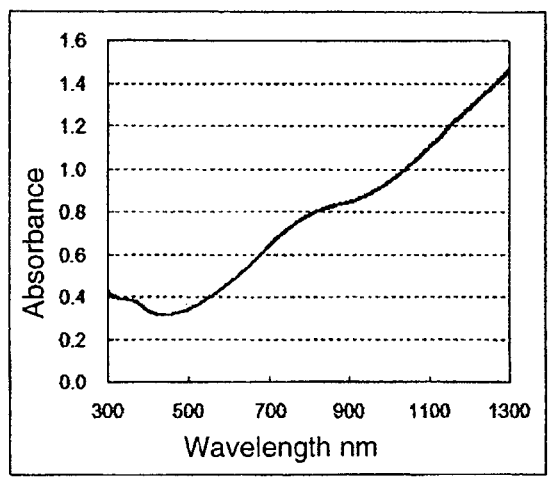
FIG. 25 illustrates UV-Vis-NIR analysis results of the polymer obtained in Example 26.

A 100 ppm aqueous solution of this polymer was prepared and subjected to UV-Vis-NIR analysis, whereupon long-wavelength absorption resulting from doping was observed (FIG. 25).

Further, of a film obtained by casting a 0.5 wt % aqueous solution of this polymer on an alkali-free glass plate (25 mm square), the surface resistance, the film thickness and the electric conductivity were 98 Ω/□, 1.9 μm and 54 S/cm, respectively. The value of the electric conductivity was about twice higher than the reported electric conductivity of PEDT-S. Further, the particle size (D50) of the polymer of a 0.5 wt % aqueous solution was at most the detection limit (0.8 nm). The results are summarized in Table 1.

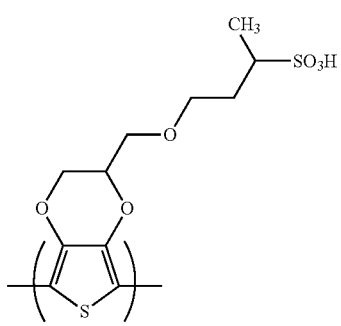

(92)

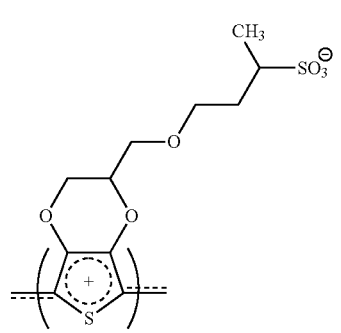

(93)

Comparative Example 4: Preparation of Polymer (Polymer Containing Structural Units Represented by the Following Formula (96) or (97))

Polymer was prepared in accordance with the following scheme with reference to Chemistry Materials, 21, 1815 to 1821 (2009) or Advanced Materials, 23 (38), 4403 to 4408 (2011).

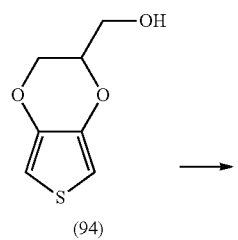

(94)

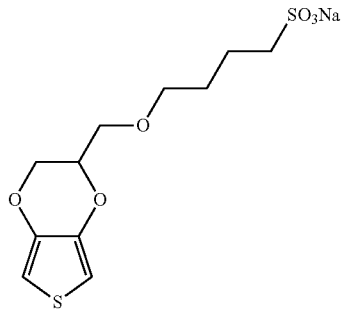

(95)

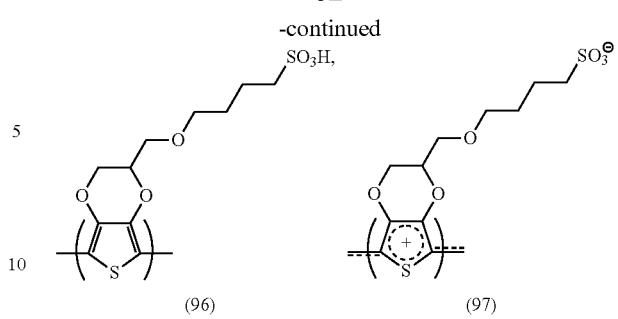

(96)　　　(97)

Into a 100 mL eggplant flask, 1.83 g of commercially available compound (94), 45 mL of toluene and 0.32 g (13.2 mmol) of 60 wt % NaH were charged and reacted under reflux conditions for one hour. 1.46 g (10.7 mmol) of 1,4-butanesultone dissolved in 12 mL of toluene was dropwise added thereto under reflux. The reaction mixture was aged further for 2 hours, cooled to room temperature and added to 200 mL of acetone to precipitate a jelly-like solid. The solid was collected by filtration with filter paper and dried under reduced pressure to obtain 2.0 g of the desired compound (95) as a pale brown solid (yield: 56%).

(1B) Preparation of Polymer (Polymer Containing Structural Units Represented by the Above Formula (96) or (97))

Into a 50 mL schlenk tube, 0.378 g (1.15 mmol) of compound (95) obtained in the above (3A) and 5.7 mL of water were charged to obtain a monomer aqueous solution. To the aqueous solution, 0.113 g (0.70 mmol) of $FeCl_3$ and a mixed solution comprising 0.554 g (2.33 mmol) of sodium persulfate and 3.8 mL of water were sequentially added, followed by stirring at room temperature for 3 hours.

The obtained polymer liquid was poured into 76 mL of acetone to precipitate polymer. The obtained slurry was subjected to centrifugal sedimentation (3,000 rpm) to obtain 0.74 g of a black solid. Then, water was added to the black solid to prepare a 1% aqueous solution, and 8.0 g of cation exchange resin (Lewatit MonoPlus S100 (H form)) was added, followed by stirring for 3 hours to obtain a H-form polymer solution. The ion exchange resin was removed by filtration, and the obtained mother liquid was further subjected to dialysis (dialysis membrane: Spectra/Por MWCO=3,500) to remove inorganic salt. The purified aqueous solution containing H-form polymer was concentrated to 4.3 g, and the obtained residue was poured into 80 mL of acetone to precipitate polymer. The obtained slurry was subjected to centrifugal sedimentation (3,000 rpm) to obtain 0.188 g of H-form polymer (yield: 49%).

The electric conductivity of a film obtained by casting a 0.5 wt % aqueous solution of this polymer on an alkali-free glass plate was 22 S/cm. The particle size (D50) of the polymer in a 0.5 wt % aqueous solution was at most the detection limit (0.8 nm).

Comparative Example 5: Preparation of Polymer (Polymer Containing Structural Units Represented by the Following Formula (101) or (102))

Polymer was prepared in accordance with the following scheme with reference to Japanese Patent No. 3182239.

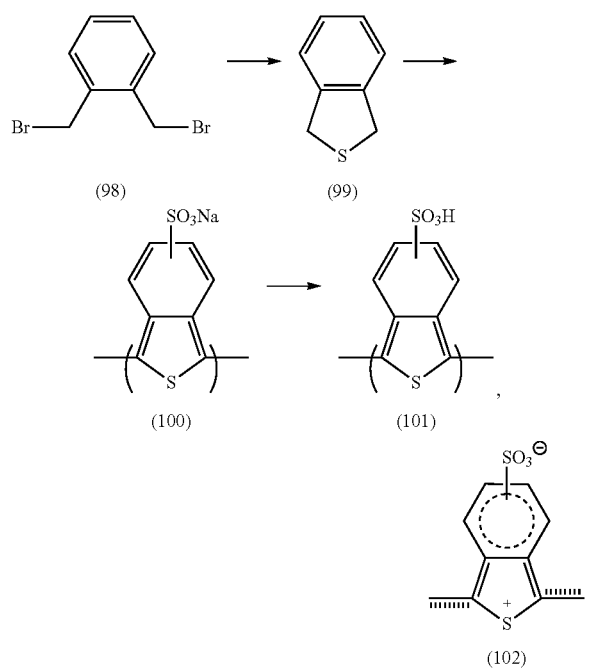

(2A) Preparation of 1,3-dihydroisothianaphthene (99)

Into a 2 L separable flask, 10.0 g (38.0 mmol) of compound (98), 25.7 g (75.8 mmol) of tetra-n-butylammonium hydrogensulfate and 950 mL of chloroform were charged. After nitrogen bubbling, a preliminarily prepared aqueous solution having 13.9 g (57.8 mmol) of sodium sulfide nonahydrate and 6.4 g (75.6 mmol) of sodium hydrogen carbonate dissolved in 700 mL of water was dropwise added thereto at room temperature over a period of 1.5 hours, followed by ageing further for one hour. After the reaction, the resulting organic layer was separated by liquid separation and washed twice with 250 mL of water. The organic layer was dried over magnesium sulfate and concentrated to obtain a mixture of a white solid and an oily substance. Continuously, the mixture was purified by silica gel chromatography (eluent: hexane/chloroform=4/1) to obtain 2.8 g of the desired compound (99) as a colorless transparent oily substance (yield: 55%).

(2B) Preparation of Polymer (100)

Into a 30 mL reaction tube, 3.0 g of 30% fuming sulfuric acid was charged and cooled in an ice bath. Further, in a stream of nitrogen, compound (99) obtained in the above (2A) was dropwise added to the fuming sulfuric acid by a syringe, followed by stirring at room temperature for one hour and then by reaction at 70° C. for one hour. The reaction liquid was changed from brown to deep ultramarine blue immediately after dropwise addition. After the reaction, the reaction liquid was dropwise added to 200 mL of a 0.1N NaOH-methanol solution to precipitate polymer. The polymer was sedimented by centrifugal separation (3,000 rpm) and dried to obtain 1.4 g of a black powder. Continuously, the black powder was dissolved in 100 g of water, and inorganic salt was removed by dialysis (dialysis membrane: Spectra/Por MWCO=0.1 to 0.5 K). The purified aqueous solution was concentrated and dried to obtain 1.1 g of the desired Na salt-form polymer (100) as a black solid (yield: 64%).

(2C) Preparation of Polymer (Polymer Containing Structural Units Represented by the Following Formula (101) or (102))

Into a 30 mL reaction tube, 160 mg of the Na salt-form polymer (100) obtained in the above (2B) and 23 g of water were charged to prepare an aqueous solution. To the aqueous solution, 2.5 g of cation exchange resin (Lewatit S100) which had been preliminarily converted to an acid form was added, followed by stirring overnight. The ion exchange resin was removed by filtration, and the obtained filtrate was concentrated and dried to obtain 140 mg of the desired acid-form polymer as a black solid (yield: 89%). The electric conductivity of a film obtained by casting a 0.5 wt % aqueous solution of this polymer on an alkali-free glass plate was 0.1 S/cm. The particle size (D50) of the polymer in a 0.5 wt % aqueous solution was 6 nm.

TABLE 1

| | Polymer structure | Surface resistance Ω/□ | Film thickness μm | Electric conductivity S/cm | $D_{50}$ nm |
|---|---|---|---|---|---|
| Ex. 26 | 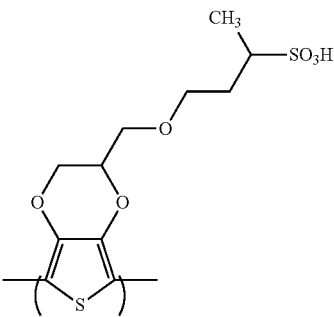 | 9.8 × 10 | 1.9 | 54 | <0.8 |

TABLE 1-continued

| Polymer structure | Surface resistance Ω/□ | Film thickness μm | Electric conductivity S/cm | $D_{50}$ nm |
|---|---|---|---|---|
| Comp. Ex. 4 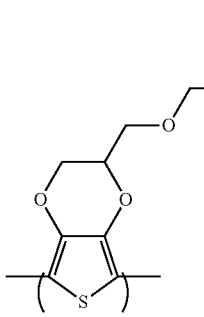 | $5.5 \times 10^2$ | 0.84 | 22 | <0.8 |
| Comp. Ex. 5 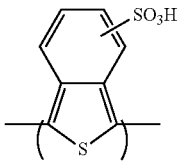 | $7.4 \times 10^4$ | 1.3 | 0.1 | 6 |

Example 27: Preparation of Polymer Aqueous Solution (the Above Formula (5) or (6), Wherein M=H and R=CH₃)

In a 500 mL separable flask, 15 g (45 mmol) of sodium 3-[(2,3-dihydrothieno[3,4-b]-[1,4]dioxin-2-yl)methoxy]-1-methyl-1-propanesulfonate and 225 g of water were added. After dissolution, 4.41 g (27.2 mmol) of anhydrous iron(III) chloride was added at room temperature, followed by stirring for 20 minutes. Then, a mixed solution comprising 21.7 g (91.1 mmol) of sodium persulfate and 150 g was dropwise added thereto while the reaction liquid temperature was maintained to be at most 30° C. After stirring at room temperature for 3 hours, the reaction liquid was dropwise added to 1.3 kg of acetone to precipitate black Na-form polymer. The obtained polymer was subjected to filtration and vacuum dried to obtain 28.0 g of crude polymer of sodium 3-[(2,3-dihydrothieno[3,4-b]-[1,4]dioxin-2-yl) methoxy]-1-methyl-1-propanesulfonate.

Then, water was added to the crude polymer to prepare a 2 wt % aqueous solution, and 1.4 kg of this aqueous solution was passed through a column packed with 400 mL of cation exchange resin (Lewatit MonoPlus S100 (H form)) (space velocity: 1.1) to obtain 1.48 kg of a H-form polymer aqueous solution. Further, the polymer aqueous solution was purified by cross flow ultrafiltration (filter: Vivaflow 200, MWCO=10,000, filter powder: 10) to prepare 1.4 kg of a deep ultramarine blue aqueous solution of polymer containing structural units represented by the above formula (92) or (93). The amount of polymer contained in the polymer aqueous solution was 0.84 wt %, and the contents of iron ions and sodium ions which are considered to be impurities were 260 ppb and 100 ppb, respectively, by ICP-MS analysis.

Figure 26:
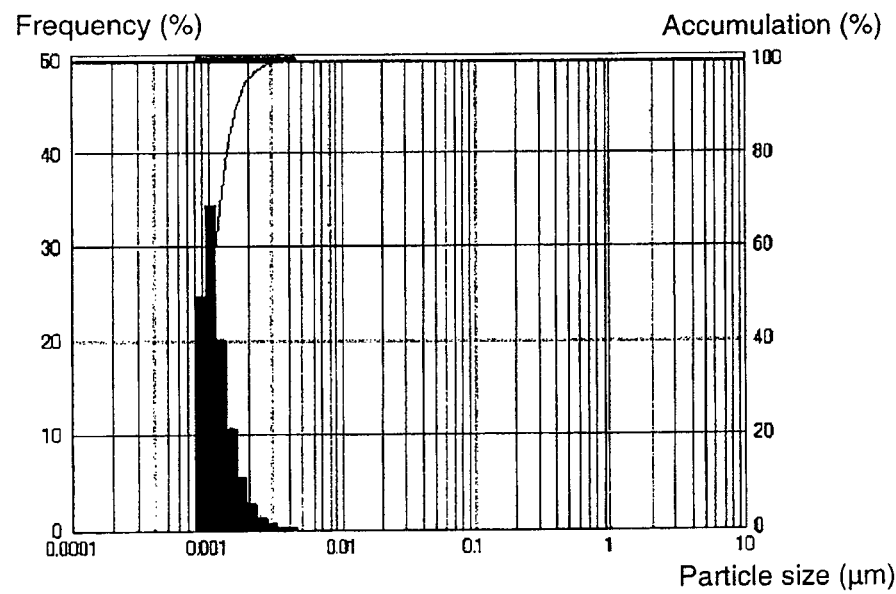
FIG. 26 illustrates results of measurement of the particle size distribution of polymer obtained in Example 27 in a 2.0 wt % aqueous solution.

Of a film obtained by casting the polymer aqueous solution on an alkali-free glass plate (25 mm square), the surface resistance, the film thickness and the electric conductivity were 20 Ω/□, 3.5 μm and 140 S/cm, respectively. The electric conductivity was about seven times higher than the electric conductivity of PEDT-S. Further, the particle size (D50) of the polymer in a 2.0 wt % aqueous solution was 1.1 nm. The particle size distribution of the polymer in a 2.0 wt % aqueous solution is shown in FIG. 26.

Example 28: Preparation of Ammonium Salt (the Above Formula (5) or (6), Wherein M=NH₄ and R=CH₃)

920 g of the H-form polymer aqueous solution obtained in Example 27 was concentrated under reduced pressure to obtain 386 g of a 2 wt % polymer aqueous solution. In an Erlenmeyer flask, 90 g of the 2 wt % H-form polymer aqueous solution was added, and 9 mL of a 29 wt % ammonia water was dropwise added at room temperature, followed by stirring overnight. The reaction liquid was concentrated, and the concentrated liquid was dropwise added to 200 mL of acetone, whereby an ammonium salt was formed as a precipitate. By filtration and drying, 1.72 g of an ammonium salt was obtained as a black powder.

Further, of a film obtained by casting a 0.5 wt % aqueous solution of the polymer on an alkali-free glass plate (25 mm square), the surface resistance, the film thickness and the electric conductivity were 98 Ω/□, 1.2 μm and 85 S/cm, respectively. Further, the particle size (D50) of the polymer in a 2.0 wt % aqueous solution was 1.1 nm. The results are shown in Table 2.

TABLE 2

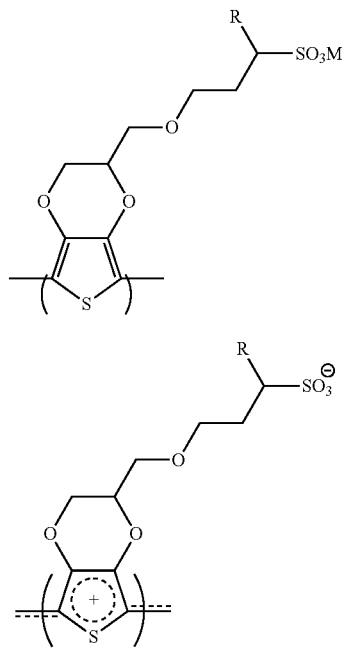

| Ex. | 28 | 29 | 30 | 31 | 32 |
|---|---|---|---|---|---|
| R | $CH_3$ | $CH_3$ | $CH_3$ | $CH_3$ | $CH_3$ |
| M | $NH_4$ | $NH_3(CH_2CH_2OH)$ | $NH(CH_3)_2(CH_2CH_2OH)$ | $NH(CH_3)_2(CH_2CH(OH)CH_2OH)$ | $NH_2(CH_2CH_2OH)_2$ |
| Surface resistance Ω/□ | 98 | 106 | 114 | 148 | 113 |
| Film thickness μm | 1.2 | 1.2 | 1.4 | 1.2 | 1.7 |
| Electric conductivity S/cm | 85 | 79 | 63 | 56 | 52 |
| $D_{50}$ (2 wt %) nm | 1.1 | 1.1 | 1.1 | 1.1 | 1.1 |

Example 29: Preparation of Ethanolamine Salt (the Above Formula (5) or (6), wherein M=$NH_3$($CH_2CH_2OH$))

A 50 wt % ethanolamine aqueous solution was dropwise added to 10 g of the 2 wt % H-form polymer aqueous solution obtained in Example 28 to neutralize the polymer aqueous solution (pH=7) to obtain an ethanolamine salt aqueous solution.

This polymer aqueous solution was adjusted to 0.5 wt %, and 0.5 mL of the aqueous solution was cast on an alkali-free glass plate, followed by annealing at 120° C. for 20 minutes, and the electric conductivity of the obtained film was 79 S/cm.

Further, the average particle size (D50) of the polymer in a 2.0 wt % aqueous solution was 1.1 nm. The results are shown in Table 2.

Examples 30 to 32

In accordance with Example 29, N,N'-dimethylethanolamine salt (Example 30), 3-(dimethylamino)-1,2-propanediol salt (Example 31) and diethanolamine salt (Example 32) were prepared. The results are shown in Table 2.

Example 33: Preparation of Polymer (Polymer Containing Structural Units Represented by the Following Formula (103) or (104))

In accordance with WO2006/085149, 3.0 g of 1-ethyl-1, 3-propanesultone was prepared. Then, in accordance with Example 25 except that 2,4-butanesultone was changed to 1-ethyl-1,3-propanesultone, 1.9 g of sodium 3-[(2,3-dihydrothieno[3,4-b]-[1,4]dioxin-2-yl)methoxy]-1-ethyl-1-propanesulfonate was prepared as a pale yellow powder.

Continuously, in accordance with Example 26 except that sodium 3-[(2,3-dihydrothieno[3,4-b]-[1,4]dioxin-2-yl) methoxy]-1-methyl-1-propanesulfonate was changed to sodium 3-[(2,3-dihydrothieno[3,4-b]-[1,4]dioxin-2-yl) methoxy]-1-ethyl-1-propanesulfonate, 363 mg of a black powder polymer was prepared.

The electric conductivity of a film obtained by casting a 0.5 wt % aqueous solution of this polymer on an alkali-free glass plate (25 mm square) was 44 S/cm.

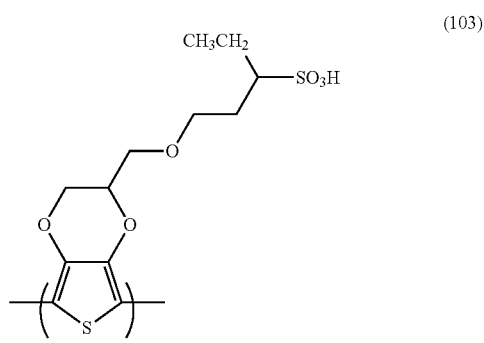

(103)

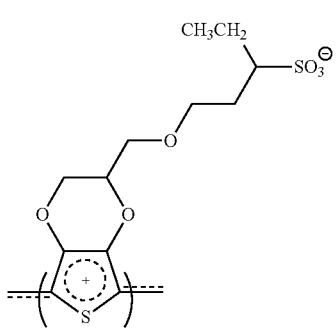

(104)

Example 34: Test on Penetration of Alumina by Electrically Conductive Polymer

Figure 27:
FIG. 27 illustrates results of Tests on penetration of alumina by electrically conductive polymer.
Figure 27:
Figure 27:
Figure 27:

In 1.0 g of the about 2 wt % electrically conductive polymer aqueous solution prepared in Example 29, γ-alumina (manufactured by Sumitomo Chemical Co., Ltd., NKHO-24, specific surface area: 170 m²/g, pore volume: 0.62 mL/g, average pore size: 11 nm) was dipped for one hour. Then, the γ-alumina was dried at 120° C. for 30 minutes, and then its cross section was visually observed to evaluate the penetration property of the blue black electrically conductive polymer. The results are shown in FIG. 27.

Examples 35 to 37

The same test on penetration of alumina as in Example 34 was carried out using the electrically conductive polymer aqueous solutions prepared in Examples 30 to 32. The results are shown in FIG. 27. As evident from FIG. 27, in each of Examples 34 to 37, the spherical γ-alumina from its surface to a sufficient depth of from 0.7 to 1 mm was colored blue black (grayish black in the photographs of alumina cross section in FIG. 27), and it was confirmed that the electrically conductive polymer can sufficiently penetrate even into an average pore size of 11 nm.

INDUSTRIAL APPLICABILITY

According to the present invention, a novel polythiophene having both favorable electrical conductivity and water solubility sufficient for forming can be provided. This novel polythiophene is applicable to an antistatic agent, a solid electrolyte of a capacitor, an electrically conductive coating material, an electrochromic device, a transparent electrode, a transparent electrically conductive film, a chemical sensor, an actuator, etc. Particularly, it is water-soluble and is thereby less likely to damage a lipid-soluble resist, and separation by washing is easily carried out, and therefore its use as an antistatic film-forming material to suppress electrification of a resist at the time of electron lithography is expected. Further, since the polythiophene of the present invention has a very small polymer particle size when formed into an aqueous solution, for example, it readily infiltrate into a chemically treated etched aluminum foil of an aluminum solid electrolytic capacitor, thus increasing the area covered with the electrically conductive polymer, and thus improvement in the capacitor performance such as an increase of the electrostatic capacitance and a low ESR are expected.

The entire disclosure of Japanese Patent Application No. 2012-149785 filed on Jul. 3, 2012, Japanese Patent Application No. 2012-149786 filed on Jul. 3, 2012, Japanese Patent Application No. 2012-167770 filed on Jul. 27, 2012, Japanese Patent Application No. 2012-167771 filed on Jul. 27, 2012, Japanese Patent Application No. 2012-196153 filed on Sep. 6, 2012, Japanese Patent Application No. 2012-199841 filed on Sep. 11, 2012, and Japanese Patent Application No. 2013-078336 filed on Apr. 4, 2013, including specifications, claims, drawings and summaries are incorporated herein by reference in their entireties.

The invention claimed is:

1. A polythiophene comprising at least one type of structural units selected from the group consisting of structural units represented by the following formula (3), structural units represented by the following formula (4), structural units represented by the following formula (5) and structural units represented by the following formula (6):

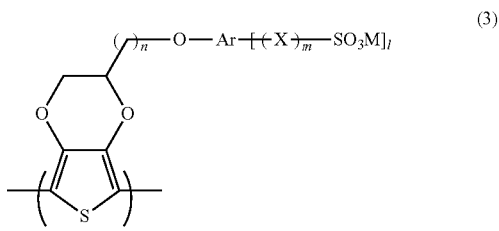

(3)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, n is an integer of from 0 to 6, m in an integer of 0 or 1, and l is an integer of from 1 to 4;

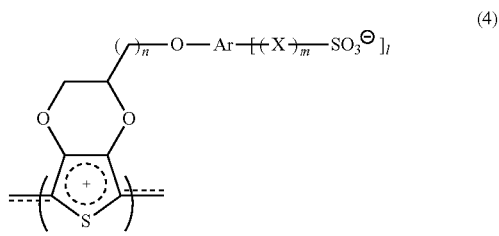

(4)

wherein Ar, X, n, m and l are as defined in the above formula (3);

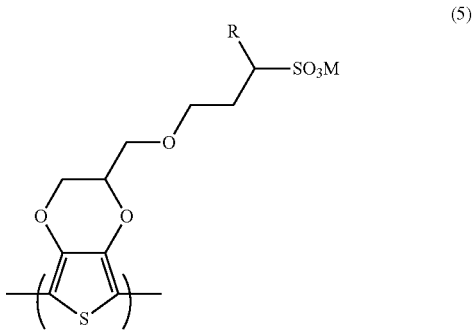

(5)

wherein R is a $C_{1-6}$ linear or branched alkyl group, or a fluorine atom, M is a hydrogen atom, an alkali metal selected from the group consisting of Li, Na and K, $NH(R^1)_3$ or $HNC_5H_5$, and $R^1$ is each independently a hydrogen atom, or a $C_{1-6}$ alkyl group which may have a substituent; and

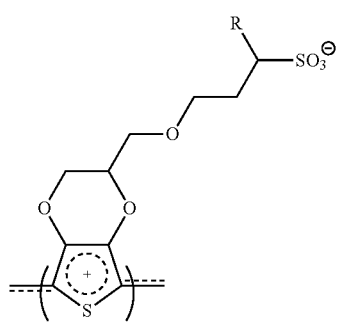
(6)

wherein R is as defined in the above formula (5).

2. The polythiophene according to claim 1, which contains at least one type of structural units selected from the group consisting of structural units represented by the following formula (13):

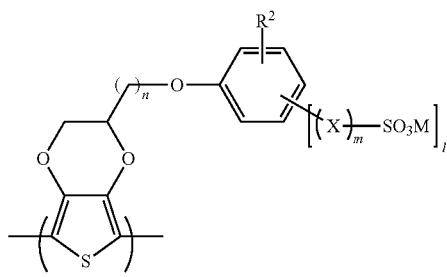
(13)

wherein M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, X is a $C_{1-6}$ alkylene group which may have a substituent, $R^2$ is a hydrogen atom, or a $C_{1-6}$ alkyl group or alkoxy group which may have a substituent, n is an integer of from 0 to 6, m is an integer of 0 or 1, and l is an integer of from 1 to 4; and structural units represented by the following formula (14):

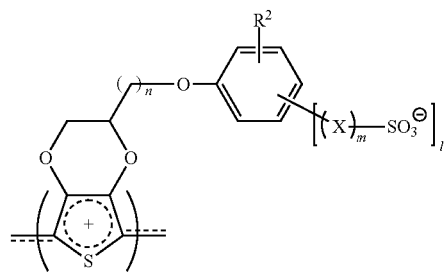
(14)

wherein $R^2$, X, n, m, and l are as defined in the above formula (13).

3. The polythiophene according to claim 2, wherein in the structural units represented by the formula (13) or (14), $R^2$ is a hydrogen atom and l=1.

4. The polythiophene according to claim 1, which has a weight average molecular weight within a range of from 1,000 to 1,000,000 as calculated as polystyrene sulfonic acid.

5. A water-soluble electrically conductive polymer aqueous solution comprising an aqueous solution of the polythiophene as defined in claim 1.

6. A method for producing an electrically conductive coating film, which comprises applying the aqueous solution as defined in claim 5 to a substrate, followed by drying.

7. Use of the aqueous solution as defined in claim 5 for an electrically conductive coating film.

8. A method for producing the polythiophene as defined in claim 1, which comprises polymerizing at least one thiophene compound selected from the group consisting of a thiophene compound represented by the following formula (16) and a thiophene compound represented by the following formula (17) in water or an alcohol solvent in the presence of an oxidizing agent:

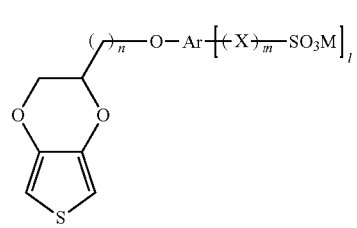
(16)

wherein Ar is a $C_{6-20}$ arylene group which may have a substituent, X is a $C_{1-6}$ alkylene group which may have a substituent, M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, n is an integer of from 0 to 6, m is an integer of 0 or 1, and l is an integer of from 1 to 4; and

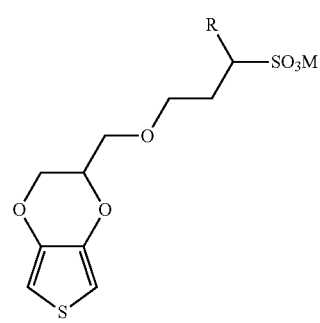
(17)

wherein R is a $C_{1-6}$ linear or branched alkyl group or a fluorine atom, M is a hydrogen atom, an alkali metal selected from the group consisting of Li, Na and K, $NH(R^1)_3$ or $HNC_5H_5$, and $R^1$ is each independently a hydrogen atom or a $C_{1-6}$ alkyl group which may have a substituent.

9. The production method according to claim 8, wherein the thiophene compound is at least one member selected from the group consisting of a compound represented by the following formula (21):

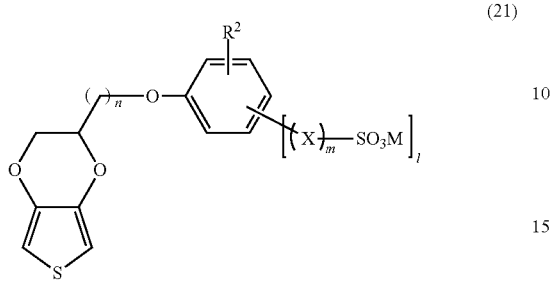

(21)

wherein M is a hydrogen atom, an alkali metal selected from the group consisting of Li, Na and K, $NH(R^1)_3$ or $HNC_5H_5$, $R^1$ is each independently a hydrogen atom or a $C_{1-6}$ alkyl group which may have a substituent, $R^2$ is a hydrogen atom, or a $C_{1-6}$ alkyl group or alkoxy group which may have a substituent, X is a $C_{1-6}$ alkylene group which may have a substituent, n is an integer of from 0 to 6, m is an integer of 0 or 1, and l is an integer of from 1 to 4.

10. The method for producing a polythiophene according to claim 8, wherein the oxidizing agent is an iron (III) salt or a combination of a persulfate and an iron (III) salt.

* * * * *